United States Patent [19]

Chen

[11] Patent Number: 5,015,473
[45] Date of Patent: May 14, 1991

[54] 6-(SUBSTITUTED)METHYLENEPENICIL-LANIC AND 6-(SUBSTITUTED)HYDROXYMETHYL-PENICILLANIC ACIDS AND DERIVATIVES THEREOF

[75] Inventor: Yuhpyng L. Chen, Groton, Conn.

[73] Assignee: Pfizer Inc., New York, N.Y.

[21] Appl. No.: 297,815

[22] Filed: Jan. 13, 1989

Related U.S. Application Data

[60] Division of Ser. No. 892,001, Jul. 30, 1986, Pat. No. 4,826,833, which is a continuation-in-part of Ser. No. 679,192, Dec. 11, 1984, abandoned, which is a continuation-in-part of Ser. No. 575,354, Jan. 30, 1984, abandoned.

[51] Int. Cl.$^5$ ............... C07D 499/00; A61K 31/425
[52] U.S. Cl. ................... 424/114; 540/310; 514/192; 514/195
[58] Field of Search ............ 424/114; 540/310; 514/192, 195

[56] References Cited

U.S. PATENT DOCUMENTS

| | | | |
|---|---|---|---|
| 4,143,046 | 3/1979 | Sheehan et al. | 260/306.7 |
| 4,287,181 | 9/1981 | Kellogg | 424/114 |
| 4,419,284 | 12/1983 | Crawford | 260/245.2 R |
| 4,485,110 | 11/1984 | Osborne | 424/270 |
| 4,512,999 | 4/1987 | Adam-Molina | 540/310 |

FOREIGN PATENT DOCUMENTS

| | | |
|---|---|---|
| 5889 | 12/1979 | European Pat. Off. |
| 18305 | 10/1980 | European Pat. Off. |
| 50805 | 5/1982 | European Pat. Off. |
| 0069373 | 1/1983 | European Pat. Off. |
| 2053220 | 2/1981 | United Kingdom. |

*Primary Examiner*—Nicholas S. Rizzo
*Attorney, Agent, or Firm*—Peter C. Richardson; J. Trevor Lumb; Gregg C. Benson

[57] ABSTRACT

Beta-lactamase inhibiting compounds of the formula

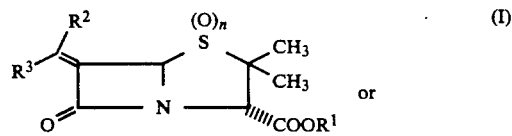

or

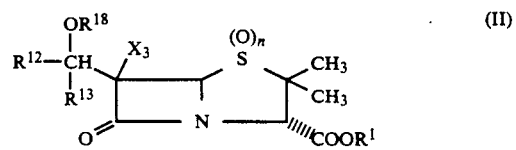

or a pharmaceutically acceptable acid addition or carboxylate salt thereof; where n is zero, 1 or 2; $X_3$ is H or Br, $R^1$ is H, the residue of certain carboxy-protecting groups or the residue of an ester group readily hydrolyzable in vivo; one of $R^{12}$ and $R^{13}$ is H and the other is vinyl, certain aryl, alkylthio, alkylsulfonyl or certain heterocyclyl, aminomethyl, thiocarboxyamido or amidino groups; one of $R^2$ and $R^3$ is H and the other is as disclosed for the other of $R^{12}$ and $R^{13}$, or is Cl or $CH_2OH$, and $R^{18}$ is H or certain acyl groups; intermediates useful in their production, methods for their preparation and use, and pharmaceutical compositions containing them.

25 Claims, No Drawings

6-(SUBSTITUTED)METHYLENEPENICILLANIC AND 6-(SUBSTITUTED)HYDROXYMETHYLPENICILLANIC ACIDS AND DERIVATIVES THEREOF

CROSS REFERENCE TO RELATED APPLICATION

This application is a division of copending application Ser. No. 892,001, filed July 30, 1986, now U.S. Pat. No. 4,826,833 which is a continuation-in-part of application Ser. No. 679,192 filed Dec. 11, 1984, now abandoned which is a continuation-in-part of the abandoned parent application Ser. No. 575,354 filed Jan. 30, 1984.

BACKGROUND OF THE INVENTION

The invention relates to novel 6-(substituted) methylenepenicillanic acids, and novel 6-(substituted)-hydroxymethylpenicillanic acids, certain esters and pharmaceutically acceptable salts thereof, pharmaceutical compositions containing them, methods for their preparation and their use as beta-lactamase inhibitors and intermediates therefor.

One of the most well-known and widely used of the classes of antibacterial agents is the class known as the beta-lactam antibiotics. These compounds are characterized in that they have a nucleus consisting of a 2-azetidinone (beta-lactam) ring fused to either a thiazolidine or a dihydro-1,3-thiazine ring. When the nucleus contains a thiazolidine ring, the compounds are usually referred to generically as penicillins, whereas when the nucleus contains a dihydrothiazine ring, the compounds are referred to as cephalosporins. Typical examples of penicillins which are commonly used in clinical practice are benzylpenicillin (penicillin G), phenoxymethylpenicillin (penicillin V), ampicillin and carbenicillin; typical examples of common cephalosporins are cephalothin, cephalexin and cefazolin.

However, despite the wide use and wide acceptance of the beta-lactam antibiotics as valuable chemotherapeutic agents, they suffer from the major drawback that certain members are not active against certain microorganisms. It is thought that in many instances this resistance of a particular microorganism to a given beta-lactam antibiotic results because the microorganism produces a beta-lactamase. The latter substances are enzymes which cleave the beta-lactam ring of penicillins and cephalosporins to give products which are devoid of antibacterial activity. However, certain substances have the ability to inhibit beta-lactamases, and when a beta-lactamase inhibitor is used in combination with a penicillin or cephalosporin it can increase or enhance the antibacterial effectiveness of the penicillin or cephalosporin against certain microorganisms. It is considered that there is an enhancement of antibacterial effectiveness when the antibacterial activity of a combination of a beta-lactamase inhibiting substance and a beta-lactam antibiotic is significantly greater than the sum of the antibacterial activities of the individual components.

Thus, according to the invention, there are provided new compounds which are 6-(substituted)methylenepenicillanic acids, their 1-oxides, 1,1-dioxides and esters thereof readily hydrolyzable in vivo. These new penicillanic acids and their esters readily hydrolyzable in vivo are potent inhibitors of microbial beta-lactamases. Accordingly, there is also provided a method for enhancing the effectiveness of beta-lactam antibiotics, using these novel acids, their salts and certain readily hydrolyzable esters thereof.

Still further, there are provided derivatives of 6-(substituted)methylenepenicillanic acids, their 1-oxides and 1,1-dioxides having a carboxy protecting group, said compounds being useful as chemical intermediates.

Yet further, there are provided 6-(substituted)-hydroxymethylpenicillanic acids, their 1-oxides, 1,1-dioxides and salts and esters thereof which are useful both as chemical intermediates and as beta-lactamase inhibitors.

European Patent Application No. 50,805 discloses compounds of the formula

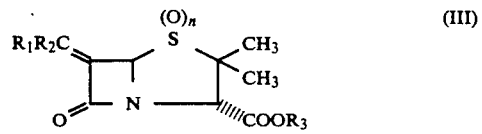

wherein n is zero, 1 or 2, $R_1$ is CN or certain carbonyl moieties; $R_2$ is hydrogen, lower alkyl or halogen and $R_3$ is hydrogen or a readily hydrolyzable group, useful as beta-lactamase inhibitors. The same reference discloses 6-oxopenicillanic acid esters, the corresponding sulfoxides and sulfones as well as a method for their use in preparation of compounds of formula (III) by reaction with a phosphoran of formula $R_1R_2C=P(C_6H_5)_3$.

United Kingdom Patent Application GB 2,053,220A discloses, inter alia, certain 6-methylene-1,1-dioxopenicillanic acids and esters of the above formula (III) where n is 2 and $R_1$ and $R_2$ independently denote hydrogen, an optionally substituted alkyl, aryl, optionally substituted cycloalkyl, an aralkyl or optionally substituted amino group, or together with the carbon atom to which they are attached, $R_1$ and $R_2$ form a 3 to 7-membered carbocyclic or heterocyclic ring.

U.S. Pat. No. 4,287,181 discloses certain 6-substituted penicillanic acid 1,1-dioxides and esters thereof wherein the 6-substituent is

and, inter alia, $R_3$ is H or alkanoyl and $R_4$ is H, $(C_1-C_4)$alkyl, phenyl, benzyl or pyridyl, which are useful as beta-lactamase inhibitors.

SUMMARY OF THE INVENTION

The present invention provides novel 6-(substituted)-methylenepenicillanates of the formula

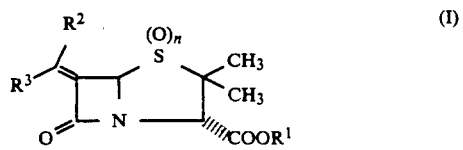

wherein n is zero, 1 or 2; $R^1$ is $R^a$ or $R^b$ where $R^a$ is the residue of a carboxy protecting group selected from tetrahydropyranyl, allyl, benzyl, 4-nitrobenzyl, benzhydryl, 2,2,2-trichloroethyl, t-butyl and phenacyl; and $R^b$ is hydrogen or the residue of an ester group readily hydrolyzable in vivo selected from 3-phthalidyl, 4-crotonolactonyl, gamma-butyrolacton-4-yl,

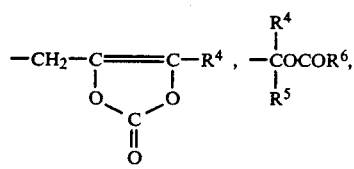 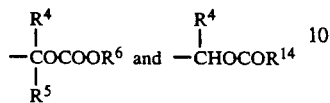

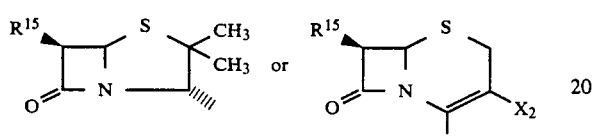

and $R^4$ and $R^5$ are each hydrogen or $CH_3$, $R^6$ is $(C_1-C_5)$-alkyl, and $R^{14}$ is

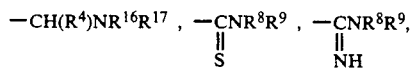

where $X_2$ is the 3-substituent of a known cephalosporin beta-lactam antibiotic and $R^{15}$ is the 6- or 7-substituent, respectively, of a known penicillin or cephalosporin beta-lactam antibiotic. Especially preferred $R^{14}$ are the above penicillin residues wherein $R^{15}$ is 2-phenylacetamido, 2-phenoxyacetamido, D-2-amino-2-phenylacetamido, D-2-amino-2-(4-hydroxyphenyl)acetamido, 2-carboxy-2-phenylacetamido, 2-carboxy-2-(2-thienyl)-acetamido, 2-carboxy-2-(3-thienylacetamido, D-2-(4-ethyl-2,3-dioxopiperazinocarbonylamino)-2-phenylacetamido, D-2-(4-ethyl-2,3-dioxopiperazinocarbonylamino)-2-(4-hydroxyphenyl)acetamido or 2,2-dimethyl-4-phenyl-5-imidazolidinone-1-yl;

one of $R^2$ and $R^3$ is hydrogen and the other is Cl, $CH_2OH$, vinyl, $(C_1-C_4)$alkylthio, $(C_1-C_4)$alkylsulfonyl, furyl, thienyl, N-methylpyrrolyl, N-acetylpyrrolyl,

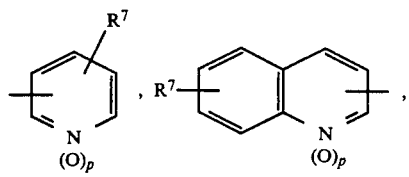

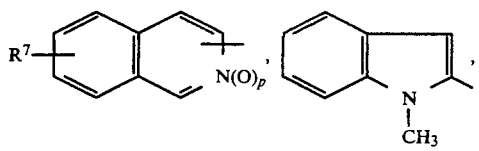

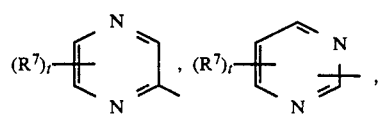

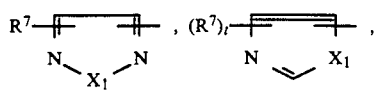

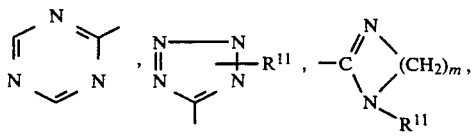

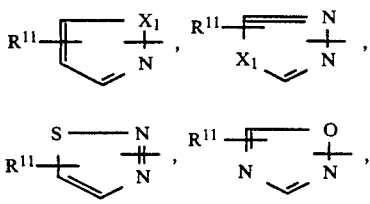

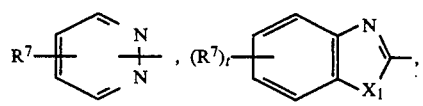

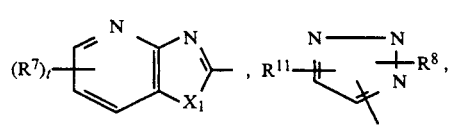

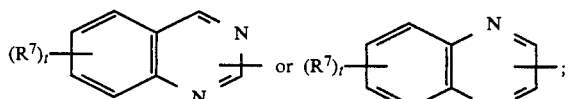

and m is 2 or 3, p is zero or 1, t is zero, 1 or 2, $X_1$ is S, O or $NR^{11}$, $R^7$ is hydrogen, $(C_1-C_4)$alkyl, $(C_1-C_4)$alkoxy, allyloxy, hydroxyl, carboxyl, $(C_2-C_5)$alkoxycarbonyl, $(C_1-C_5)$alkylcarbonyl, phenyl, benzyl, naphthyl, pyridyl, $NR^8R^9$, $CONR^8R^9$, $NHCOR^{10}$, $NO_2$, Cl, Br, $CF_3$ or $SR^8$; $R^8$ and $R^9$ are each hydrogen, $(C_1-C_4)$alkyl, phenyl or benzyl; $R^{10}$ is $(C_1-C_4)$alkyl, $CF_3$ or phenyl; $R^{11}$ is hydrogen, $(C_1-C_3)$alkyl $C_6H_5CH_2$ or $CH_3CO$; $R^{16}$ and $R^{17}$ are each H, $(C_1-C_4)$alkyl $(C_2-C_4)$hydroxyalkyl, or taken together with the nitrogen atom to which they are attached $R^{16}$ and $R^{17}$ form a 5- to 7-membered heterocyclic group, especially preferred such heterocyclic groups are pyrrolidino, piperidino, morpholino, thiomorpholino, or 4-methylpiperazino; or a pharmaceutically acceptable acid addition salt of said compound where $R^2$ or $R^3$ is a group which contains a basic nitrogen atom, or a pharmaceutically acceptable cationic salt of said compound wherein $R^1$ is hydrogen or $R^2$ or $R^3$ contains a carboxy group.

The above compounds wherein $R^1$ is $R^a$ are useful as intermediates for preparation of the compounds wherein $R^1$ is $R^b$. The latter compounds are the active beta-lactamase inhibitors of the invention.

The invention further provides 6-($R^{12}R^{13}$-substituted)hydroxymethylpenicillanic acids, 1-oxides, 1,1-dioxides and esters thereof of the formula

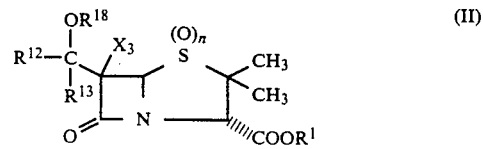

(II)

wherein n and $R^1$ are as defined above for compounds of formula (I), $X_3$ is H or Br, one of $R^{12}$ and $R^{13}$ is hydrogen and the other is vinyl, $(C_1-C_4)$alkylsulfonyl, furyl, thienyl, N-methylpyrrolyl, N-acetylpyrrolyl,

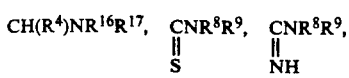

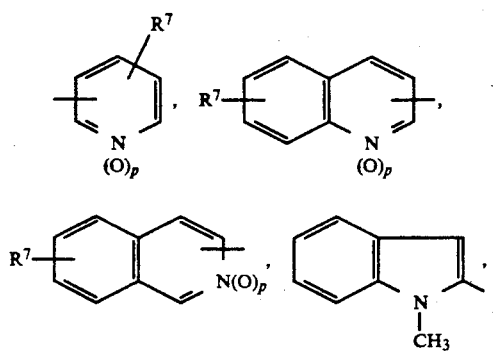

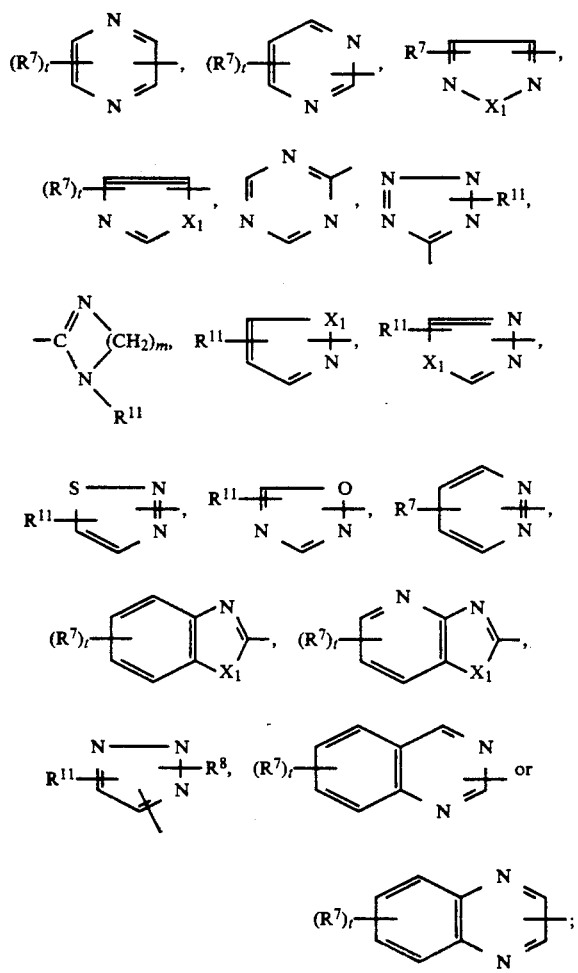

provided that when $R^{12}$ or $R^{13}$ is

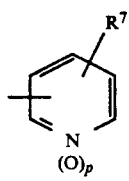

and p is zero, $R^7$ is other than H or $CH_3$; $R^{18}$ is H, $(C_2-C_5)$alkanoyl, $(C_2-C_5)$alkoxycarbonyl, pyrazinecarbonyl, benzoyl, $CF_3CO$ or $CONR^8R^9$; and m, p, t, $R^7$, $R^8$, $R^9$, $R^{11}$, $R^{16}$, $R^{17}$ and $X_1$ are as previously defined; or a pharmaceutically acceptable acid addition or carboxylate salt thereof.

The compounds of formula (II) are all useful as chemical intermediates for preparation of the corresponding 6-(substituted)methylene-1,1-dioxopenicillanates of formula (I). In addition, however, the compounds of formula (II) wherein $R^1$ is hydrogen or the residue of an ester group readily hydrolyzable in vivo, $R^b$, as defined above, are useful for their beta-lactamase inhibiting activity, especially when used in conjunction with a beta-lactam antibiotic.

Particularly preferred compounds of formula (I) are those wherein n is zero or 2 and one of $R^2$ and $R^3$ is hydrogen and the other is furyl, thienyl, $CH_2OH$, methylsulfonyl, N-methylpyrrolyl,

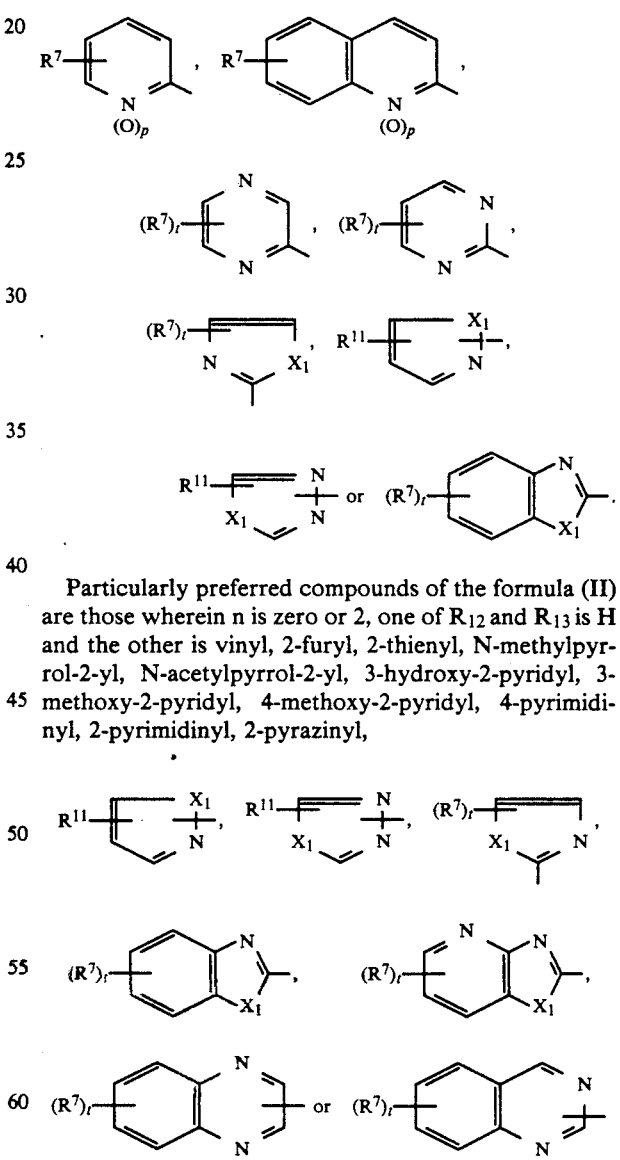

Particularly preferred compounds of the formula (II) are those wherein n is zero or 2, one of $R_{12}$ and $R_{13}$ is H and the other is vinyl, 2-furyl, 2-thienyl, N-methylpyrrol-2-yl, N-acetylpyrrol-2-yl, 3-hydroxy-2-pyridyl, 3-methoxy-2-pyridyl, 4-methoxy-2-pyridyl, 4-pyrimidinyl, 2-pyrimidinyl, 2-pyrazinyl, and $R^{18}$ is H or $CH_3CO$. Particularly preferred values for the carboxy protecting group, $R^a$, are allyl, benzyl, t-butyl and 2,2,2-trichloroethyl and especially preferred is allyl because of the relative ease by which it is selectively prepared and removed.

Particularly preferred as the residue of an ester group readily hydrolyzable in vivo, i.e. $R^b$ as defined above are

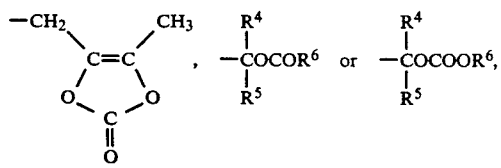

and especially those wherein $R^4$ and $R^5$ are each hydrogen or $R^4$ is H and $R^5$ is $CH_3$, and $R^6$ is as previously defined.

Particularly preferred species of formula (I) include:
1,1-dioxo-6(E)-(2-pyridyl)methylenepenicillanic acid,
1,1-dioxo-6(E)-(2-thiazolyl)methylenepenicillanic acid,
1,1-dioxo-6(E)-(3-isothiazolyl)methylenepenicillanic acid,
1,1-dioxo-6-(3-allyloxy-2-pyridyl)methylenepenicillanic acid,
1,1-dioxo-6-(2-pyrazinyl)methylenepenicillanic acid,
1,1-dioxo-6-(2-pyrimidinyl)methylenepenicillanic acid,
1,1-dioxo-6-(3-hydroxy-2-pyridyl)penicillanic acid, and
1,1-dioxo-6-(4-methoxy-2-pyridyl)penicillanic acid.

Particularly preferred species of formula (II) include:
1,1-dioxo-6-[(2-thiazolyl)acetoxy)]methylpenicillanic acid,
(6 beta, 8S)-6-[(1-methyl-2-benzimidazolyl)(hydroxy)]methylpenicillanic acid,
(6 beta, 8S)-6-[(1-ethyl-2-benzimidazolyl)(hydroxy)]methylpenicillanic acid,
(6 beta, 8S)-6-[(2-benzothiazolyl)(hydroxy)]methylpenicillanic acid, and
6-(2-thiazolyl)hydroxymethylpenicillanic acid.

In addition to providing procedures for making the compounds of formula (I) and (II), the invention further provides a method of treating a bacterial infection in a mammalian subject, including a human, which comprises administering to a mammal in need of such treatment an antibacterially effective amount of a compound of formula (I) wherein $R^1$ is $R^b$ as defined above.

Also provided are pharmaceutical compositions for treating a bacterial infection in mammals, including humans, which comprises an antibacterially effective amount of a compound of formula (I) wherein $R^1$ is $R^b$.

The compounds of the formulae (I) and (II) wherein $R^1$ is $R^b$ as defined above are useful as inhibitors of beta-lactamase enzymes. By this mechanism, these compounds enhance the activity of beta-lactam antibiotics (penicillins and cephalosporins), particularly against those microorganisms which are resistant or partially resistant to the beta-lactam antibiotic through the production of enzymes (beta-lactamases) which would otherwise destroy or partially destroy the beta-lactam antibiotic. In this manner, the spectrum of activity of the beta-lactam antibiotic is increased.

Still further this invention provides a method of treating a bacterial infection in a mammalian subject, including a human, which comprises administering to a mammal in need of such treatment an antibacterially effective amount of a penicillin or cephalosporin, especially those enumerated below, and a beta-lactamase inhibiting amount of a compound of formula (I) or (II).

While the present compounds are effective in enhancing the activity of beta-lactam antibiotics in general, their preferred use is found in their combination with a penicillin or cephalosporin of established clinical utility, viz., amoxicillin, ampicillin, apalcillin, azlocillin, azthreonam, bacampicillin, carbenicillin, carbenicillin indanyl, carbenicillin phenyl, cefaclor, cefadroxil, cefaloram, cefamandole, cefamandole nafate, cefaparole cefatrizine cefazolin cefbuperazone, cefonicid, cefmenoxime, cefodizime, cefoperazone, ceforanide, cefotaxime, cefotiam, cefoxitin, cefpiramide, cefpirome, cefsulodin, ceftazidime, ceftizoxime, ceftriaxone, cefuroxime, cephacetrile, cephalexin, cephaloglycin, cephaloridine, cephalothin, cephapirin, cephradine, cyclacillin, epicillin, furazlocillin, hetacillin, lenampicillin, levopropylcillin, mecillinam, mezlocillin, penicillin G, penicillin V, phenethicillin, piperacillin, pirbenicillin, pivampicillin, sarmoxicillin, sarpicillin, suncillin, talampicillin and ticarcillin, including the pharmaceutically acceptable salts thereof. The names employed for these beta-lactams are generally USAN, i.e., United States Adopted Names.

Also included are combinations of the beta-lactamase inhibitors of the invention with 7-[2-(2-amino-4-thiazolyl)-2methoxyiminoacetamido]-3-(5,6-dihydro-4-pyrindenium)methyl-3-cephem-4-carboxylate (HR-810); 7-[2-(2-amino-4-thiazolyl)-2-methoxyiminoacetamido]-3-(N-methylpyrrolidinium)methyl-3-cephem-4-carboxylate (BMY-28,142) and 7-[D-(2-[4-carboxy-5-imidazolcarboxamido])-2-phenylacetamido]-3-[4-(2-sulfonatoethyl)pyridinium]-3-cephem-4-carboxylic acid.

Although the compounds of the present invention can be administered separately from the beta-lactam antibiotic, combination dosage forms are preferred. The pharmaceutical composition, whether for oral or parenteral use, comprises in a ratio of 1:3 to 3:1 by weight a beta-lactamase inhibitor of the formula (I) or (II) and a beta-lactam antibiotic, in total amounts sufficient to successfully treat a bacterial infection in a mammal in a single or, more usually, multiple doses.

The invention compounds of formulae (I) and (II) wherein one of the groups $R^2$, $R^3$, $R^{12}$ or $R^{13}$ contain a basic nitrogen atom are capable of forming acid addition salts. Such salts with pharmaceutically acceptable acids are included in the invention. Examples of such acids are hydrochloric, hydrobromic, sulfuric, phosphoric, citric, malic, tartaric, maleic, fumaric, gluconic, saccharic, benzenesulfonic, p-toluenesulfonic, p-chlorobenzenesulfonic and 2-naphthalenesulfonic acids.

Further, the compounds of formulae (I) and (II) wherein $R^1$ is hydrogen form cationic salts and such salts with pharmaceutically acceptable cations are included in the invention. Examples of such cations are sodium, potassium, ammonium, calcium, magnesium, zinc; and substituted ammonium salts formed with amines such as diethanolamine, choline, ethylenediamine, ethanolamine, N-methylglucamine and procaine.

DETAILED DESCRIPTION OF THE INVENTION

This invention relates to derivatives of penicillanic acid which is represented by the following structural formula:

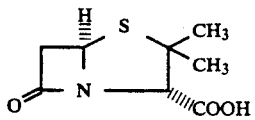

In derivatives of penicillanic acid, broken line attachment (⊪⊪⊪⊪⊪⊪) of a substituent to the bicyclic nucleus indicates that the substituent is below the plane of the nucleus. Such a substituent is said to be in the alpha-configuration. Conversely, broad line attachment ( ◂▬▬ ) of a substituent to the bicyclic nucleus indicates that the substituent is above the plane of the nucleus. This latter configuration is referred to as the beta-configuration. As used herein a solid line attachment (-) of a substituent to the bicyclic nucleus indicates that the substituent can be in either the alpha-configuration or the beta-configuration.

Due to the carbon-carbon double bond at the 6-position, the compounds of formula (I) exist as geometric isomers having either the E- or Z-configuration. As defined herein, a compound of formula (I) is said to have the E-configuration if the substituent $R^2$ or $R^3$ which is other than hydrogen is opposite the carbonyl group of the beta-lactam ring. Conversely, a compound of formula (I) is said to have the Z-configuration if the substituent $R^2$ or $R^3$ which is other than hydrogen is toward the carbonyl group of the beta-lactam ring.

The compounds of the invention are prepared for example, by one or more of the following general methods.

Method A

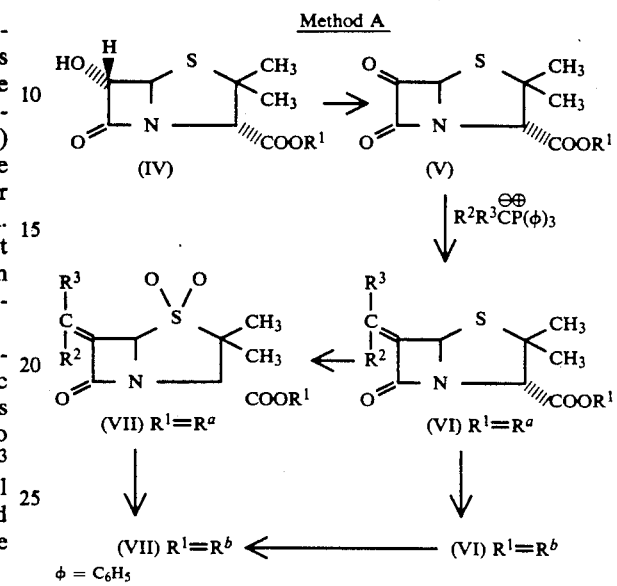

Method B

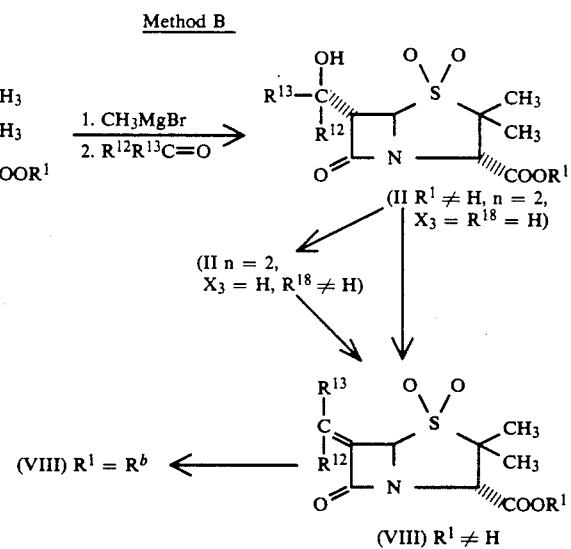

Method C

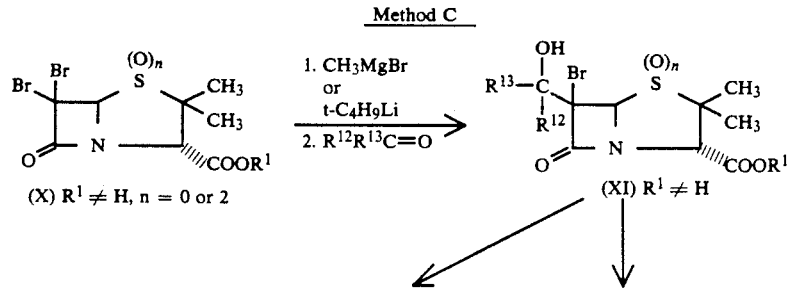

Method C

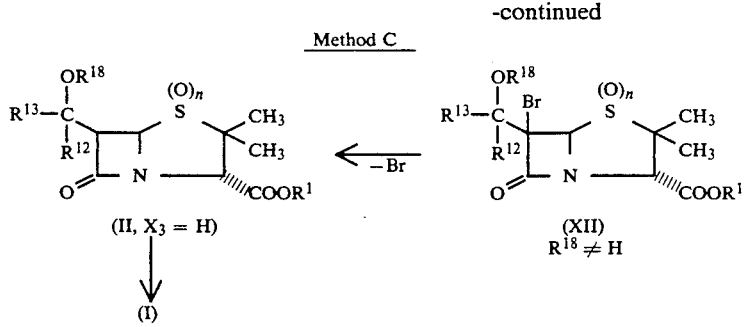

The requisite Wittig salts of the formula $$R^2R^3CHP(C_6H_5)_3Cl^\ominus$$

employed in Method A, above, are either known compounds or are readily prepared from commercially available precursors by common synthetic methods, for example as illustrated below.

Preparation of Wittig Salts

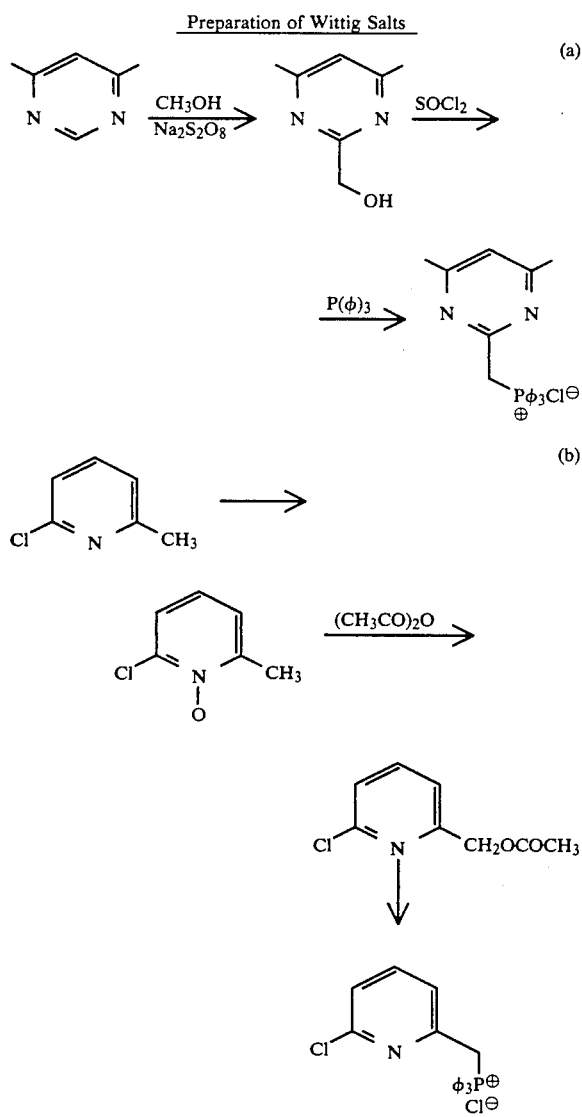

(a)

(b)

-continued
Preparation of Wittig Salts

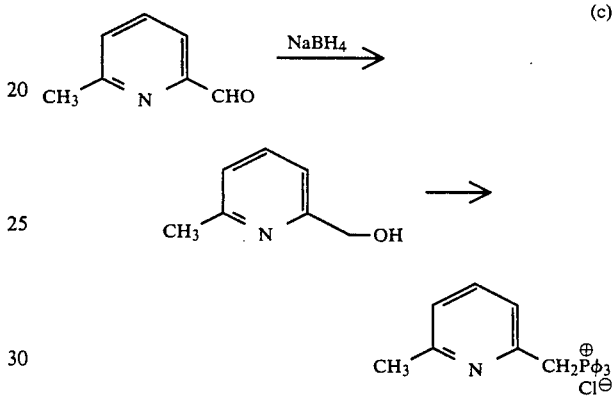

(c)

The primary alcohols of the general formula $R^3CH_2OH$ are converted to the corresponding chloromethyl compounds, typically by reacting the alcohol with an equimolar amount of thionyl chloride in the presence of a reaction inert solvent, e.g. chloroform or methylene chloride at or about room temperature. The product is isolated, e.g., by neutralization of the reaction mixture and extraction.

The chloromethyl compound, $R^3CH_2Cl$ is then converted to the desired Wittig salt e.g. by reaction with an equimolar amount of triphenylphosphine. Typically, this step is carried out in a solvent such as toluene at elevated temperature, preferably at the reflux temperature. The desired product forms a precipitate which is then collected by filtration.

6-Alpha-hydroxypenicillanic acid is a known compound, see e.g., Hauser et al., Helv. Chim. Acta, 50, 1327 (1967). The acid is converted to a carboxy protected derivative of the formula (IV) The identity of the carboxy protecting group is not critical. The only requirements for the carboxy protecting group $R^a$ are that: (i) it must be stable to oxidation conditions employed to form the 6-oxopenicillanate ester (V) and its subsequent reaction with the Wittig reagent to form the 6-(substituted)methylenepenicillanate of formula (VI, $R^1=R^a$); (ii) it must be selectively removable from the compound of formula (VI, $R^1=R^a$) using conditions under which both the beta-lactam and the 6-(substituted)-methylene groups remain substantially intact; (iii) it must be stable to oxidation of the compound (VI, $R^1=R^a$) to form the sulfones of formula (VII) or the corresponding sulfoxides. Typical such carboxy protecting groups which meet the above requirements are the tetrahydropyranyl group, the benzyl group, the benzhydryl group, the 2,2,2-trichloroethyl group, the allyl group, the t-butyl group and the phenacyl group.

See further: U.S. Pat. Nos. 3,632,850 and 3,197,466; British Patent No. 1,041,985, Woodward et al., *Journal of the American Chemical Society*, 88, 852 (1966); Chauvette, *Journal of Organic Chemistry*, 36, 1259 (1971); Sheehan et al., *Journal of Organic Chemistry*, 29, 2006 (1964); and "Cephalosporin and Penicillins, Chemistry and Biology", edited by H. E. Flynn, Academic Press, Inc., 1972. Particularly preferred such groups are allyl, benzyl and 2,2,2-trichloroethyl and especially preferred is allyl because of its ease of preparation and selective removal.

The oxidation of the carboxy protected 6-alphahydroxypenicillanate (IV) to the corresponding 6-oxopenicillanate ester (X) is typically carried out with an approximately equimolar amount of trifluoroacetic anhydride and a molar excess of dimethylsulfoxide in the presence of a reaction inert solvent, e.g., chloroform or methylene chloride The reaction is preferably carried out at a temperature of from about $-80°$ to $-70°$ C. The reaction mixture is neutralized, e.g. by addition of a tertiary amine such as triethylamine, after which the mixture is isolated, e.g. by partitioning between water and a water immiscible solvent and evaporation of the organic layer.

The 6-oxopenicillanate ester of formula (V) is then reacted with a Wittig reagent of formula

$$R^2R^3\overset{\ominus\oplus}{C}P(C_6H_5)_3.$$

This reaction is preferably carried out in the presence of a reaction inert organic solvent, for example, a hydrocarbon such as pentane, hexane, benzene, toluene or xylene; a halogenated hydrocarbon such as methylene chloride, chloroform, carbon tetrachloride, 1,2-dichloroethane, 1,2-dibromoethane or chlorobenzene; an ether such as tetrahydrofuran, dioxane, diethyl ether, 1,2-dimethoxyethane or t-butylmethylether. While this reaction can be carried out over a range of temperature of from about $-100°$ to $+50°$ C., a preferred temperature is in the range of about $-78°$ to $25°$ C.

The desired product of formula (VI, $R^1=R^a$) is isolated by known techniques, for example, the reaction is quenched by addition of aqueous ammonium chloride, extraction with a water immiscible solvent and the solvent evaporated. The resulting product is purified, if desired, by conventional methods known to those of skill in the art, for example, by column chromatography on silica gel.

The ester of formula (VI, $R^1=R^a$) where $R^a$ is a carboxy protecting group as defined above can then be converted to the corresponding acid or ester of formula (VI, $R^1=R^b$) where $R^b$ is hydrogen or an ester forming residue readily hydrolyzable in vivo. Typically, the carboxy protecting group is removed from the intermediate compound of formula (VI, $R^1=R^a$) to form the corresponding carboxylic acid. The specific method chosen for removal of the carboxy protecting group will depend upon the precise nature of the ester residue $R^a$, but an appropriate method will be readily recognized to one of skill in the art.

As mentioned above, an especially preferred carboxy protecting group, $R^a$, is allyl. While this group can be removed by mild acid or alkaline hydrolysis procedures with satisfactory results, an especially preferred method for its removal employs a soluble palladium (O) complex, tetrakis (triphenylphosphine)palladium (O) as a catalyst, a method previously reported by Jeffrey and McCombie, *J. Org. Chem.*, 47, 587–590 (1982). In a typical procedure the allyl ester in reaction inert solvent, e.g. ethylene dichloride, chloroform, ethyl acetate, and a catalytic amount of tetrakis (triphenylphosphine)palladium (O), for example from about 1 to 5 mole percent based on the allyl ester, and an approximately equal weight of triphenylphosphine are combined under a nitrogen atmosphere. To this is added a sodium or potassium salt of 2-ethylhexanoate in an amount equimolar to the starting allyl ester and the resulting mixture is stirred at ambient temperature until precipitation of the desired salt, e.g. of formula (VI) where $R^1$ is Na or K, is complete. Usually the reaction is substantially complete in from about two to twenty hours. The salt is then collected, e.g. by filtration.

When sulfoxides or sulfones of the invention are desired, for example those of the formulae (I) wherein n is 1 or 2, the sulfides of formula (VI) are oxidized employing any of a wide variety of oxidants known in the art for the oxidation of sulfoxides to sulfones. However, particularly convenient reagents are metal permanganates, such as the alkali metal permanganates and the alkaline earth metal permanganates, and organic peroxy acids, such as organic peroxycarboxylic acids. Convenient individual reagents are sodium permanganate, potassium permanganate, 3-chloroperbenzoic acid and peracetic acid.

A particularly preferred group of oxidants are the organic peroxy acids and a preferred organic peroxy acid is 3-chloroperbenzoic acid.

When the desired oxidation product is a sulfoxide of formula (I) wherein n is 1, approximately molar equivalents of the starting sulfide (n is zero) and oxidant are employed. When the desired product is a sulfone, e.g. of formula (I) where n is 2, the sulfide is contacted with two or more molar equivalents of oxidant. Alternately, of course, the sulfoxides can serve as starting materials for the preparation of the corresponding sulfone, in which case at least an approximately equimolar amount of oxidant is employed.

When, for example, a compound of the formula (VI, $R^1=R^a$), wherein $R^a$ is as previously defined, is oxidized to the corresponding compound of the formula (VII), using an organic peroxy acid, e.g., a peroxycarboxylic acid, the reaction is usually carried out by treating the compound of the formula (VI, $R^1=R^a$) with from about 2 to about 4 molar equivalents of the oxidant in a reaction-inert organic solvent. Typical solvents are chlorinated hydrocarbons, such as dichloromethane, chloroform and 1,2-dichloroethane; and ethers, such as diethyl ether, tetrahydrofuran and 1,2-dimethoxyethane. The reaction is normally carried out at a temperature of from about $-20°$ to about $50°$ C., and preferably at about $25°$ C. At about $25°$ C. reaction times of about 2 to about 16 hours are commonly used. The product is normally isolated by removal of the solvent by evaporation in vacuo. The product can be purified by conventional methods, well-known in the art.

In the above-mentioned oxidation procedures it is preferred to employ a starting material wherein the carboxy group is protected by the above-mentioned carboxy protecting groups, $R^a$. The removal of the carboxy protecting group from its product sulfoxide or sulfone is carried out in the normal manner for the particular protecting group being used, for example as described above for the compounds (VI, $R^1=R^a$).

The compounds of the invention, e.g. of formula (I) or (II), wherein $R^1$ is an ester forming residue readily hydrolyzable in vivo can be prepared directly from the corresponding compound where $R^1$ is hydrogen, by conventional esterification techniques. The specific method chosen will depend upon the precise structure of the ester forming residue, but an appropriate method will be readily selected by one skilled in the art. In the case where $R^1$ is selected from 3-phthalidyl, 4-crotonolactonyl, gamma-butyrolacton-4-yl and groups of the formulae

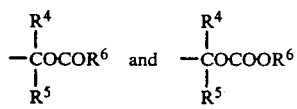

wherein $R^4$, $R^5$ and $R^6$ are as previously defined, they can be prepared by alkylation of the appropriate invention compound wherein $R^1$ is hydrogen with a halide of the formula $R^bQ$, that is a 3-phthalidyl halide, a 4-crotonolactonyl halide, a gamma-butyrolacton-4-yl halide or a compound of the formula

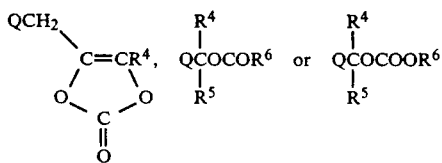

wherein Q is halo and $R^4$, $R^5$ and $R^6$ are as previously defined. The terms "halide" and "halo" are intended to mean derivatives of chlorine, bromine and iodine. The reaction is typically carried out by dissolving a salt of the compound of e.g., formula (I) or (II) wherein $R^1$ is hydrogen in a suitable polar organic solvent, for example, N,N-dimethylformamide, and then adding about one molar equivalent of the appropriate halide ($R^bQ$). When the reaction has proceeded essentially to completion, the product is isolated by standard techniques. It is often sufficient simply to dilute the reaction medium with an excess of water, and then extract the product into a water-immiscible organic solvent and then recover same by solvent evaporation. Salts of the starting material which are commonly used are alkali metal salts, such as sodium and potassium salts, tertiary amine salts, such as triethylamine, N-ethylpiperidine, N,N-dimethylaniline and N-methylmorpholine salts and quaternary ammonium salts, such as tetramethylammonium and tetrabutylammonium salts. The reaction is run at a temperature in the range from about 0° to 100° C., and usually at about 25° C. The length of time needed to reach completion varies according to a variety of factors, such as the concentration of the reactants and the reactivity of the reagents. Thus, when considering the halo compound, the iodide reacts faster than the bromide, which in turn reacts faster than the chloride. In fact, it is sometimes advantageous, when utilizing a chloro compound, to add up to one molar equivalent of an alkali metal iodide. This has the effect of speeding up the reaction. With full regard for the foregoing factors, reaction times of from about 1 to about 24 hours are commonly used.

When Method B as outlined above is employed to prepare the invention compounds of formula (II) where n is 2 and $X_3$ and $R^{18}$ are each hydrogen or compounds of formula (VIII), the requisite 6-alpha-bromo-1,1-dioxopenicillanate ester starting material (IX) is converted to a Grignard reagent by reaction with an equimolar amount of a low molecular weight Grignard reagent, e.g., methylmagnesium bromide, ethylmagnesium chloride or n-butylmagnesium iodide, in an ethereal solvent, preferably tetrahydrofuran or ethyl ether, or in benzene, toluene or methylene chloride as solvent, at a temperature of from −80° to 25° C., typically −78° C. After stirring for a few minutes, an equimolar amount of the appropriate aldehyde of formula $R^{12}R^{13}C=O$ is added and stirring continued until the reaction is substantially complete, ordinarily from about 10 minutes to about four hours at the same temperature. The desired ester of formula (II), n=2, is then isolated by standard methods. For example, the reaction is quenched with aqueous ammonium chloride and the product extracted with a water immiscible solvent. The resulting product, (II), is further purified, e.g., by silica gel chromatography.

The secondary alcohol of formula (II), n=2, $X_3$=H, can then be dehydrated to provide the corresponding 6-(substituted)methylene-1,1-dioxopenicillanate compound of formula (VIII). While a variety of methods known in the art for dehydration of secondary alcohols to olefins may be employed to successfully carry out this step, a preferred method employs conversion of the alcohol to an acetate by reaction with at least equimolar amounts of acetic anhydride and pyridine followed by stirring at room temperature for from one to ten hours to allow for formation of olefin in substantial amounts. The reaction is ordinarily quenched with water and the desired product (II), n=2, is isolated by extraction methods and purified, if desired.

The products of formula (II), or (VIII) obtained as described above are esters wherein $R^1$ is either a carboxy protecting group, $R^a$, as defined above or is the residue of an ester group readily hydrolyzable in vivo, $R^b$, as defined above These esters wherein $R^1$ is $R^a$ are converted into the corresponding carboxylic acids ($R^b$ is hydrogen) by methods described above. Of course, when desired, the carboxylic acids of formula (II) and (VIII) are converted to a corresponding compound wherein $R^1$ is the residue of an ester group readily hydrolyzable in vivo, by methods also described above.

Typically, the starting 6-alpha-bromo-1,1-dioxopenicillanate esters (IX) are prepared from the 6,6-dibromo-1,1-dioxopenicillanic acid by treatment with sodium bicarbonate and sodium bisulfite followed by acidification. The resulting 6-alpha-bromo-1,1-dioxopenicillanic acid is then converted to an ester of formula (IX).

The starting esters of formula (X) employed in Method C as outlined above, are known compounds, see, e.g. U.S. Pat. No. 4,234,579. In a typical procedure carried out by this method, the starting ester (X) in reaction inert solvent, e.g. toluene, xylene, pentane, tetrahydrofuran, ethyl ether or mixtures thereof, is contacted at low temperature with an equimolar amount of alkyl lithium reagent, e.g., n-butyl lithium, t-butyl lithium or methyl lithium, to form a lithiopenicillin intermediate. This is immediately contacted with an equimolar amount of aldehyde, $R^{12}R^{13}CO$, where $R^{12}R^{13}$ are as previously defined, and the mixture stirred at −100° to −50° C., preferable −78° C., for about 1-4 hours. The reaction is then quenched and the bromohydrin intermediate of formula (XI) isolated, for example, by partitioning between water and solvent and purification of the extract by column chromatography on silica gel or Florisil (magnesium silicate).

Alternatively, the above starting dibromo ester of formula (X) is reacted with an equimolar amount of a low molecular weight Grignard reagent, employing the same reagents and conditions described above for Method B, to provide the bromohydrin of formula (XI).

The bromohydrin (XI) can be acylated to provide the corresponding compound (XII) wherein $R^{18}$ is other than hydrogen as defined above. Typically the acylation is carried out by reaction of equimolar amounts of acyl chloride, acyl bromide or the corresponding acid anhydride, the intermediate bromohydrin of formula (XI) and a tertiary amine, for example pyridine, N-methylmorpholine or the like, in the presence of a reaction inert organic solvent, preferably methylene chloride, tetrahydrofuran or ethyl acetate at or below room temperature. The desired diester of formula (XII) is then isolated by well-known methods such as extraction and evaporation of solvent and purified, if desired, e.g. by column chromatography.

The bromohydrin ester intermediate (XI) or the bromo diester (XII) can then be subjected to hydrogenolysis conditions to remove the bromine atom. This is accomplished by employing any of a variety of the known reducing agents and conditions such as, e.g. subjecting the bromohydrin to hydrogen in the presence of a noble metal catalyst or to reduction by means of certain organotin hydrides.

Preferred organotin hydride reducing agents are the dialkyltin dihydrides, trialkyltin hydrides, having from one to six carbon atoms in each of said alkyl groups, and the triaryltin hydrides wherein said aryl is phenyl, or phenyl substituted by nitro or alkyl or alkoxy having from one to three carbon atoms. Particularly preferred are triphenyltin hydride and tri-n-butyltin hydride, the latter being especially preferred for reasons of economy and efficiency.

The reaction employing said tin hydrides is ordinarily carried out in the presence of a reaction inert solvent. Suitable solvents for use with the organotin hydride reducing agents are those which substantially dissolve the starting compound of formula (XI) or (XII) but do not themselves react with the hydride reducing agent. Examples of such solvents include the aromatic hydrocarbons such as benzene, toluene, xylene, chlorobenzene and napthalene; and ethers such as ethyl ether, isopropyl ether, tetrahydrofuran, dioxane and 1,2-dimethoxyethane. Particularly preferred solvents for reasons of economy and efficiency are benzene and toluene.

In carrying out the hydrogenolysis employing organotin hydride reducing agents, equimolar amounts of bromohydrin (XI) or bromodiester (XII) and hydride is required by theory. In practice an excess of hydride, e.g., 5–50% molar excess, is often employed to assure complete reaction.

The hydrogenolysis by organotin hydrides proceeds to substantial completion under the preferred conditions disclosed above without use of a catalyst. However, the reaction is expedited by means of a source of free radicals such as, e.g., ultraviolet light, or a catalytic amount of azobisisobutyronitrile or peroxides such as benzoyl peroxide A catalytic amount of azobisisobutyronitrile is a preferred source of free radicals for this reaction.

Typically, the compound of formula (XI) or (XII) is dissolved in reaction inert solvent, the solution is maintained under an inert atmosphere, e.g. a nitrogen or argon atmosphere, and the appropriate amount of organotin hydride and, optionally, the source of free radicals, e.g. azobisisobutyronitrile, added and the resulting mixture stirred at a temperature within the preferred range of from about 0° C. up to the boiling point of the solvent. The reaction is ordinarily complete in from a few minutes to about a few hours, e.g., from 5 minutes at the boiling point of benzene to about 20 hours at 0° C. The product of formula (II, $X_3$=H) is then isolated by methods known to those of skill in the art. For example, by evaporation of solvent and silica gel chromatography of the residue.

The compounds of formula (II, $X_3$=H) formed by organotin hydride debromination as described above, have been found to be predominantly the 6-beta isomers, that is, the 6-$R^{12}R^{13}C(OR^{18})$ substituent is in the beta-configuration.

When the hydrogenolysis step is carried out employing hydrogen in the presence of a noble metal catalyst, a convenient method for carrying out this transformation is to stir or shake a solution of a compound of the formula (XI) or (XII) under an atmosphere of hydrogen, or hydrogen mixed with an inert diluent such as nitrogen or argon, in the presence of a noble metal hydrogenolysis catalyst. Suitable solvents for this hydrogenolysis reaction are those which substantially dissolve the starting compound of the formula (XI) or (XII) but which do not themselves suffer hydrogenation or hydrogenolysis. Examples of such solvents include ethers such as diethyl ether, tetrahydrofuran, dioxane and 1,2-dimethoxyethane; low molecular weight esters such as ethyl acetate and butyl acetate; tertiary amides such as N,N-dimethylformamide, N,N-dimethylacetamide and N-methylpyrrolidone; water; and mixtures thereof. Additionally, it is often desirable to buffer the reaction mixture so as to operate at a pH in the range from about 4 to 9, and preferably from about 6 to 8. Borate, bicarbonate and phosphate buffers are commonly used. Introduction of the hydrogen gas into the reaction medium is usually accomplished by carrying out the reaction in a sealed vessel, containing the compound of formula (XI) or (XII), the solvent, the catalyst and the hydrogen. The pressure inside the reaction vessel can vary from about 1 to about 100 kg./cm.$^2$. The preferred pressure range, when the atmosphere inside the reaction vessel is substantially pure hydrogen, is from about 2 to about 5 kg./cm.$^2$. The hydrogenolysis is generally run at a temperature of from about 0° to about 60° C., and preferably from about 25° to about 50° C. Utilizing the preferred temperature and pressure values, hydrogenolysis generally takes place in a few hours, e.g., from about 2 hours to about 20 hours. The preferred noble metal catalysts used in this hydrogenolysis reaction are the type of agents known in the art for this kind of transformation, for example, nickel, palladium, platinum and rhodium. Palladium is particularly preferred. The catalyst is usually present in an amount from about 0.01 to about 25 weight-percent, and preferably from about 0.1 to about 10 weight-percent, based on the compound of formula (XI). It is often convenient to suspend the catalyst on an inert support; a particularly convenient catalyst is palladium suspended on an inert support such as carbon.

When the hydrogenolysis is substantially complete, the desired product of formula (II, $X_3$=H) is then isolated by standard methods, e.g., the catalyst is removed by filtration, the solvent evaporated and the product purified, if desired, by well known methods such as crystallization or by chromatography.

When the starting compound of formula (XI) or (XII) is a benzyl ester ($R^1=R^a=$benzyl), the above catalytic hydrogenolysis procedure can also cause cleavage of the benzyl group, and the product is of formula (II) where $X_3$ and $R^1$ are each hydrogen.

The 6-(substituted)hydroxymethylpenicillanic acid or ester of formula (XII) or (II, $X_3=$H) where n is zero, can be oxidized by any of the methods known to convert sulfides to sulfoxides and sulfones, for example by means of 3-chloroperbenzoic acid as described above, to provide the corresponding sulfoxide or sulfone of formula (XII) OR (II, $X_3=$H) and where in each n is 1 or 2, respectively. However, a preferred method for obtaining sulfones of formula (XI), (XII) or (II) is by employing the appropriate 6,6-dibromo-1,1-dioxopenicillanate ester (X) where n=2 as starting material in the above described Method C.

The starting aldehydes of formula $R^{12}R^{13}CO$ wherein $R^{12}$ and $R^{13}$ are as defined above are either available from a commercial source or are readily prepared from available starting materials by methods well known in the art, e.g.

1. Oxidation of the corresponding primary alcohols provided above as Wittig reagent precursors employing e.g. oxidants such as potassium dichromate, chromic acid/pyridine, catalytic oxidation in the presence of noble metals, manganese dioxide.
2. Reaction of the corresponding methyl substituted aromatic hydrocarbon with e.g. selenium dioxide.
3. Metal hydride reduction of the corresponding $C_1$-$C_4$ compound at low temperature in the presence of ethereal solvents. Examples of suitable metal hydrides are lithium aluminum hydride and diisobutylaluminum hydride (DIBAL-H).
4. Reaction of an appropriate aromatic hydrocarbon precursor with n-butyl lithium and dimethylformamide.

As indicated above, the compounds of the formulae (I) or (II) wherein $R^1$ is H, and salts thereof, in combinations with beta-lactam antibiotics, show synergistic activity in in vitro antibacterial tests. Such activity is demonstrated by measuring the minimum inhibitory concentrations (MIC's) in mcg/ml against a variety of microorganisms. The procedure which is followed is the one recommended by the International Collaborative Study on Antibiotic Sensitivity Testing (Ericcson and Sherris, *Acta. Pathologica et Microbiologia Scandinav*, Supp 217, Section B: 64–68 [1971]), and employs brain heart infusion (BHI) agar and the inocula replicating device. Overnight growth tubes are diluted 100 fold for use as the standard inoculum (20,000–10,000 cells in approximately 0.002 ml are placed on the agar surface; 20 ml of BHI agar/dish). Twelve 2-fold dilutions of the test compound are employed, with initial concentration of the test drug being 200 mcg/ml. Single colonies are disregarded when reading plates after 18 hours at 37° C. The susceptibility (MIC) of the test organism is accepted as the lowest concentration of test compound or combination of compounds capable of producing complete inhibition of growth as judged by the naked eye.

Those compounds of the formulae (I) and (II), where $R^1$ is H, and salts thereof, in combinations with known beta-lactam antibiotics are useful as industrial antimicrobials, for example in water treatment, slime control, paint preservation and wood preservation, as well as for topical application as disinfectants. In the case of use of these compounds for such an application, it is often convenient to admix the active ingredient with a non-toxic carrier, such as vegetable or mineral oil or an emollient cream. Similarly, they can be dissolved or dispersed in liquid diluents or solvents such as water, alkanols, glycols or mixtures thereof. In most instances it is appropriate to employ concentrations of the active ingredient of from about 0.1 percent to about 10 percent by weight, based on total composition.

As also indicated above, the compounds of the formulae (I) and (II) wherein $R^1$ is $R^b$ are of more particular value as potent inhibitors of microbial beta-lactamases. By this mechanism they increase the antibacterial effectiveness of beta-lactam antibiotics (penicillins and cephalosporins) against many micro-organisms, particularly those which produce a beta-lactamase. The ability of the said compounds of the formula (I) or (II) to increase the effectiveness of a beta-lactam antibiotic can be appreciated by reference to experiments in which the MIC values of the antibiotic alone, and a compound of the formula (I) or (II) having $R^1$ as hydrogen alone are determined. These MIC's are then compared with the MIC values obtained with a combination of the given antibiotic and the compound of the formula (I) or (II), wherein $R^1$ is hydrogen. When the antibacterial potency of the combination is significantly greater than would have been predicted from the potencies of the individual compounds, this is considered to constitute enhancement of activity. The MIC values of combinations are measured using the method described by Barry and Sabath in "Manual of Clinical Microbiology", edited by Lenette, Spaulding and Truant, 2nd Edition, 1974, American Society for Microbiology.

The compounds of the formulae (I) and (II) wherein $R^1$ is hydrogen or the residue of an ester group readily hydrolyzable in vivo enhance the antibacterial effectiveness of beta-lactam antibiotics in vivo. That is, they lower the amount of the antibiotic which is needed to protect mice against an otherwise lethal inoculum of certain beta-lactamase producing bacteria. In determining such activity, acute experimental infections are produced in mice by the intraperitoneal inoculation of the mice with a standardized culture of the test organism suspended in 5 percent hog gastric mucin. Infection severity is standarized so that the mice receive a lethal dose of the organism (the lethal dose is the minimum inoculum of organism required to consistently kill 100 percent of the infected, non-treated control mice). The test compound in combination with the antibiotic is administered at various dosage levels, p.o. or i.p., to groups of infected mice. At the end of the test, the activity of the mixture is assessed by counting the number of survivors among treated animals at a given dose. Activity is expressed as the percentage of animals which survive at a given dose, or calculated as a $PD_{50}$ (dose which protects 50% of the animals from infection).

The ability of said compounds of formulae (I) and (II) to enhance the effectiveness of a beta-lactam antibiotic against beta-lactamase producing bacteria makes them valuable for co-administration with beta-lactam antibiotics in the treatment of bacterial infections in mammals, particularly man. In the treatment of a bacterial infection, the compound of the formula (I) or (II) can be co-mingled with the beta-lactam antibiotic, or in the case where $R^b$ is $CH(R^4)OCOR^{14}$ where $R^4$ and $R^{14}$ are as defined above, the beta-lactam antibiotic is chemically linked to the compound of formula (I) or (II), and the two agents thereby administered simultaneously.

Alternatively, the compound of the formula (I) or (II) can be administered as a separate agent during a course of treatment with a beta-lactam antibiotic. In some instances it will be advantageous to pre-dose the subject with the compound of the formula (I) or (II) before initiating treatment with a beta-lactam antibiotic.

When using a compound of formula (I) or (II) wherein $R^1$ is $R^b$ as defined above to enhance the effectiveness of a beta-lactam antibiotic, a mixture of said compound with the beta-lactam antibiotic, or the invention compound alone when $R^b$ is $CH(R^4)OCOR^{14}$, is administered preferably in formulation with standard pharmaceutical carriers or diluents. A pharmaceutical composition comprising a pharmaceutically acceptable carrier, a beta-lactam antibiotic and/or said compound of formula (I) or (II) will normally contain from about 5 to about 80 percent of the pharmaceutically acceptable carrier by weight.

When using said compounds of formula (I) or (II) in combination with another beta-lactam antibiotic, said compounds can be administered orally or parenterally, i.e. intramuscularly, subcutaneously or intraperitoneally. Although the prescribing physician will ultimately decide the dosage to be used in a human subject, the ratio of the daily dosages of the compound of formula (I) or (II), wherein $R^1$ is $R^b$, and the beta-lactam antibiotic will normally be in the range from about 1:3 to 3:1 by weight. Additionally, when using the compounds of formula (I) or (II) in combination with a beta-lactam antibiotic, the daily oral dosage of each component will normally be in the range from about 10 to about 200 mg per kilogram of body weight and the daily parenteral dosage of each component will normally be about 10 to about 40 mg per kilogram of body weight. These daily doses will usually be divided. In some instances, the prescribing physician will determine that dosages outside these limits are necessary.

As will be appreciated by one skilled in the art, some beta-lactam compounds are effective when administered orally or parenterally, while others are effective only when administered by the parenteral route. When a compound of formula (I) or (II) is to be used simultaneously (i.e. co-mingled) with a beta-lactam antibiotic which is effective only on parenteral administration, a combination formulation suitable for parenteral use will be required. When a compound of formula (I) or (II) is to be used simultaneously (co-mingled) with a beta-lactam antibiotic which is effective orally or parenterally, combinations suitable for either oral or parenteral administration can be prepared. Additionally, it is possible to administer preparations of the active compounds of formula (I) or (II) orally, while at the same time administering a further beta-lactam antibiotic parenterally; and it is also possible to administer preparations of said compounds of formula (I) or (II) parenterally, while at the same time administering the further beta-lactam antibiotic orally.

The present invention is illustrated by the following examples. However, it should be understood that the invention is not limited to the specific details of these examples. Proton and $C^{13}$ nuclear magnetic resonance spectra were measured at 60, 90, 250 or 300 MHz for solutions in deuterochloroform ($CDCl_3$), deuterium oxide ($D_2O$), perdeutero acetone ($CD_3COCD_3$) or perdeutero dimethyl sulfoxide (DMSO-$d_6$) and peak positions are expressed in parts per million (ppm) downfield from tetramethylsilane. The following abbreviations are used: s, singlet; d, doublet; dd, doublet of doublets; t, triplet; q, quartet; m, multiplet; b, broad.

EXAMPLE 1

6-alpha-Hydroxypenicillanate Esters

A. Allyl ester

A solution of 85 g 6-alpha-hydroxypenicillanic acid* (0.39 mole) in 300 ml dimethylformamide was treated with 34 mil (0.39 mole) allyl bromide, 54 ml (0.39 mole) triethylamine and 2 g sodium bicarbonate and the mixture stirred at room temperature for 15 hours. After quenching the reaction with water and extraction with ethyl ether, the combined ether layers were washed with saturated sodium bicarbonate solution, water, dried (MgSO$_4$) and concentrated in vacuo to afford 43 g of crude product. The crude material was purified by silica gel column chromatography, eluting with 9:1 chloroform/ethyl acetate to yield 22.75 g (23%) of the allyl ester. $^1$H-NMR(CDCl$_3$)ppm (delta): 1.42 (s, 3H), 1.60 (s, 3H), 4.45 (s, 1H), 4.5–5.0 (m, 3H), 5.2–6.2 (m, 4H).

*Prepared by the method of Hauser et al., Helv. Chim. Acta, 50, 1327 (1967).

B. Pivaloyloxymethyl ester

A mixture of 9 g (0.041 mole) 6-alpha-hydroxypenicillanic acid, 40 ml dimethylformamide, 7.4 ml (0.041 mole) diisopropylethylamine, 6 ml (0.041 mole) chloromethyl pivalate and 6.15 g (0.041 mole) sodium iodide was stirred at room temperature for 15 hours. Water was added, the mixture extracted with ethyl ether, the extracts dried and concentrated to give 9 g of crude ester which was purified on a silica gel golumn, eluting with chloroform/ethyl acetate (9:1). The combined produce fractions amounted to 4.38 g (32%).

C. Benzyl ester

To a mixture of 20 g (0.092 mole) 6-alpha-hydroxypenicillanic acid, 12.9 ml (0.092 mole) triethylamine, 1.105 g (0 013 mole) sodium bicarbonate and 200 ml dimethylformamide (DMF) was added 12.0 ml (0.101 mole) benzyl bromide. The mixture was stirred at room temperature for 20 hours, partitioned between ethyl ether and water and the aqueous phase adjusted to pH 2.0 with 6N hydrochloric acid. The layers were separated, the aqueous layer extracted twice again with ether, the combined ether layers washed with sodium bicarbonate solution, water, dried and the solvent evaporated. The residue was crystallized from hot chloroform/hexane to afford 9.1 g of colorless crystals, m.p. 165°–167° C.

D. (5-Methyl-2-oxo-1,3-dioxol-4-yl)methyl ester

A mixture of 15 g (0.078 mole) (5-methyl-2-oxo-1,3-dioxol-4-yl)methyl bromide, 18.7 g (0.078 mole) sodium 6-alpha-hydroxypenicillanate in 225 ml DMF is stirred at room temperature for 4 hours, poured into ice and worked up as described above to provide the desired ester.

EXAMPLE 2

6-Oxopenicillanate Esters

A. Allyl 6-oxopenicillanate

A mixture of 2.84 ml (0.04 mole) dimethylsulfoxide, 3.67 ml (0.026 mole) trifluoroacetic anhydride and 50 ml methylene chloride was stirred at −78° C. for ten minutes A solution of 5.14 g (0.02 mole) allyl 6-alpha-hydroxypenicillanate in 10 ml methylene chloride was added at −78° C. and the resulting mixture stirred for 40 minutes. Triethylamine (7.24 ml, 0.052 mole) was added at this temperature and the mixture was gradually warmed to room temperature and quenched with water. After extracting with methylene chloride, the combined organic layers were washed with water (3 x), dried and the solvent evaporated in vacuo to give the title compound as a yellow oil, 5.1 g (100%). $^1$H-NMR(CDCl$_3$)ppm (delta): 1.60 (s, 6H), 4.75 (m, 2H), 4.82 (s, 1H), 5.1–6.3 (m, 3H), 5.82 (s, 1H).

B. Pivaloyloxymethyl ester

A mixture of 0.36 ml (5.06 mmole) dimethylsulfoxide, 0.47 ml (3.29 mmole) trifluoroacetic anhydride, 839 mg (2.53 mmole) pivaloyloxymethyl 6-alpha-hydroxypenicillanate and 5 ml methylene chloride was stirred at −78° C. for 30 minutes and 0.92 ml (6.58 mmole) of triethylamine was added. Work-up of the product as described in Part A, above, gave 788 mg (95%) of the desired ketone. $^1$H-NMR(CDCl$_3$)ppm (delta): 1.3 (s, 9H), 1.65 (s, 6H), 4.85 (s, 1H), 5.8 (m, 3H).

EXAMPLE 3

Allyl 6(E)-(2-pyridyl)methylenepenicillanate

A mixture of 2.64 g (6.8 mmole) 2-picolyl triphenylphosphonium chloride and 0.265 g (6.8 mmole) sodium amide in 6 ml dry tetrahydrofuran (THF) was stirred at room temperature for 30 minutes. The resulting brown suspension was cooled to −78° C., a solution of 1.8 g (7.0 mmole) allyl 6-oxopenicillanate in 4 ml dry THF was added in one portion and the mixture stirred at −78° C. for three minutes. The reaction was quenched by addition of saturated ammonium chloride solution, extracted with ethyl acetate and the combined organic layers were washed with water (3 x), dried (MgSO$_4$) and concentrated in vacuo to give 3.3 g of red oil. The oil was purified by chromatography on a silica gel column to yield 1.35 g (60.7%) of the desired product as a yellow oil. $^1$H-NMR(CDCl$_3$)ppm (delta): 1.50 (s, 3H), 1.58 (s, 3H), 4.57 (s, 1H), 4.65 (d, 2H), 5.15–6.15 (m, 3H), 6.17 (d, 1H, J=1Hz), 6.87 (d, 1H, J=1Hz), 7.2–7.4 (m, 2H), 7.60 (t of d, 1H), 8.62 (d of d); $^{13}$C-NMR(CDCl$_3$)ppm (delta) 26.04, 32.99, 62.77, 65.75, 70.01, 70.54, 119.10, 123.24, 124.02, 125.86, 131.06, 136.34, 144.66, 149.94, 152.13, 167.54, 168.73.

EXAMPLE 4

Employing the procedure of Example 3, but with the appropriate Wittig reagent of formula $(C_6H_5)_3P^{\oplus}CH_2R^3$ Cl$^{\ominus}$ in place of 2-picolyl trophenylphosphonium chloride, provides the following compounds.

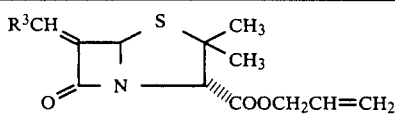

| R$^3$ | Time, Minutes | Temp. °C. | Elution Solvent* | % Yield | $^1$H-NMR(CDCl$_3$)ppm(delta): |
|---|---|---|---|---|---|
| Cl | 30 | −78 to +25 | A | 13(E) +3.2(Z) | E-isomer: 1.5 (s, 3H), 1.6 (s, 3H), 4.5 (s, 1H), 4.65 (d, 2H), 5.1–6.2 (m, 3H), 5.73 (d, 1H), 6.82 (d, 1H). Z-isomer: 1.5 (s, 3H), 1.6 (s, 3H), 4.57 (s, 1H), 4.7 (d, 2H), 5.15–6.24 (m, 3H), 5.77 (s, 1H), 6.37 (s, 1H). |
| CH$_3$S | 1 | −78 | B | 16(E) 2(Z) 15 (E + Z) | Z-isomer: 1.48 (s, 3H), 1.60 (s, 3H), 2.58 (s, 3H), 4.42 (s, 1H), 4.60 (d, 2H), 5.0–6.0 (m, 3H), 5.58 (s, 1H), 6.42 (s, 1H). E-isomer: 1.45 (s, 3H), 1.60 (s, 3H), 2.40 (s, 3H), 4.60 (s, 1H), 4.80 (d, 2H), 5.0–6.1 (m, 3H), 5.72 (d, 1H), 6.90 (d, 1H). |
| CHO$^{(a)}$ | 10 | 25 | B | 32(E) | 1.50 (s, 3H), 1.60 (s, 3H), 4.52 (s, 1H), 4.62 (d, 2H), 5.1–6.0 (m, 3H), 5.90 (d, 1H), 6.80 (d, 1H), 9.73 (d, 1H). |
| 2-quinolyl | 3 | −78 | B | 80(Z) | 1.5 (s, 3H), 1.62 (s, 3H), 4.6 (s, 1H), 4.7 (d, 2H), 5.1–6.2 (m, 3H), 6.35 (d, 1H), 7.0 (d, 1H), 7.2–8.2 (m, 6H). |
| C$_6$H$_5$S | 1 | −78 | B | 12(E,Z) | 1.5 (s, 2.2H), 1.55 (s, 0.8H), 1.65 (s, 2.2H), 1.7 (s, 0.8H), 4.5 (s, 1H), 4.5–4.8 (m, 2H), 5.1–6.1 (m, 4H), 6.8 (s, 0.26H), 7.15 (d, 0.74H), 7.4 (m, 5H). |
| ![Cl-pyridyl] | 3 | −78 | B | 20(E) | 1.45 (s, 3H), 1.55 (s, 3H), 4.55 (s, 1H), 4.65 (d, 2H), 5.2–6.1 (m, 3H), 6.15 (d, 1H), 6.75 (d, 1H), 7.05–7.75 (m, 3H). |
| C$_6$H$_5$ | 5 | −78 | A | 4(Z) | 1.5 (s, 3H), 1.6 (s, 3H), 4.6 (s, 1H), 4.68 (d, 2H), 5.1–6.1 (m, 3H), 5.77 (s, 1H), 6.57 (s, 1H), 7.2–7.64 (m, 3H), 7.64–8.16 |

-continued

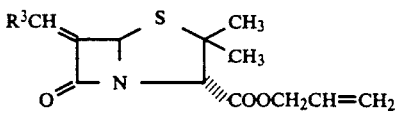

| R³ | Time, Minutes | Temp. °C. | Elution Solvent* | % Yield | ¹H-NMR(CDCl₃)ppm(delta): |
|---|---|---|---|---|---|
| | | | | 30(E) | (m, 2H).<br>1.52 (s, 3H), 1.62 (s, 3H), 4.60 (s, 1H), 4.69 (d, 2H), 5.1–6.3 (m, 3H), 6.1 (d, 1H), 7.03 (d, 1H), 7.4 (s, 5H). |
| CH₃ — N=N — CH₃ (pyrimidine) | 3 | −78 | C | 14(E)<br>10(E,Z) | 1.55 (s, 3H), 1.65 (s, 3H), 2.55 (s, 6H), 4.65 (s, 1H), 4.75 (d, 2H), 5.1–6.1 (m, 3H), 6.25 (d, 1H), 6.9 (s, 1H), 7.0 (d, 1H). |
| 3-OCH₃-2-pyridyl | 3 | −78 | D | (E) | 1.5 (s, 3H), 1.6 (s, 3H), 3.85 (s, 3H), 4.55 (s, 1H), 4.7 (d, 2H), 5.1–6.1 (m, 3H), 6.2 (d, 1H), 7.0–7.5 (m, 3H), 8.2 (t, 1H). |
| 3-OCH₂CH=CH₂-2-pyridyl | 5 | −78 | A¹ | (E) | 1.5 (s, 3H), 1.6 (s, 3H), 4.4–4.8 (m, 5H), 5.1–6.3 (m, 6H), 6.2 (d, 1H), 7.15 (d, 2H), 7.4 (d, 1H), 8.15 (t, 1H). |
| 6-methyl-2-pyridyl | 3 | −78 | B | 27 | E-isomer: 1.5 (s, 3H), 1.6 (s, 3H), 2.6 (s, 3H), 4.6 (s, 1H), 4.65 (m, 2H), 5.1–6.2 (m, 3H), 6.2 (d, 1H), 6.85 (d, 1H), 7.0–7.7 (m, 3H). |
| pyrazinyl | 5 | −78 | C | 50 | E-isomer: 1.5 (s, 3H), 1.6 (s, 3H), 4.55 (s, 1H), 4.67 (m, 2H), 5.0–6.2 (m, 3H), 6.15 (d, 1H), 6.95 (d, 1H), 8.4–8.8 (m, 3H). |
| 4-OCH₃-2-pyridyl | 5 | −78 | C | 13 | E-isomer: 1.5 (s, 3H), 1.7 (s, 3H), 4.55 (s, 1H), 4.7 (m, 2H), 5.1–6.2 (m, 3H), 6.2 (s, 1H), 6.5–7.0 (m, 3H), 8.5 (d, 1H). |

(a)Carried out with formylmethylene triphenylphosphorane in benzene.
*A = hexane/ethyl acetate (9:1),
A¹ = hexane/ethyl acetate (7:3),
B = chloroform
C = chloroform/ethyl acetate (9:1),
D = chloroform/ethyl acetate (99:1).
E-isomer (R³ is anti to beta-lactam)
Z-isomer (R³ is syn to beta-lactam)

EXAMPLE 5

Sodium 6(E)-(2-pyridyl)methylenepenicillanate

A mixture of 0.120 g (0.38 mmole) allyl 6-(E)-(2-pyridyl)methylenepenicillanate, 20 mg tetrakis (triphenylphosphine)palladium (O) and 20 mg triphenylphosphine was dissolved in 3 ml ethyl acetate and to this, under a nitrogen atmosphere, was added 0.76 ml (0.38 mmole) 0.5 molar sodium 2-ethylhexanoate in ethyl acetate. The mixture is stirred at room temperature for two hours, the precipitate was collected by filtration, washed with ethyl acetate and dried in vacuo to obtain 57 mg (48%) of the title compound as a yellow solid. ¹H-NMR(D₂O)ppm (delta): 1.55 (s, 6H), 4.33 (s, 1H), 6.17 (d, 1H, J=0.5 Hz), 7.03 (d, 1H, J=0.5 Hz), 7.17–8.07 (m, 3H), 8.57 (m, 1H); infrared spectrum (KBr): 3433, 1756, 1605 cm⁻¹.

EXAMPLE 6

Employing the appropriate starting material selected from the allyl esters provided in Example 4 in the procedure of Example 5 affords the following sodium salts in the like manner.

| R³ | Isomer | % Yield | Physical Properties |
|---|---|---|---|
| Cl | (E) | 95 | yellow solid, ¹H-NMR(D₂O) ppm (delta): 1.50 (s, 3H), 1.58 (s, 3H), 4.3 (s, 1H), 5.83 (d, 1H), 7.1 (d, 1H); infrared spectrum (KBr) cm⁻¹: 1573, 1607, 1688, 1775, 3460. |
| Cl | (Z) | 89 | Infrared spectrum (KBr) cm⁻¹: 1580, 1609, 1679, 1753, 3491. |
| CH₃S | (E) | 80 | white solid, ¹H-NMR(D₂O) ppm (delta): 1.48 (s, 3H), 1.56 (s, 3H), 2.50 (s, 3H), 4.20 (s, 1H), 5.88 (s, 1H), 7.2 (s, 1H); infrared spectrum (KBr) cm⁻¹: 1396, 1606, 1749, 2926, 2963, 3552. |
| C₆H₅ | (Z) | 60 | light yellow powder |
| C₆H₅ | (E) | 80 | white powder, ¹H-NMR(D₂O/DMSO) ppm (delta): 1.5 (s, 6H), 4.25 (s, 1H), 6.1 (d, 1H), 7.0 (d, 1H), 7.4 (s, 5H); infrared spectrum (KBr) cm⁻¹: 1626, 1642 1655, 1742, 3434. |

EXAMPLE 6A

6-Phenylthiomethylene penicillanic acid

A mixture of 93 mg (0.26 mmole) allyl 6-phenylthiomethylenepenicillanate (mixed isomers) and 10 mg each of tetrakis (triphenylphosphine)palladium (O) and triphenylphosphene was dissolved in 1 ml ethyl acetate and 0.52 ml of 0.5M sodium 2-ethylhexanoate in ethyl acetate was added at room temperature and the resulting mixture was stirred for 10 hours under nitrogen. Since very little salt precipitated, the mixture was quenched with water and extracted with methylene chloride. The aqueous layer was acidified (pH 3.5) and extracted with methylene chloride. The dried extracts were concentrated in vacuo to afford 63 mg (75%) of the free acid as a mixture of isomers. ¹H-NMR(CDCl₃)ppm (delta): 1.5 (s, 2.1H), 1.55 (s, 0.9H), 1.6 (s, 2.1H), 1.65 (s, 0.9H), 4.4 (s, 0.7H), 4.5 (s, 0.3H), 5.38 (d, 0.7H), 5.7 (s, 0.3H), 6.7 (s, 0.3H), 7.1 (d, 0.7H), 7.5 (m, 5H).

EXAMPLE 7

Allyl 1,1-Dioxo-6(E)-(2-pyridyl)-methylenepenicillanate

To a solution of 1 30 g (4.09 mmole) allyl 6(E)(2-pyridyl)methylenepenicillanate in 15 ml methylene chloride was added 1.70 g (8.2 mmole) of 80–85% pure m-chloroperbenzoic acid and the mixture stirred under nitrogen for three hours at room temperature. After quenching with saturated sodium thiosulfate solution and water, the mixture was extracted with methylene chloride, the organic layer adjusted to pH 7.5 with saturated sodium bicarbonate solution, washed with water, dried (MgSO₄) and the solvent evaporated in vacuo to give 1.4 g (98%) of product as a yellow oil. The oil was purified by silica gel column chromatography, eluting with 7:3 hexane/ethyl acetate to yield 0.78 g (55%) of the title sulfone as colorless crystals. ¹H-NMR(CDCl₃)ppm (delta): 1.48 (s, 3H), 1.63 (s, 3H), 4.45 (s, 1H), 4.73 (d, 2H), 5.1–6.2 (m, 3H), 5.77 (d, 1H, J=0.5Hz), 7.27 (d, 1H, J=0.5Hz), 7.1–8.1 (m, 3H), 8.6 (m, 1H); ¹³C-NMR(CDCl₃)ppm (delta) 18.53, 20.43, 63.18, 64.25, 66.63, 72.04, 119.91, 124.64, 126.03, 130.68, 132.83, 136.77, 150.31, 166.86, 168.11. Infrared (KBr) cm⁻¹: 1323, 1586, 1759, 1783, 3437.

EXAMPLE 8

Allyl 1,1-dioxo-6(E)-(2-hydroxyethylidene)penicillanate

To a solution of 0.190 g (0.61 mmole) allyl 1,1-dioxo-6(E)-formylmethylenepenicillanate in 4 ml of dry tetrahydrofuran at −78° C. was added 0.61 ml (0.61 mmole) of 1M diisobutylaluminum hydride in hexane. The mixture was stirred at −78° C. for ten minutes, quenched with methanol, stirred at room temperature for 20 minutes and filtered. The filtrate was concentrated in vacuo to give 0.258 g of crude product which was diluted with water, extracted with chloroform and the organic layer dried (MgSO₄). Evaporation of chloroform afforded 160 mg of material which was further purified by silica gel column chromatography, eluting with 4:1 chloroform/ethyl acetate to yield 113 mg (60%) of the title compound. ¹H-NMR(CDCl₃)ppm (delta): 1.40 (s, 3H), 1.60 (s, 3H), 2.60 (bs, 1H), 4.3 (m, 2H), 4.4 (s, 1H), 4.7 (d, 2H), 5.1–6.0 (m, 3H), 5.25 (d, 1H), 6.38 (m, 1H).

EXAMPLE 9

Starting with the appropriate 6-methylenepenicillanate ester (n=0) provided in Example 4 as starting materials in the procedure of Example 7 afforded the following compounds.

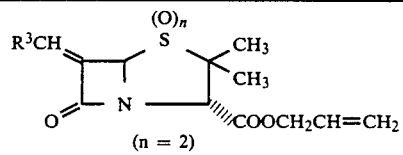

(n = 2)

| R³ | Isomer | % Yield | Silica Gel Eluant | Physical Properties ¹H-NMR(CDCl₃)ppm(delta): |
|---|---|---|---|---|
| CHO | (E) | 22 | CHCl₃ | 1.42 (s, 3H), 1.60 (s, 3H), 4.50 (s, 1H), 4.70 (d, 2H), 5.1–6.0 (m, 3H), 5.32 (s, 1H), 7.1 (m, 1H), 9.73 (d, 1H). |
| 2-quinolyl | (E) | 28 | CHCl₃ | 1.5 (s, 3H), 1.6 (s, 3H), 4.45 (s, 1H), 4.7 (d, 2H), 5.1–6.1 (m, 3H), 5.8 (d, 1H), 7.3–8.5 |

-continued $$R^3CH \underset{O}{\overset{}{\bigg|}} \overset{(O)_n}{\underset{N}{\overset{S}{\bigg|}}} \underset{COOCH_2CH=CH_2}{\overset{CH_3}{\underset{CH_3}{\bigg|}}}$$

(n = 2)

| $R^3$ | Isomer | % Yield | Silica Gel Eluant | Physical Properties $^1$H-NMR(CDCl$_3$)ppm(delta): |
|---|---|---|---|---|
| 6-Chloro-2-pyridyl | (E) | 34 | CHCl$_3$ | (m, 7H). 1.5 (s, 3H), 1.6 (s, 3H), 4.45 (s, 1H), 4.7 (d, 2H), 5.1–6.3 (m, 3H), 5.75 (d, 1H), 7.1–7.8 (m, 4H). |
| 2,6-dimethylpyrimidinyl | (E) | 8 (79% crude) | CHCl$_3$ | 1.5 (s, 3H), 1.6 (s, 3H), 2.55 (s, 6H), 4.5 (s, 1H), 4.7 (d, 2H), 5.0–5.9 (m, 3H), 5.7 (d, 1H), 6.9 (s, 1H), 7.3 (d, 1H). |
| 3-methoxy-2-pyridyl | (E) | 47 | Hexane/ethyl acetate(1:1) | 1.4 (s, 3H), 1.6 (s, 3H), 3.8 (s, 3H), 4.4 (s, 1H), 4.65 (d, 2H), 5.3–6.2 (m, 3H), 5.8 (d, 1H), 7.4 (s, 1H), 7.8 (d, 1H), 8.35 (t, 1H). |
| 3-allyloxy-2-pyridyl | (E) | 54 | Hexane/ethyl acetate(1:1) | 1.45 (s, 3H), 1.6 (s, 3H), 4.4–4.8 (m, 5H), 5.1–6.3 (m, 6H) 5.65 (d, 1H), 7.15 (d, 2H), 7.7 (d, 1H), 8.15 (t, 1H). |
| 6-methyl-2-pyridyl | (E) | 53 | CHCl$_3$ | 1.5 (s, 3H), 1.64 (s, 3H), 2.64 (s, 3H), 4.48 (s, 1H), 4.74 (d of t, 2H), 5.3–5.5 (m, 2H), 5.8 (d, 1H), 7.1–7.2 (m, 2H), 7.25 (d, 1H), 7.6 (t, 1H). Infrared spectrum (KBr)cm$^{-1}$: 1588, 1688, 1728, 1756, 1795, 2931, 2976, 3433. |
| pyrazin-2-yl | (E) | 40 | CHCl$_3$/ethyl acetate(9:1) | 1.56 (s, 3H), 1.7 (s, 3H), 4.6 (s, 1H), 4.85 (m, 2H), 5.2–6.2 (m, 3H), 5.8 (d, 1H), 7.4 (d, 1H), 8.5–9.0 (m, 3H). |
| 4-methoxy-2-pyridyl | (E) | 99 | No Purification required | 1.5 (s, 3H), 1.7 (s, 3H), 3.9 (s, 3H), 4.5 (s, 1H), 4.75 (m, 2H), 5.2–6.3 (m, 3H), 5.7 (d, 1H), 6.7–7.0 (m, 2H), 7.2 (d, 1H), 8.5 (d, 1H). |

*In a subsequent run a 29% yield of sulfone (n = 2) was obtained by elution from a silica gel column with chloroform containing 2% ethyl acetate and a more polar fraction, identified as the sulfoxide (n = 1) in 27% yield.

EXAMPLE 9A

Allyl 6(E)-[(1-oxoquinolin-2-yl)methylene]-1,1-dioxopenicillanate

Allyl 6(E)-(quinolin-2-yl)methylene]-1-oxopenicillanate (obtained as byproduct from preparation of corresponding sulfone, see previous Example, asterisk) (124 mg, 0.313 mmole) was dissolved in 5 ml methylene chloride and 195 mg (0.904 mmole) of 80% m-chloroperbenzoic acid was added. The mixture was stirred at room temperature for 48 hours, quenched with water and extracted with methylene chloride The extracts were washed with saturated sodium bicarbonate solution, water, dried and concentrated in vacuo to a yellow oil. The oil was purified by silica gel column chromatography to give 45 mg (35%) of the title N-oxide as a yellow solid. $^1$H-NMR(CDCl$_3$)ppm (delta): 1.45 (s, 3H), 1.6 (s, 3H), 4.45 (s, 1H), 4.7 (m, 2H), 5.0–6.0 (m, 3H), 5.85 (d, 1H), 7.3–8.0 (m, 7H).

EXAMPLE 10

Sodium 1,1-Dioxo-6(E)-(2-pyridyl)-methylenepenicillanate

A mixture of allyl 1,1-dioxo-6(E)-(2-pyridyl)-methylenepenicillanate (0.14 g, 0.4 mmole), 20 mg tetrakis (triphenylphosphine)palladium (0) and 20 mg triphenylphosphine was dissolved in 2 ml ethyl acetate and under nigrogen was added 0.8 ml (0.4 mmole) of a 0.5M solution of sodium 2-ethyl hexanoate in ethyl acetate. The resulting mixture was stirred at room temperature for five minutes. The resulting precipitate was filtered, washed with ethyl acetate and dried to afford 0.13 g (95%) of the sodium salt as a yellow solid. $^1$H-NMR($D_2O$)ppm (delta): 1.50 (s, 3H), 1.60 (s, 3H), 4.23 (s, 1H), 5.90 (d, 1H, J=1 Hz), 7.1–8.0 (m, 4H), 8.57 (m, 1H). Infrared spectrum (KBr) cm$^{-1}$: 1590, 1621, 1770, 3454.

EXAMPLE 11

Allyl 1,1-Dioxo-6(E)-(1-oxo-2-pyridyl)-methylenepenicillanate

A solution of allyl 1,1-dioxo-6(E)-(2-pyridyl)-methylenepenicillanate (100 mg, 0.286 mmole) in 5 ml of methylene chloride was treated with m-chloroperbenzoic acid (120 mg, 0 59 mmole) and stirred at room temperature for three days. The mixture was quenched with saturated sodium thiosulfate solution and extracted with methylene chloride. The organic layer was neutralized with saturated sodium bicarbonate solution, washed with water, dried and concentrated to give 82 mg of yellow oil. The yellow oil was purified by silica gel column chromatography using ethyl acetate as eluent to give 22 mg (21%) of title compound and 14 mg (13%) of a byproduct, 2,3-epoxypropanyl 1,1-dioxo-6(E)-(1-oxo-2-pyridyl)methylenepenicillanate. Allyl 1,1-dioxo-6(E)-(1-oxo-2-pyridyl)-methylenepenicillanate: $^1$H-NMR(CDCl$_3$)ppm (delta): 1.5 (s, 3H), 1.6 (s, 3H), 4.45 (d, 1H), 4.7 (d, 2H), 5.1–6.0 (m, 3H), 5.8 (s, 1H), 7.1–8.4 (m, 5H).

EXAMPLE 12

The compounds of the formula below were also obtained by hydrolysis of the appropriate allyl ester by the method of Example 10.

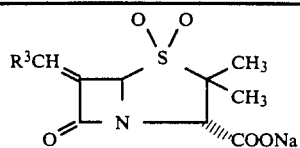

Use of potassium 2-ethylhexanoate in place of sodium 2-ethyl-hexanoate provided the corresponding potassium salts of the above formula.

| R$^3$ | Isomer | % Yield | Physical Properties |
| --- | --- | --- | --- |
| HOCH$_2$ | (E) | 53 | $^1$H-NMR(D$_2$O)ppm(delta): 1.5 (s, 3H), 1.6 (s, 3H), 4.24 (s, 1H), 4.30 (dd, 2H), 5.75 (s, 1H), 7.20 (d, 1H); Infrared spectrum (KBr)cm$^{-1}$: 1618, 1674, 1767, 3408, 3440. |
| 2-quinolyl | (E) | 76 | $^1$H-NMR(250 MHz, DMSO)ppm(delta): 1.45 (s, 3H), 1.48 (s, 3H), 3.82 (s, 1H), 5.96 (s, 1H), 7.55–8.55 (m, 7H); Infrared spectrum (KBr)cm$^{-1}$: 1619, 1771, 3437. |
| 6-chloro-2-pyridyl | (E) | 86 | $^1$H-NMR(250 MHz, DMSO)ppm(delta): 1.56 (s, 3H), 1.64 (s, 3H), 4.34 (s, 1H), 6.18 (s, 1H), 7.45–8.0 (m, 4H); Infrared spectrum (KBr)cm$^{-1}$: 1624, 1771, 3433. |
| CH$_3$-pyrimidinyl-CH$_3$ (4,6-dimethylpyrimidin-2-yl) | (E) | 75 | $^1$H-NMR(250 MHz, D$_2$O)ppm(delta): 1.52 (s, 3H), 1.60 (s, 3H), 2.5 (s, 6H), 4.32 (s, 1H), 6.16 (d, 1H), 7.35 (d, 1H), 7.65–7.75 (m, 1H); Infrared spectrum (KBr)cm$^{-1}$: 1629, 1781, 3403. |
| 3-methoxy-2-pyridyl (OCH$_3$) | (E) | 55 | $^1$H-NMR(250 MHz, CDCl$_3$)ppm(delta): 1.42 (s, 3H), 1.48 (s, 3H), 3.85 (s, 1H), 3.95 (s, 3H), 5.85 (d, 1H), 7.45 (d, 1H), 7.45–8.0 (m, 2H), 8.22 (m, 1H); Infrared spectrum (KBr)cm$^{-1}$: 1617, 1767, 3454. |
| 1-oxo-2-quinolyl | (E) | 56 | Infrared spectrum (KBr)cm$^{-1}$: 1553, 1622, 1769, 3413. |
| 3-allyloxy-2-pyridyl (OCH$_2$CH=CH$_2$) (Potassium salt) hygroscopic | (E = Z) | 99 | $^1$H-NMR(DMSO)ppm(delta): 1.35 (s, 6H), 1.4 (s, 1.4H), 1.44 (s, 6H), 1.48 (s, 1.4H), 3.7 (s, 1H), 4.55 (d, 1H), 4.75 (d, 1H), 5.15–5.5 (m, 2H), 5.67 (s, 0.6H), 5.8 (s, 0.4H), 5.8–6.0 (m, 0.5H), 6.0–6.2 (m, 0.5H), 6.75–7.0 (m, 2H), 7.4–7.6 (m, 1H), 8.2 (d, 0.5H). Infrared spectrum (KBr)cm$^{-1}$: 1613, 1760, 3429. |

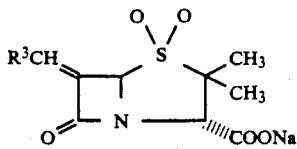

Use of potassium 2-ethylhexanoate in place of sodium 2-ethyl-hexanoate provided the corresponding potassium salts of the above formula.

| R³ | Isomer | % Yield | Physical Properties |
|---|---|---|---|
| 4-methoxy-2-methylpyridin-3-yl (OCH₃ on pyridine) | (E) | 76 | $^1$H-NMR(D$_2$O)ppm(delta): 1.8 (s, 3H), 1.9 (s, 3H), 4.56 (s, 1H), 7.2 (1H), 7.34 (1H), 7.62 (1H), 8.68 (1H). $^{13}$C-NMR(D$_2$O)ppm(delta): 20.9, 22.7, 58.7, 64.6, 68.7, 74.6, 113.9, 115.9, 134.0, 134.2, 154.6, 155.1, 169.4, 173.7, 175.6. |

EXAMPLE 13

Pivaloyloxymethyl 6(E)-(methylthio)-methylenepenicillanate

A mixture of 2.4 mmole (methylthiomethyl)triphenylphosphonium chloride, 2.4 mmole sodium amide in 5 ml dry tetrahydrofuran (THF) was stirred at room temperature for 20 minutes. To the resulting yellow solution at −78° C. was added a solution of 788 mg (2.4 mmole) pivaloyloxymethyl 6-oxopenicillanate in 10 ml of dry THF. The mixture was stirred at −78° C. for one minute, poured into saturated ammonium chloride solution and extracted with ethyl acetate. The organic layer was dried (Na$_2$SO$_4$) and the solvent evaporated in vacuo to afford 774 mg of crude product which was purified by silica gel column chromatography, eluting with chloroform to yield 220 mg (24.5%) of pure product. $^1$H-NMR(CDCl$_3$)ppm (delta): 1.25 (s, 9H), 1.50 (s, 3H), 1.65 (s, 3H), 2.45 (s, 3H), 4.45 (s, 1H), 6.85 (m, 3H), 7.0 (d, 1H).

EXAMPLE 14

Pivaloyloxymethyl 6-(E)methylsulfonylmethylene penicillanate 1-oxide (A) and the corresponding 1,1-dioxide (B)

To a solution of 215 mg (0.58 mmole) pivaloyloxymethyl 6(E)-(methylthiomethyl)methylenepenicillanate in 5 ml methylene chloride was added 375 mg (1.74 mmole, 3 equivalents) 80% m-chloroperbenzoic acid. The mixture was stirred at room temperature four hours, quenched with water, saturated sodium thiosulfate solution, sodium bicarbonate and extracted with chloroform. The organic phase was washed three times with water, dried (MgSO$_4$) and concentrated in vacuo to give 200 mg of the mixed products. The crude mixture was purified by silica gel chromatography, eluting with chloroform/ethyl acetate (9:1) to yield 25 mg of the 1-oxide (A) and 45 mg of the 1,1-dioxide product (B).

(A): $^1$H-NMR(CDCl$_3$)ppm (delta): 1.21 (s, 9H), 1.3 (s, 3H), 1.7 (s, 3H), 3.1 (s, 3H), 4.7 (s, 1H), 5.8 (AB quartet, 2H), 5.85 (d, 1H), 7.1 (d, 1H); infrared spectrum (CHCl$_3$) cm$^{-1}$: 1333, 1759, 1807, 2927, 2960.

(B): $^1$H-NMR(CDCl$_3$)ppm (delta): 1.2 (s, 9H), 1.45 (s, 3H), 1.6 (s, 3H), 3.15 (s, 3H), 4.5 (s, 1H), 5.6 (d, 1H), 5.8 (AB quartet, 2H), 7.2 (d, 1H); infrared spectrum (CHCl$_3$) cm$^{-1}$: 1324, 1758, 1800, 2929, 2956.

EXAMPLE 15

Allyl 6-alpha-(N-methylpyrrol-2-yl)hydroxymethyl-1,1-dioxopenicillanate

Allyl 6-alpha-bromo-1,1-dioxopenicillanate (520 mg, 1.48 mmole) was dissolved in 10 ml dry tetrahydrofuran (THF) and cooled to −78° C. A solution of methylmagnesium bromide (0.52 ml, 2.85M in THF) was added and the mixture stirred for five minutes at −78° C. N-methylpyrrole-2-carboxaldehyde (162 mg, 0.16 ml) was added and stirring continued at −78° C. for 20 minutes. The mixture was poured into saturated ammonium chloride solution, extracted with ethyl acetate and the organic layer dried (MgSO$_4$). Evaporation of solvent in vacuo gave 466 mg of crude product which was purified by silica gel chromatography, eluting with chloroform/ethyl acetate (9:1) to give 180 mg (32%) of the pure title compound. $^1$H-NMR(CDCl$_3$)ppm (delta) 1.4 (s, 3H), 1.62 (s, 3H), 3.68 (s, 3H), 4.0–4.4 (m, 1H), 4.42 (s, 1H), 4.5–4.8 (m, 3H), 5.0–6.0 (m, 4H), 6.0–6.7 (m, 3H).

EXAMPLE 16

Allyl 6(E)-(N-methylpyrrol-2-yl)methylene-1,1-dioxopenicillanate

Allyl 6-alpha-(N-methylpyrrol-2-yl)hydroxymethyl-1,1-dioxopenicillanate (180 mg, 0 47 mmole) was dissolved in 3 ml tetrahydrofuran and 0.15 ml acetic anhydride and 0.2 ml pyridine were added. The mixture was stirred at room temperature for one hour. The reaction was quenched with water and extracted with ethyl acetate. The organic layer was dried and solvent evaporated in vacuo to yield 162 mg of material still containing starting material. This was dissolved in methylene chloride (3 ml) and 0.15 ml acetyl chloride and 0.2 ml pyridine added. The mixture was stirred two hours at room temperature and worked up as before to give 140 mg of crude product which was purified by silica gel column chromatography to give 72 mg (42%) of pure product. Recrystallization from ethyl acetate gave colorless needles $^1$H-NMR(CDCl$_3$)ppm (delta) 1.45 (s, 3H), 1.65 (s, 3H), 3.7 (s, 3H), 4.4 (s, 3H), 4.6–4.9 (m, 2H), 5.1–6.4 (m, 4H), 6.6–7.0 (m, 2H), 7.5 (dd, 1H).

EXAMPLE 17

Sodium 6(E)-(N-methylpyrrol-2-yl)methylene-1,1-dioxopenicillanate

A solution of 46 mg allyl 6(E)-(N-methylpyrrol-2-yl)methylene-1,1-dioxopenicillanate, 5 mg tetrakis (triphenylphosphine)palladium (O), 4 mg triphenylphosphine and one ml methylene chloride was stirred under nitrogen for five minutes. The resulting mixture was diluted with one ml ethyl acetate and 0.25 ml sodium 2-ethyl hexanoate in ethyl acetate added. After stirring at room temperature for one hour, the mixture was filtered and the precipitate washed with ethyl acetate and ethyl ether to give 30 mg of yellow solid. $^1$H-NMR(D$_2$O)ppm (delta): 1.50 (s, 3H), 1.60 (s, 3H), 3.65 (s, 3H), 4.10 (s, 1H), 5.4 (s, 1H), 6.1–6.5 (m, 1H), 7.0 (s, broad, 2H), 7.2–7.4 (m, 1H); infrared (KBr) cm$^{-1}$: 1568, 1616, 1660, 1745, 3465.

EXAMPLE 18

Employing the appropriate aldehyde of formula R$^{13}$CHO in the procedure of Example 15 affords the corresponding compounds of the formula below

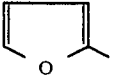

| R$^{13}$ | % Yield | Silica Gel Eluant* | $^1$H-NMR(CDCl$_3$)ppm(delta): |
|---|---|---|---|
| 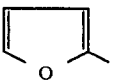 | 30 | A | 6-alpha-isomer: 1.4 (s, 0.39H), 1.5 (s, 2.61H), 1.62 (s, 0.39H), 1.7 (s, 2.61H), 3.0 (bs, 1H), 4.0–4.4 (m, 1H), 4.45 (s, 1H), 4.5–4.9 (m, 2H), 5.1–6.1 (m, 4H), 6.3–6.6 (m, 2H), 7.45 (m, 1H). |
| 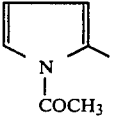 | 6 | A | Mixture of 6-alpha, 8R and 6-alpha, 8S isomers |
| 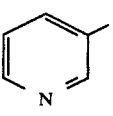 | 38 | A | 1.4 (s, 3H), 1.60 (s, 3H), 2.50 and 2.60 (s, 3H), 4.1–4.4 (m, 1H), 4.4 and 4.5 (s, 1H), 4.6–5.0 (m, 3H), 5.1–6.0 (m, 4H), 6.0–7.2 (m, 4H). |
| C$_6$H$_5$ | 78 | A | 1.4 (s, 3H), 1.6 (s, 3H), 3.28 (bs, 1H), 3.8–4.2 (m, 1H), 4.35 (s, 1H), 4.45–4.8 (m, 3H), 5.0–6.1 (m, 4H), 7.3 (s, 5H). |
| 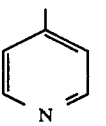 | 33 | B | 1.3 (s, 3H), 1.55 (s, 3H), 4.04 (bs, 1H), 4.35 (s, 1H), 4.5–4.85 (m, 3H), 5.1–6.1 (m, 4H), 7.1–7.4 (m, 1H), 7.6–8.0 (m, 1H), 8.2–8.7 (m, 2H). |
| 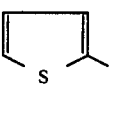 | 35 | B | 1.3 (s, 3H), 1.55 (s, 3H), 4.0 (m, 1H), 4.35 (s, 1H), 4.4–6.8 (m, 3H), 5.1–6.2 (m, 4H), 7.2–7.5 (m, 2H), 8.2–8.6 (m, 2H). |
| 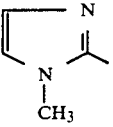 | 50 | B | 1.25 (s, 0.75H), 1.35 (s, 2.25H), 1.55 (s, 3H), 3.3 (bs, 1H), 4.05 (dd, 1H), 4.3 (s, 1H), 4.3–4.8 (m, 3H), 5.0–6.2 (m, 4H), 6.8–7.4 (m, 3H). |
| CH$_2$=CH | 21 | | 1.4 (s, 3H), 1.6 (s, 3H), 3.0 (bs, 1H), 3.7–4.0 (m, 1H), 4.4–4.8 (m, 4H), 5.0–6.3 (m, 6H). |
|  | 25 | D | 1.36 (s, 1.5H), 1.40 (s, 1.5H), 1.60 (s, 1.5H), 1.65 (s, 1.5H), 3.7 (s, 3H), 4.0–4.5 (m, 2H), 4.4 (s, 1H), 4.5–4.8 (m, 2H), 5.0–6.0 (m, 4H), 6.7 (s, 1H), 6.85 (s, 1H). |

-continued

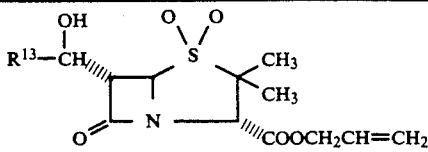

| R[13] | % Yield | Silica Gel Eluant* | $^1$H-NMR(CDCl$_3$)ppm(delta): |
|---|---|---|---|
| (2-thiazolyl, with CH on 2-position) | 52 | D | 6-alpha, 8S isomer: 1.4 (s, 3H), 1.6 (s, 3H), 4.38 (dd, 1H), 4.43 (s, 1H), 4.67–4.75 (m, 2H), 4.76 (d, 1H), 5.3–5.5 (m, 2H), 5.63 (d, 1H), 5.85–6.05 (m, 1H), 7.4 (d, 1H), 7.8 (d, 1H). 6-alpha, 8R isomer: 1.36 (s, 3H), 1.60 (s, 3H), 4.22 (d, 1H), 4.4 (s, 1H), 4.65 (m, 2H), 4.88 (s, 1H), 5.25–5.5 (m, 2H), 5.55 (d, 1H), 5.8–6.0 (m, 1H), 7.35 (d, 1H), 7.75 (d, 1H). |
| C$_6$H$_5$—N-triazolyl | 42 | E | 6-alpha, 8S isomer: 1.44 (s, 3H), 1.62 (s, 3H), 3.68 (bs, 1H), 4.31 (dd, 1H), 4.5 (s, 1H), 4.74 (d, 2H), 4.86 (d, 1H), 5.4 (m, 3H), 5.9 (m, 1H), 7.5 (m, 3H), 8.02 (s, 1E), 8.14 (m, 2H), IR: 3482, 1802 cm$^{-1}$. |
| pyrimidinyl | 57 crude<br>9 LP<br>8 MP | A (less polar isomer)<br>F (more polar isomer) | Less polar 6-alpha, 8S isomer: 1.41 (s, 3H), 1.6 (s, 3H), 4.45 (s, 1H), 4.4–4.8 (m, 4H), 5.2–5.6 (m, 3H), 5.7–6.3 (m, 1H), 7.35 (t, 1H), 8.85 (d, 2H).<br>More polar 6-alpha, 8R isomer: 1.45 (s, 3H), 1.6 (s, 3H), 4.4 (s, 1H), 4.45 (dd, 1H), 4.7–4.9 (m, 2H), 4.95 (d, 1H), 5.2–5.6 (m, 3H), 5.7–6.3 (m, 1H), 7.35 (t, 1H), 8.85 (d, 1H). |
| pyrimidinyl (isomer) | 25%, 1st fraction (one isomer)<br>12%, 2nd fraction (mixture of 2 isomers) | D | 1st fraction: 1.4 (s, 3H), 1.6 (s, 3H), 4.2–4.4 (m, 2H), 4.5–5.0 (m, 3H), 5.1–6.1 (m, 6H), 7.6 (d, 1H), 8.87 (d, 1H), 9.23 (s, 1H). |
| pyrazinyl | 56<br>70:30 mixture of isomers | D | 1.4 (s, 3H), 1.57 (s, 3H), 4.25 (m, 1H), 4.37 (s, 0.7H), 4.42 (s, 0.3H), 4.75 (m, 2H), 4.8 (d, 0.3H), 4.85 (d, 0.7H), 5.25–5.5 (m, 3H), 5.9 (m, 1H), 8.52 (m, 2H), 8.84 (m, 1H). |
| imidazolyl (H, N**) | 22<br>1:2 mixture of isomers | D | 1.4 (s, 1H), 1.46 (s, 2H), 1.6 (s, 1H), 1.63 (s, 2H), 4.12 (m, 1H), 4.22 (m, 1H), 4.41 and 4.46 (s, 1H), 4.6–4.8 (m, 2H), 4.95 (d, 1H), 5.2–5.5 (m, 3H), 5.9 (m, 1H), 6.95 and 7.05 (s, 1H), 7.28 and 7.36 (s, 1H). |
| pyridazinyl | 35<br>two isomers | G | 1.38–1.40 (d, 3H), 1.56–1.57 (d, 3H), 4.20–4.40 (m, 2H), 4.59–4.72 (m, 2H), 4.86–4.88 (d, 0.5H), 5.04–5.06 (d, 0.5H), 5.26–5.42 (m, 2H), 5.50–5.62 (m, 1H), 5.82–6.00 (m, 1H), 7.50–7.86 (m, 1H), 7.90–8.08 (m, 1H), 9.02–9.10 (m, 1H), Infrared spectrum: 1800 cm$^{-1}$. |
| CH$_3$O-benzothiazolyl | 46<br>two isomers | A | 1.34 (s, 3H), 1.52 (s, 3H), 3.8 (s, 3H), 4.4 (m, 1H), 4.5–4.7 (m, 2H), 4.9 d, 1H), 5.2–5.5 (m, 3H), 5.66 (bs, 1H), 5.7–6.0 (m, 1H), 7.0 (dd, 1H), 7.2–7.3 (m, 1H), 7.82 (d, 1H). |

*A - Chloroform/ethyl acetate (9:1)
B - Ethyl acetate/chloroform (7:3)
C - Chloroform/ethyl acetate (19:1)
D - Chloroform/methanol (19:1)
E - Chloroform
F - Chloroform/ethyl acetate (1:1)
G - Ethyl acetate
**Starting aldehyde used was 1-diethoxymethylimidazol-2-carboxaldehyde

EXAMPLE 19

Allyl 6-(furan-2-yl)methylene-1,1-dioxopenicillanate, (E)- and (Z)-isomers

To a solution of 310 mg (0.84 mmole) allyl 6-alpha-(furan-2-yl)hydroxymethyl-1,1-dioxopenicillanate in 5 ml methylene chloride was added 0.14 ml (1 mmole) triethylamine and 0.1 ml (0 924 mmole) trifluoromethylsulfonyl chloride and the mixture stirred under nitrogen at room temperature for two hours. The reaction was quenched with water, extracted with methylene chloride, the extracts dried (MgSO$_4$) and solvent evaporated in vacuo to give 330 mg of crude product. Purification by silica gel column chromatography eluting with chloroform afforded 130 mg of product which was estimated to be a 4:1 mixture of (E)- and (Z)-isomers by HPLC. $^1$H-NMR(CDCl$_3$)ppm (delta): 1.47 (s, 3H), 1.61 (s, 3H), 4.47 (s, 1H), 4.75 (d, 2H), 5.1–6.2 (m, 4H), 5.52 (dd, 1H), 6.8 (m, 1H), 7.15 (d, 1H), 7.6 (d, 1H).

EXAMPLE 20

Allyl 6(E)-(N-acetylpyrrol-2-yl)methylene-1,1-dioxopenicillanate

A. Allyl 6-(N-acetylpyrrol-2-yl)acetoxymethyl-1,1dioxopenicillanate

Allyl 6-(N-acetylpyrroyl-2-yl)hydroxymethyl-1,1-dioxopenicillanate (210 mg, 0.51 mmole) was dissolved in 3 ml tetrahydrofuran and 0.16 ml acetic anhydride and 0.2 ml pyridine were added and the mixture stirred at room temperature for 24 hours. The reaction was quenched with water, extracted with methylene chloride, the extracts dried and concentrated to give 171 mg (75%) of yellow crystals, $^1$H-NMR(CDCl$_3$)ppm (delta): 1.4 (s, 3H), 1.6 (s, 3H), 2.15 (s, 3H), 2.55 (s, 3H), 4.15–4.3 (dd, 1H), 4.4 (s, 1H), 4.6–4.8 (m, 3H), 5.1–6.0 (m, 3H), 6.1–6.6 (m, 2H), 6.6–7.4 (m, 2H). B. The N,O-diacetate product from Part A, 170 mg (0.38 mmole) was dissolved in methylene chloride and 47 mg (0.38 mmole) 1,5-diazabicyclo[4.3.0]non-5-ene (DBN) was added. The mixture was stirred at room temperature for one hour. Water was added and the mixture extracted with methylene chloride. The extracts were dried and concentrated to yield 158 mg of oil which was purified by silica gel chromatography using 2% ethyl acetate in chloroform as eluant to give 108 mg of product as a pale yellow oil. $^1$H-NMR(CDCl$_3$)ppm (delta): 1.5 (s, 3H), 1.6 (s, 3H), 2.55 (s, 3H), 4.4 (s, 1H), 4.65 (d, 2H), 5.0–6.0 (m, 4H), 6.3 (t, 1H), 6.8 (dd, 1H), 7.2 (m, 1H), 8.2 (d, 1H).

EXAMPLE 21

Allyl 6(E)-phenylmethylene-1,1-dioxopenicillanate and Corresponding (Z)-isomer A. Employing 1.98 mmoles allyl 6-phenylhydroxymethyl-1,1-dioxopenicillanate, 4.2 mmoles acetyl chloride and 0.4 ml pyridine in the method of Part A of the preceding Example gave 0.7 g (84%) of allyl 6-phenylacetoxymethyl-1,1-dioxopenicillanate as a light yellow gum. $^1$H-NMR(CDCl$_3$)ppm (delta): 1.3 and 1.4 (s, 3H), 1.62 (s, 3H), 2.08 and 2.2 (s, 3H), 4.2 (dd, 1H), 4.4 (s, 1H), 4.5 (d, 1H), 4.65 (d, 2H), 6.25 (m, 1H), 7.3 (m, 5H).

B. To a solution of the product of Part A (0.7 g, 1.66 mmole) in methylene chloride was added 0.25 ml (1.67 mmole) 1,5-diazabicyclo[5.4.0]undec-5-ene (DBU) and the mixture stirred at room temperature for ten minutes. Water and methylene chloride were added, the layers separated and the organic extracts washed with 0.1N hydrochloric acid, brine and water. The extracts were dried (Na$_2$SO$_4$) and solvent evaporated to give 660 mg of crude product which was purified by column chromatography on 100 g silica gel, eluting with chloroform to provide 68 mg (11%) of the (Z)-isomer $^1$H-NMR(CDCl$_3$)ppm (delta): 1.45 (s, 3H), 1.60 (s, 3H), 4.45 (s, 1H), 4.68 (d, 2H), 5.37 (d, 1H), 5.1–6.05 (m, 3H), 7.35 (d, 1H), 7.45 (s, 1H). Subsequent eluate fractions gave 100 mg (16.7%) of the (E)-isomer of the title compound as a colorless oil which formed crystals upon standing. $^1$H-NMR(CDCl$_3$)ppm (delta): 1.45 (s, 3H), 1.58 (s, 3H), 4.45 (s, 1H), 4.75 (d, 2H), 5.45 (d, 1H), 5.2–6.2 (m, 3H), 7.36 (d, 1H), 7.45 (s, 5H).

EXAMPLE 22

The following compounds were prepared from the appropriate hydroxy compound selected from those provided in Example 18 by the procedure of Example 19.

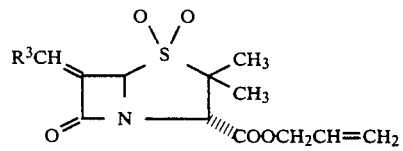

| R$^3$ | % Yield | Silica Gel Eluant | $^1$H-NMR(CDCl$_3$)ppm(delta): |
|---|---|---|---|
| 3-pyridyl | 22(E) 19(Z) | Ethyl ether | (E)-isomer: 1.5 (s, 3H), 1.7 (s, 3H), 4.5 (s, 1H), 4.7 (d, 2H), 5.5 (d, 1H), 5.1–6.2 (m, 3H), 7.3–7.5 (m, 2H), 7.7–8.0 (m, 1H), 8.53–8.83 (m, 2H). (Z)-isomer: 1.48 (s, 3H), 1.6 (s, 3H), 4.5 (s, 1H), 4.7 (d, 2H), 5.25 (s, 1H), 5.1–6.2 (m, 3H), 6.88 (s, 1H), 7.2–7.5 (m, 1H), 8.43–9.0 (m, 3H). |
| 4-pyridyl | 36 | Ethyl acetate/ hexane (1:1) | Mixed isomers: 1.45 (s, 3H), 1.62 (s, 3H), 4.5 (s, 1H), 4.7 (d, 2H), 5.2–6.2 (m, 4H), 6.75 (s, 0.3H), 7.2–7.5 (m, 1.7H), 7.6–7.85 (m, 1H), 8.5–8.83 (m, 2H). |
| 2-methylthienyl | 14 | CHCl$_3$ | 1.45 (s, 3H), 1.6 (s, 3H), 4.4 (s, 3H), 4.7 (d, 2H), 5.0–6.2 (m, 3H), 5.25 (d, 1H), 7.0–7.65 (m, 4H). |
| CH$_2$=CH— | 18 | CHCl$_3$ | 1.45 (s, 3H), 1.65 (s, 3H), 3.7–4.2 (m, 1H), 4.45 (s, 0.6H), 4.5 (s, 0.4H), 4.75 (d, 2H), 5.1–6.4 (m, 7H). |

EXAMPLE 23

Starting with the allyl 6-R$^3$-methylene-1,1-dioxopenicillanate esters provided in Examples 19-22, the following sodium salts are obtained by the method of Example 17. The corresponding potassium salts are obtained when potassium 2-ethylhexanoate is employed.

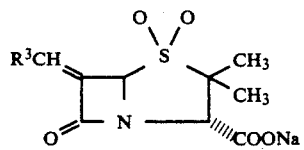

| $R^3$ | Isomer | % Yield | Infrared Spectrum (KBr) | $^1$H-NMR(D$_2$O)ppm(delta): |
|---|---|---|---|---|
| (2-furyl) | 3:1 (E):(Z) | 47 | 1621, 1678 1764, 2979 3402, 3472 cm$^{-1}$ | (250 MHz spectrum): 1.5 (s, 3H), 1.6 (s, 3H), 4.25 (s, 1H), 5.57 (s, 0.25H), 5.9 (s, 0.75H), 6.65 (m, 1H), 7.0 (d, 1H), 7.17 (d, 0.25H), 7.36 (s, 0.75H), 7.78 (m, 1H). |
| (N-acetyl-pyrrolyl) | (E) | 56 | 1622, 1728 1764, 3438 cm$^{-1}$ | (60 MHz spectrum): 1.56 (s, 3H), 1.65 (s, 3H), 2.68 (s, 3H), 4.25 (s, 1H), 5.88 (s, 1H), 6.5 (t, 1H), 7.0 (d, 1H), 7.6–8.0 (m, 1H), 8.2 (s, 1H). |
| $C_6H_5$ | (Z) | 91 | 1565, 1619, 1667, 1759 2950, 3453 cm$^{-1}$ | (60 MHz spectrum): 1.45 (s, 3H), 1.55 (s, 3H), 4.17 (s, 1H), 5.5(s, 1H), 7.0 (s, 1H), 7.27–7.6 (m, 3H), 7.6–8.1 (m, 2H). |
| (3-pyridyl) | (E) | 72 | 1623, 1778, 3462 cm$^{-1}$ | 1.55 (s, 3H), 1.62 (s, 3H), 4.23 (s, 1H), 6.05 (s, 1H), 7.4–8.8 (m, 5H). |
| (3-pyridyl) | (Z) | 91 | 1303, 1623 1761, 3445 cm$^{-1}$ | 1.55 (s, 3H), 1.65 (s, 3H), 4.3 (s, 1H), 5.6 (s, 1H), 6.96 (s, 1H), 7.1–9.0 (m, 4H). |
| (4-pyridyl) | (E) + (Z) | 93 | 1623, 1778 3448 cm$^{-1}$ | 1.5 (s, 3H), 1.6 (s, 3H), 4.3 (s, 0.3H), 5.55 (s, 0.3H), 6.0 (d, 0.7H), 6.95 (s, 0.3H), 7.2–7.8 (m, 4.7H). |
| (2-thienyl) | (E) | 33 | 1619, 1773, 3425 cm$^{-1}$ | 1.55 (s, 3H), 1.60 (s, 3H), 4.2 (s, 1H), 5.8 (s, 1H), 7.0–7.9 (m, 4H). |
| $CH_2=CH-$ | — | 25 | 1620, 1773, 3430 cm$^{-1}$ | 1.59 (s, 3H), 1.60 (s, 3H), 4.22 (s, 0.6H), 4.3 (s, 0.4H), 5.53 (s, 0.4H), 5.75 (s, 0.6H), 5.5–6.2 (m, 3H). |
| (2,6-dimethylpyridyl) (potassium salt) | (E) | 77 | — | 1.5 (s, 3H), 1.6 (s, 3H), 2.5 (s, 3H), 4.28 (s, 1H), 6.05 (d, 1H), 7.2–7.35 (m, 2H), 7.4 (d, 1H), 7.67 (t, 1H). $^{13}$C-NMR(D$_2$O)ppm(delta): 20.719, 22.436, 26.032, 68.386, 68.533, 74.489, 120.794, 128.334, 132.843, 140.670, 152.549, 163.012, 174.041, 175.657. |
| (pyrazinyl) (potassium salt) | (E) | 92 | 1614, 1770, 3406 cm$^{-1}$ | (D$_2$O + DMSO): 1.5 (s, 3H), 1.6 (s, 3H), 4.1 (s, 1H), 5.9 (d, 1H), 7.5 (d, 1H), 8.5–9.0 (m, 3H). |

EXAMPLE 24

6(E)-Phenylmethylenepenicillanic acid-1,1-dioxide

To a solution of 0.1 g (0.28 mmole) allyl 6(E)-phenylmethylene-1,1-dioxopenicillanate, 20 mg triphenylphosphine and 20 mg tetrakis (triphenylphosphine)palladium (O) in 3 ml ethyl acetate was added 0.57 ml of 0.5M sodium 2-ethylhexanoate and the mixture was stirred at room temperature for one hour. After standing for 65 hours in the refrigerator no precipitate had formed. The mixture was diluted with ethyl acetate and water, the separated aqueous layer was adjusted to pH 1.8 with dilute hydrochloric acid, extracted with fresh ethyl acetate, the extracts dried ($Na_2SO_4$) and solvent evaporated in vacuo to give 62 mg (69%) of product as yellow crystals (from acetone). $^1$H-NMR($CD_3COCD_3$)ppm (delta): 1.55 (s, 3H), 1.65 (s, 3H), 4.43 (s, 1H), 5.93 (d, 1H), 7.3–7.9 (m, 6H), 8.7 (bs, 1H); infrared spectrum (KBr) cm$^{-1}$: 1327, 1685, 1737, 1772, 2929, 2961, 3108, 3477.

EXAMPLE 25

Potassium 6(E)-(1-Methylimidazol2-yl)-methylene-1,1-dioxopenicillanate

A. Allyl 6-(1-Methylimidazol-2-yl)acetoxymethyl-1,1-dioxopenicillanate 6-(1-Methylimidazol-2-yl)hydroxymethyl-1,1-dioxopenicillanate (472 mg, 1.23 mmole) was acetylated by the method of Example 20, Part A, to provide 392 mg (75%) of the acetoxy compound as a mixture of two isomers. $^1$H-NMR(CDCl$_3$)ppm (delta) 1.4 (s, 1.5H), 1.5 (s, 1.5), 1.6 (s, 1.5H), 1.7 (s, 1H), 2.2 (s, 3H), 3.7 (s, 1.5H), 3.75 (s, 1.5H), 4.0–6.0 (m, 8H), 6.3–6.5 (m, 1H), 6.8 (m, 1H), 7.0 (m, 1H).

B. Allyl 6(E)-(1-Methylimidazol-2-yl)methylene-1,1-dioxopenicillanate

The product obtained in Part A, above, (392 mg, 0.920 mmole), 5 ml methylene chloride and 0.115 ml 1,5-diazabicyclo[4,3.0]non-5-ene (DBN) was converted to the title ester by the method of Example 20, Part B, in 53% yield $^1$H-NMR(CDCl$_3$)ppm (delta): 1.5 (s, 3H), 1.6 (s, 3H), 3.7 (s, 3H), 4.35 (s, 1H), 4.7 (m, 2H), 5.0–6.1 (m, 3H), 5.7 (d, 1H), 6.9 (m, 1H), 7.1 (d, 1H), 7.2 (m, 1H).

C. The allyl ester obtained in Part B (163 mg, 0.45 mmole) was converted to the title potassium salt by the method of Example 17, but employing potassium 2-ethylhexanoate in place of the corresponding sodium salt. The product obtained amounted to 143 mg (87% yield) of the single (E) isomer. $^1$H-NMR(DMSO)ppm (delta): 1.38 (s, 3H), 1.45 (s, 3H), 3.8 (s, 4H), 5.68 (s, 1H), 7.15 (s, 1H), 7.35 (m, 2H); $^{13}$C-NMR(DMSO)ppm (delta): 18.5, 20.2, 32.5, 64.4, 66.2, 70.55, 115.2, 124.6, 129.9, 130.6, 141.2, 167.9, 169.0. Infrared spectrum (KBr) cmhu $-1$: 1614, 1762, 3428.

EXAMPLE 26

The procedure of Example 10 was repeated with 50 mg (0.12 mmole) allyl 6-(3-allyloxy-2-pyridyl)methylene-1,1-dioxopenicillanate by employing 5.2 mg triphenylphosphine, 5.2 mg tetrakis (triphenylphosphine)palladium (O) and 0.24 mmoles of potassium 2-ethylhexanoate (2 molar equivalents of starting allyl ester) in 1.5 ml ethyl acetate and stirring the resulting mixture for 18 hours. The ethyl acetate was drawn off with a pipette and the residue washed twice with 1 ml portions of ethyl acetate to give a dark solid, 43 mg, which was found to be the dipotassium salt of 6-(E)-(3-hydroxy-2-pyridyl)methylene-1,1-dioxopenicillanic acid. $^1$H-NMR($D_2O$)ppm (delta): 1.56 (s, 3H), 1.62 (s, 3H), 4.27 (s, 1H), 6.00 (d, 1H), 7.29 (m, 2H), 7.80 (d, 1H), 8.04 (d, 1H).

EXAMPLE 27

Allyl 6(E)-(2-pyrimidinyl)methylenepenicillanate

A. 2-Hydroxymethylpyrimidine

A slurry of sodium ethoxide, prepared from 7.44 g (323 mmole) sodium metal and 300 ml absolute ethanol, was cooled to room temperature, 18 g (163 mmole) hydroxyacetamidine hydrochloride and 8.06 ml (81 mmole) 3-dimethylaminoacrolein were added and the mixture heated to reflux. Dimethylamine was distilled off slowly while periodically adding ethanol to maintain the solvent volume. After refluxing for nine hours, the mixture was then stirred at room temperature for 18 hours. The solvent was evaporated under reduced pressure and the residue placed on a silica gel column and eluted with 19:1 ethyl acetate/methanol to afford 4.1 g of product (46% yield).

EXAMPLE 27 (Contd)

B. 2-Pyrimidinylmethyltriphenylphosphonium chloride

2-Hydroxymethylpyrimidine, 4.096 g (37.2 mmole) was dissolved in 80 ml methylene chloride and 8 6 ml (37.2 mmole) thionyl chloride was added dropwise (exothermic). The mixture was stirred for 15 minutes, neutralized with saturated sodium bicarbonate solution and extracted with methylene chloride. The extracts were dried and solvent evaporated to give 3.67 g of 2-chloromethylpyrimidine. $^1$H-NMR(CDCl$_3$)ppm (delta) 4.82 (s, 2H), 7.3 (t, 1H), 8.9 (d, 2H).

A mixture of 3.565 g (27.7 mmole) of 2-chloromethylpyrimidine in 30 ml toluene and 7.269 g (27.7 mmole) triphenylphosphine were heated at reflux for 18 hours. The resulting precipitate was collected by filtration and dried to yield 9.06 g (65% for two steps).

C. A mixture of 2 187 g (5 6 mmole) of the Wittig reagent from Part B, above, 218 4 mg (5.32 mmole) sodium amide and 30 ml dry tetrahydrofuran (THF) was stirred at room temperature for 1.5 hours. A solution of 1.44 9 (5.65 mmole) allyl 6-oxopenicillanate in 10 ml dry THF was added in one portion at $-78°$ C., the resulting mixture stirred for five minutes, poured into saturated ammonium chloride solution and extracted with chloroform. The organic phase was washed with saturated ammonium chloride, brine, dried (MgSO$_4$) and the solvent evaporated in vacuo. The resulting oil was purified by column chromatography on silica gel, eluting with 9:1 chloroform/ethyl acetate to provide 560 mg of the pure product $^1$H-NMR(CDCl$_3$)ppm (delta): 1.5 (s, 3H), 1.6 (s, 3H), 4.6 (s, 1H), 4.7 (m, 2H), 5.1–6.3 (m, 3H), 6.2 (d, 1H), 7.0 (d, 1H), 7.0–7.35 (m, 1H), 8.8 (d, 2H).

EXAMPLE 28

Allyl Ester of 1,1-Dioxo-6(E)-(2-pyrimidinylmethylenepenicillanic Acid and Potassium Salt A. Allyl 6(E)-(2-pyrimidinyl)-methylenepenicillanate (560 mg, 1 69 mmole) and 3-chloroperbenzoic acid 730 mg (3.38 mmole) were dissolved in 10 ml methylene chloride and stirred under a nitrogen atmosphere four hours. The resulting mixture was quenched with water, extracted with methylene chloride, the extracts were washed with sodium thiosulfate, neutralized with sodium bicarbonate, washed with brine, dried and concentrated in vacuo to give 460 mg of crude oil. The oil was purified by silica gel column chromatography, eluting with 9:1 chloroform/ethyl acetate to afford 180 mg of the desired allyl ester as a pale yellow solid. $^1$H-NMR(CDCl$_3$)ppm (delta): 1.45 (s, 3H), 1.65 (s, 3H), 4.5 (s, 1H), 4.75 (m, 2H), 5.2–6.3 (m, 3H), 5.75 (s, 1H), 7.1–7.5 (m, 2H), 8.9 (d, 2H).

B. Reaction of the above allyl ester with triphenyl phosphine, tetrakis (triphenylphosphine)palladium (O) and potassium 2-ethyl hexanoate by the method of Example 10 gave the desired potassium salt in 89% yield as a pale pink solid. $^1$H-NMR(D$_2$O)ppm (delta) 1.6 (s, 3H), 1.68 (s, 3H), 4.4 (s, 1H), 6.1 (s, 1H), 7.48 (s, 1H), 7.54 (t, 1H), 8.88 (d, 2H); $^{13}$C-NMR(D$_2$O)ppm (delta): 20.9, 22.7, 68.8, 68.9, 74.6, 124.5, 132.5, 139.9, 160.9, 163.2, 172.5, 175.5. Infrared spectrum (KBr) cm$^{-1}$: 1560, 1615, 1771, 3439.

EXAMPLE 29

Reaction of 6-alpha-hydroxypenicillanic acid with the appropriate halide of formula R$^1$X, where X is Cl, Br, I, OSO$_2$CH$_3$ or diazo, by the procedure of Example 1 affords the following esters:

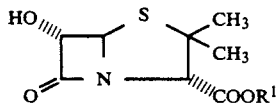

R$^2$ 3-phthalidyl
4-crotonolactonyl
gamma-butyrolacton-4-yl
acetoxymethyl
n-hexanoyloxymethyl
1-(acetoxy)ethyl
1-(isobutyryloxy)ethyl
1-(2-methylvaleryloxy)ethyl
1-methyl-1-(acetoxy)ethyl
1-methyl-1-(hexanoyloxy)ethyl
methoxycarbonyloxymethyl
propoxycarbonyloxymethyl
1-(ethoxycarbonyloxy)ethyl
1-(butoxycarbonyloxy)ethyl
1-methyl-1-(methoxycarbonyloxy)ethyl
1-methyl-1-(ethoxycarbonyloxy)ethyl
1-methyl-1-(hexanoyloxycarbonyloxy)ethyl
4-nitrobenzyl
benzhydryl
t-butyl
2,2,2-trichloroethyl
phenacyl

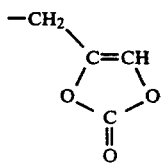

EXAMPLE 30

A. To 1.0 g 6-alpha-hydroxypenicillanic acid in 25 ml methylenechloride is added 50 mg diisopropylcarbodiimide and 0.5 ml 2,2,2-trichloroethanol. The mixture is stirred overnight, the solvent removed by evaporation in vacuo and the crude product purified by column chromatography on silica gel to afford 2,2,2-trichloroethyl 6-alpha-hydroxypenicillanate.

B. To 1.0 g 6-alpha-hydroxypenicillanic acid in 50 ml dioxane is added 0.5 g p-toluene sulfonic acid and 0.4 g dihydropyran and the mixture warmed to 50° C., then stirred overnight at room temperature. Evaporation of solvent and purification by silica gel column chromatography affords 2-tetrahydropyranyl 6-alphahydroxypenicillanate.

EXAMPLE 31

Benzyl 6-oxopenicillanate

To a solution of 1 8 ml (0.025 mole) dimethylsulfoxide in 2 ml methylene chloride at −60° C. was added dropwise a solution of 2.12 ml (0.015 mole) trifluoroacetic anhydride in 5 ml methylene chloride. The mixture was stirred at −60° C. for 20 minutes, a solution of 350 mg (1.14 mmole) benzyl 6-alpha-hydroxypenicillanate in 5 ml methylene chloride added and stirring continued at −60° C. for 60 minutes. Triethylamine (0.50 ml) was added, the cooling bath removed, the mixture warmed to 0° C., poured into ice-water and extracted with methylene chloride. The organic layer was dried, concentrated in vacuo to a small volume which was diluted with benzene and washed three times with ice-water. The benzene layer was dried, solvent evaporated in vacuo to yield 230 mg (67%) of product as yellow crystals. The proton-NMR spectrum in CDCl$_3$ showed the product to be very pure.

EXAMPLE 31 (Contd)

When the remaining 6-alpha-hydroxypenicillanate esters provided in Examples 1, 29 and 30 are oxidized by the above procedure, the corresponding compounds of the formula below are obtained wherein R$^1$ is as defined for the starting 6-hydroxypenicillanate ester.

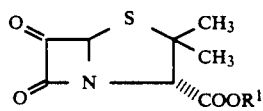

EXAMPLE 32

Benzyl 6-(4-Methoxyphenyl)methylenepenicillanate

A mixture of 2.09 g (5.0 mmole) 4-methoxybenzyltriphenylphosphonium chloride, 0.195 g (5.0 mmole) sodium amide and 5 ml dry tetrahydrofuran (THF) is stirred at room temperature for 20 minutes, then cooled to −78° C. A solution 1 84 g (6.0 mmole) benzyl 6-oxopenicillanate in 4 ml dry THF is added and the mixture stirred for 10 minutes at −78° C. The reaction was quenched with saturated ammonium chloride solution, extracted with ethyl acetate, the extracts washed with water, dried and the solvent evaporated to afford a crude product which is purified by column chromatography on silica gel.

EXAMPLE 33

By employing the appropriate Wittig reagent of formula R$^3$CH=P(C$_6$H$_5$)$_3$ and the appropriate ester of 6-oxopenicillanic acid, selected from those provided in Example 31, in the procedure of the preceding Example affords the compounds of the formula

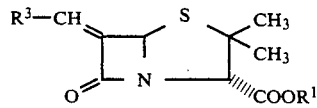

where R¹ and R³ are as defined below.

| R¹ | R³ |
|---|---|
| benzyl | CH$_2$=CH— |
| benzhydryl | CH$_3$S |
| 2-tetrahydropyranyl | (CH$_3$)$_2$CHS |
| allyl | n-C$_4$H$_9$S |
| t-butyl | t-C$_4$H$_9$S |
| 2,2,2-trichloroethyl | CH$_3$SO$_2$ |
| phenacyl | 2-furyl |
| allyl | 3-furyl |
| benzyl | 2-thienyl |
| benzhydryl | 3-thienyl |
| t-butyl | N-methylpyrrol-3-yl |
| 2-tetrahydropyranyl | N-acetylpyrrol-2-yl |
| 2,2,2-trichloroethyl | C$_6$H$_5$ |
| 3-phthalidyl | 4-CH$_3$C$_6$H$_4$ |
| 4-crotonolactonyl | 4-C$_2$H$_5$C$_6$H$_4$ |
| gamma-butyrolacton-4-yl | 3-n-C$_3$H$_7$C$_6$H$_4$ |
| 3-phthalidyl | 4-t-C$_4$H$_9$C$_6$H$_4$ |
| 4-crotonolactonyl | 4-CH$_3$OC$_6$H$_4$ |
| acetoxymethyl | 3-i-C$_4$H$_9$OC$_6$H$_4$ |
| n-butyrylmethyl | 2-C$_2$H$_5$OC$_6$H$_4$ |
| n-hexanoyloxy | 3-CH$_2$=CHCH$_2$OC$_6$H$_4$ |
| 1-(acetoxy)ethyl | 4-HOC$_6$H$_4$ |
| 1-(isobutyryloxy)ethyl | 2-(COOH)C$_6$H$_4$ |
| 1-(2-methyl-valeryloxy)ethyl | 4-(CH$_3$OCO)C$_6$H$_4$ |
| 1-methyl-1-(acetoxy)ethyl | 3-(n-C$_4$H$_9$OCO)C$_6$H$_4$ |
| 1-methyl-1-(hexanoyloxy)ethyl | 2-(CH$_3$CO)C$_6$H$_4$ |
| methoxycarbonyloxymethyl | 4-(i-C$_3$H$_7$CO)C$_6$H$_4$ |
| propoxycarbonyloxymethyl | 3-(n-C$_4$H$_9$CO)C$_6$H$_4$ |
| 1-(ethoxycarbonyloxy)ethyl | 4-NH$_2$C$_6$H$_4$ |
| 1-(butoxycarbonyloxy)ethyl | 4-(CH$_3$)$_2$NC$_6$H$_4$ |
| 1-methyl-1-(methoxycarbonyloxy)ethyl | 3-(C$_2$H$_5$)$_2$NC$_6$H$_4$ |
| 1-methyl-1-(ethoxycarbonyloxy)ethyl | 3-(t-C$_4$H$_9$NHC$_6$H$_4$ |
| 1-methyl-1-(hexanoyloxycarbonyloxy)ethyl | 4-C$_6$H$_5$NHC$_6$H$_4$ |
| benzyl | 4-n-C$_3$H$_7$N(CH$_3$)C$_6$H$_4$ |
| benzhydryl | 3-C$_6$H$_5$—CH$_2$N(CH$_3$)C$_6$H$_4$ |
| t-butyl | 2-NH$_2$COC$_6$H$_4$ |
| 2,2,2-trichloroethyl | 2-CH$_3$NHCOC$_6$H$_4$ |
| phenacyl | 4-(CH$_3$)$_2$NCOC$_6$H$_4$ |
| allyl | 3-C$_6$H$_5$N(C$_2$H$_5$)COC$_6$H$_4$ |
| allyl | 4-C$_6$H$_5$CH$_2$NHCOC$_6$H$_4$ |
| allyl | 3-CH$_3$CONHC$_6$H$_4$ |
| allyl | 4-(CH$_3$)$_2$CHCONHC$_6$H$_4$ |
| allyl | 2-CF$_3$CONHC$_6$H$_4$ |
| allyl | 3-C$_6$H$_5$CONHC$_6$H$_4$ |
| pivaloyloxymethyl | 4-n-C$_4$H$_9$CONHC$_6$H$_4$ |
| pivaloyloxymethyl | C$_6$H$_5$S |
| pivaloyloxymethyl | 4-CH$_3$C$_6$H$_4$S |
| 4-crotonolactonyl | 4-CH$_3$OC$_6$H$_4$S |
| 4-crotonolactonyl | 2-NO$_2$C$_6$H$_4$S |
| 4-crotonolactonyl | 3-ClC$_6$H$_4$S |
| 4-crotonolactonyl | 4-CF$_3$C$_6$H$_4$S |
| 4-crotonolactonyl | 4-BrC$_6$H$_4$S |
| 4-crotonolactonyl | 4-CH$_2$=CHCH$_2$OC$_6$H$_4$S |
| 3-phthalidyl | 4-CH$_3$OCOC$_6$H$_4$S |
| 3-phthalidyl | 4-C$_2$H$_3$—COC$_6$H$_4$S |
| 3-phthalidyl | 3-(CH$_3$)$_2$NC$_6$H$_4$S |
| 3-phthalidyl | 4-(CH$_3$)$_2$NCOC$_6$H$_4$S |
| 3-phthalidyl | 3-C$_6$H$_5$NHCOC$_6$H$_4$S |
| 3-phthalidyl | 4-CH$_3$CONHC$_6$H$_4$S |
| 2-tetrahydropyranyl | 3-CF$_3$CONHC$_6$H$_4$S |
| 2-tetrahydropyranyl | 4-CHSC$_6$H$_4$S |
| 2-tetrahydropyranyl | 3-t-C$_4$H$_9$SC$_6$H$_4$S |
| 2-tetrahydropyranyl | 4-C$_6$H$_5$CH$_2$SC$_6$H$_4$S |
| 2-tetrahydropyranyl | 2-pyridyl |
| 2-tetrahydropyranyl | 3-pyridyl |
| gamma-butyrolacton-4-yl | 1-oxo-3-pyridyl |
| gamma-butyrolacton-4-yl | 5-methyl-1-oxo-2-pyridyl |
| gamma-butyrolacton-4-yl | 5-ethyl-1-oxo-3-pyridyl |
| gamma-butyrolacton-4-yl | 5-n-butyl-2-pyridyl |
| gamma-butyrolacton-4-yl | 4-hydroxy-2-pyridyl |
| gamma-butyrolacton-4-yl | 2-hydroxy-4-pyridyl |
| 2,2,2-trichloroethyl | 3-hydroxy-2-pyridyl |
| 2,2,2-trichloroethyl | 4-hydroxy-1-oxo-2-pyridyl |
| 2,2,2-trichloroethyl | 4-allyloxy-3-pyridyl |
| 2,2,2-trichloroethyl | 5-allyloxy-2-pyridyl |
| 2,2,2-trichloroethyl | 4-carboxy-2-pyridyl |
| 2,2,2-trichloroethyl | 4-methoxycarbonyl-2-pyridyl |
| phenacyl | 3-carboxy-1-oxo-2-pyridyl |
| phenacyl | 4-isobutoxycarbonyl-2-pyridyl |
| phenacyl | 5-acetyl-3-pyridyl |
| phenacyl | 5-acetyl-1-oxo-2-pyridyl |
| phenacyl | 4-n-butyryl-1-oxo-2-pyridyl |
| phenacyl | 2-ethoxycarbonyl-3-pyridyl |
| t-butyl | 4-dimethylamino-2-pyridyl |
| t-butyl | 4-diethylamino-1-oxo-2-pyridyl |
| t-butyl | 4-carboxamido-2-pyridyl |
| t-butyl | 4-(N-methylcarboxamido)-2-pyridyl |
| t-butyl | 5-(N,N-diethylcarboxamido)-2-pyridyl |
| t-butyl | 4-acetylamino-3-pyridyl |
| benzhydryl | 2-n-butylcarbonylamino-4-pyridyl |
| benzhydryl | 4-nitro-2-pyridyl |
| benzhydryl | 3-chloro-2-pyridyl |
| benzhydryl | 4-bromo-1-oxo-3-pyridyl |
| benzhydryl | 4-trifluoromethyl-2-pyridyl |
| benzhydryl | 4-methylthio-2-pyridyl |
| benzyl | 4-benzylthio-3-pyridyl |
| benzyl | 5-methylquinolin-2-yl |
| benzyl | 5-methyl-1-oxoquinolin-2-yl |
| benzyl | 1-isoquinolyl |
| benzyl | 3-isoquinolyl |
| benzyl | 2-oxo-isoquinolin-1-yl |
| allyl | 2-oxo-isoquinolin-3-yl |
| allyl | 4-isoquinolyl |
| allyl | 6-isoquinolyl |
| allyl | 2-oxo-6-isoquinolyl |
| allyl | 4-allyloxyquinolin-2-yl |
| allyl | 4-hydroxyquinolin-2-yl |
| allyl | N-methylindol-2-yl |
| allyl | 3-methylpyrazin-2-yl |
| allyl | 5-methylpyrazin-2-yl |
| allyl | 6-ethylpyrazin-2-yl |
| allyl | 3-ethylpyrazin-2-yl |
| allyl | 5,6-dimethylpyrazin-2-yl |
| allyl | 4-methylpyrimidin-2-yl |
| allyl | 2-methylpyrimidin-4-yl |
| allyl | 2-ethylpyrimidin-4-yl |
| allyl | 5,6-dimethylpyrimidin-2-yl |
| allyl | 4,6-diethylpyrimidin-2-yl |
| allyl | 2,6-dimethylpyrimidin-4-yl |
| allyl | 1-methylimidazol-2-yl |
| allyl | imidazol-4-yl |
| allyl | 2-methylimidazol-4-yl |
| allyl | 5-ethylimidazol-2-yl |
| allyl | 1,5-dimethylimidazol-2-yl |
| allyl | 1,2-diethylimidazol-4-yl |
| allyl | thiazol-2-yl |
| (2-oxo-1,3-dioxolen-4-yl)methyl | 1-oxo-2-pyridyl |
| (5-methyl-2-oxo-1,3-dioxolen-4-yl)methyl | thiazol-2-yl |
| (5-methyl-2-oxo-1,3-dioxolen-4-yl)methyl | CH$_2$N(CH$_3$)$_2$ |
| allyl | CH(CH$_3$)NHCH$_2$CH$_2$OH |
| allyl | CH$_2$N(CH$_2$CH$_2$OH)$_2$ |
| allyl | CH$_2$NHCH$_2$CH(OH)CH$_3$ |

-continued

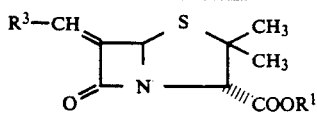

where $R^1$ and $R^3$ are as defined below.

| $R^1$ | $R^3$ |
|---|---|
| allyl | $CH_2N(CH_3)CH_2(CH_2)_2CH_2OH$ |
| allyl | pyrrolidinomethyl |
| allyl | piperidinomethyl |
| allyl | morpholinomethyl |
| allyl | thiomorpholinomethyl |
| allyl | 4-methylpiperazinomethyl |
| allyl | —C(=S)—NH₂ |
| allyl | —C(=S)—NHCH₃ |
| allyl | —C(=S)—NHC₆H₅ |
| allyl | —C(=S)—NHCH₂C₆H₅ |
| allyl | —C(=S)—NHCH₂CH(CH₃)₂ |
| allyl | —C(=S)—N(C₂H₅)₂ |
| allyl | 1-methyl-imidazolin-2-yl |
| allyl | imidazolin-2-yl (NH) |
| allyl | 1-ethyl-tetrahydropyrimidin-2-yl |
| allyl | 1-acetyl-tetrahydropyrimidin-2-yl |
| allyl | 3-ethyl-1,2,4-triazol-5-yl |
| allyl | 3-methyl-isothiazol-5-yl |

-continued

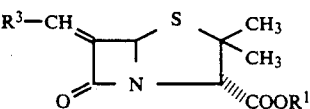

where $R^1$ and $R^3$ are as defined below.

| $R^1$ | $R^3$ |
|---|---|
| allyl | 5-ethyl-3-methyl-isothiazol-... |
| allyl | 3-acetyl-isothiazol-5-yl |
| allyl | 4-methyl-isoxazol-3-yl |
| allyl | 3-methyl-isoxazol-5-yl |
| allyl | 3,5-dimethyl-1,2,4-thiadiazol-yl |
| benzyl | 3-ethyl-5-methyl-1,2,4-thiadiazol-yl |
| benzyl | 3-acetyl-5-methyl-1,2,4-thiadiazol-yl |
| benzyl | 2-ethyl-5-methyl-1,3,4-oxadiazol-yl |
| benzyl | 2-acetyl-5-methyl-1,3,4-oxadiazol-yl |
| benzyl | 4-methyl-1,2,3-thiadiazol-5-yl |

-continued
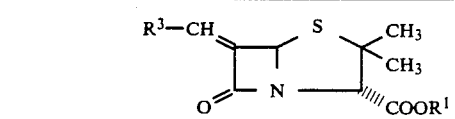
where R¹ and R³ are as defined below.
| R¹ | R³ |
|---|---|
| benzyl | 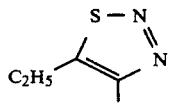 |
| allyl | 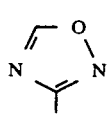 |
| allyl | 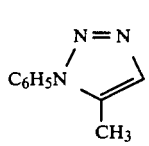 |
| allyl | 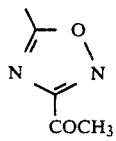 |
| allyl | 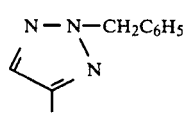 |
| allyl | 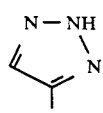 |
| allyl | 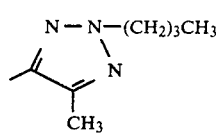 |
| allyl | 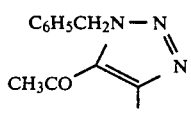 |
| pivaloyloxymethyl | 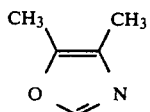 |
| pivaloyloxymethyl | 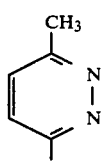 |
-continued
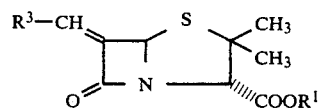
where R¹ and R³ are as defined below.
| R¹ | R³ |
|---|---|
| pivaloyloxymethyl | 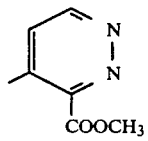 |
| allyl | 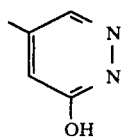 |
| allyl | 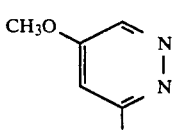 |
| allyl | 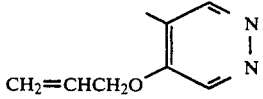 |
| allyl | 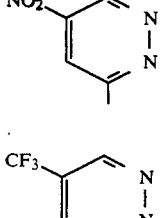 |
| allyl | 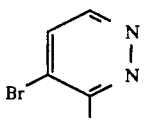 |
| allyl | 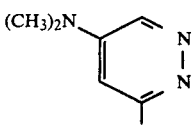 |
| allyl | 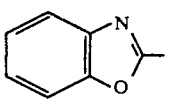 |
| allyl | 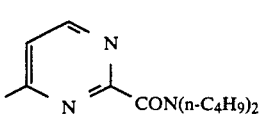 |

-continued
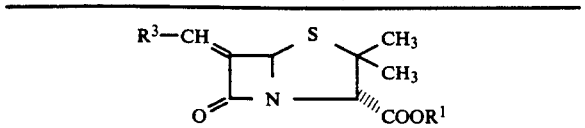
where R¹ and R³ are as defined below.
| R¹ | R³ |
|---|---|
| allyl | 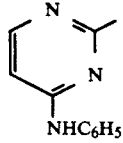 |
| allyl | 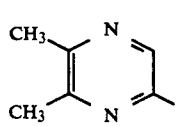 |
| allyl | 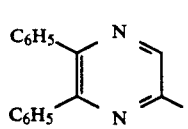 |
| allyl | 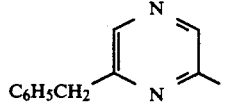 |
| allyl | 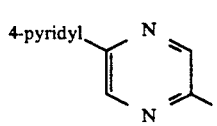 |
| allyl | 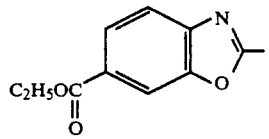 |
| allyl | 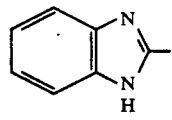 |
| allyl | 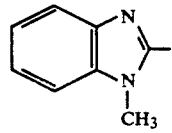 |
| allyl | 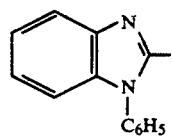 |
| allyl | 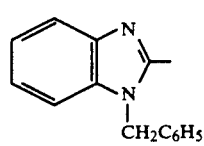 |
-continued
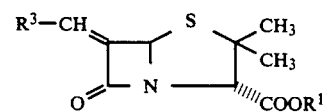
where R¹ and R³ are as defined below.
| R¹ | R³ |
|---|---|
| allyl | 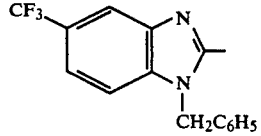 |
| allyl | 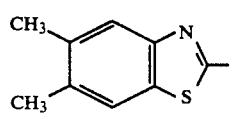 |
| allyl | 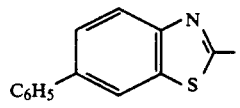 |
| allyl | 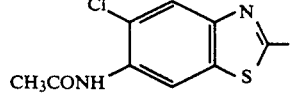 |
| allyl | 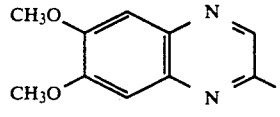 |
| allyl | 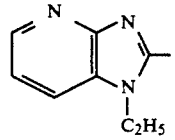 |
| allyl | 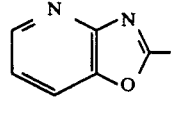 |
| allyl | 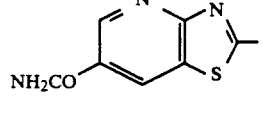 |
| allyl | 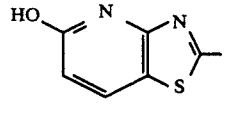 |
| allyl | 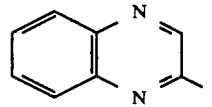 |
| allyl | 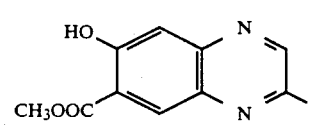 |

-continued

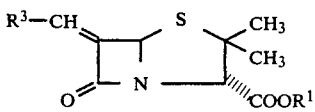

where R¹ and R³ are as defined below.

| R¹ | R³ |
|---|---|
| allyl | 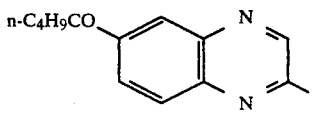 |
| allyl | 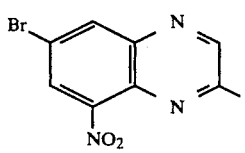 |
| allyl | 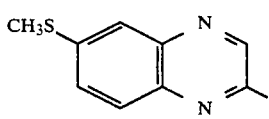 |
| allyl | 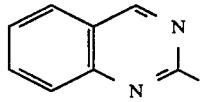 |
| allyl | 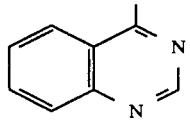 |
| allyl | 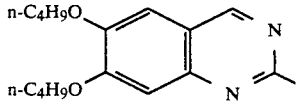 |
| allyl | 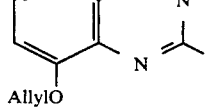 |
| allyl | 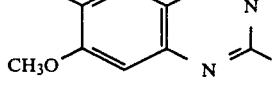 |
| allyl | 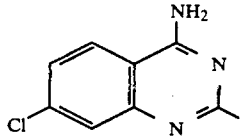 |
| allyl | 4,5-Diethyl-1,2-4-triazol-3-yl |
| allyl | 4-Acetyl-3-thiomethyl-1,2,4-triazol-5-yl |
| allyl | 3-Amino-1,2,4-triazol-5-yl |
| allyl | 5-Dimethylaminocarbonyl-1,2,4-triazin-3-yl |
| allyl | 4-Methyl-3-trifluoromethyl-1,2,4-triazin-5-yl |
| allyl | 1-Phenyltetrazol-5-yl |
| allyl | 1-Benzyltetrazol-5-yl |
| allyl | 1-Allyltetrazol-5-yl |
| allyl | 1-(3-Furyl)methyltetrazol-5-yl |

-continued

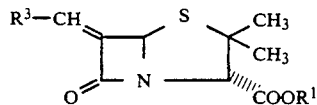

where R¹ and R³ are as defined below.

| R¹ | R³ |
|---|---|
| allyl | 1-(3-Thienyl)methyltetrazol-5-yl |
| allyl | 1-(2-Thienyl)methyltetrazol-5-yl |
| allyl | 1-(2-Phenylthio)ethyltetrazol-5-yl |

EXAMPLE 34

Oxidation of benzyl 6-(4-methoxyphenyl)methylenepenicillanate with an equimolar amount of m-chloroperbenzoic acid in ethyl acetate at room temperature by the method of Example 7 affords a mixture of the alpha- and beta-sulfoxides.

In like manner the remaining products provided in Example 33 are reacted with an equimolar amount of m-chloroperbenzoic acid in methylene chloride, chloroform, ethyl acetate or acetonitrile as solvent to provide the corresponding sulfoxides of the formula

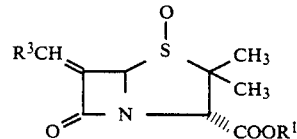

where R¹ and R³ are as defined for the starting 6-methylenepenicillanate ester.

EXAMPLE 35

Benzyl 6-(4-methoxyphenyl)methylene-1,1-dioxopenicillanate

To a solution of 2 g (4.8 mmole) of benzyl 6-(4-methoxyphenyl)methylenepenicillanate in 200 ml acetone is added 20 ml water and the pH of the mixture is adjusted to 4.0 with phosphoric acid. Then 1.58 g (10 mmole) of powdered potassium permanganate is added and the mixture is stirred at room temperature for 2 hours. The mixture is partitioned between ethyl acetate and water at pH 2.0 and sodium bisulfite is added to consume the excess oxidant. The organic layer is separated, the aqueous layer extracted with ethyl acetate, and the combined organic layers are washed with brine and dried (Na₂SO₄). The solvent is then evaporated in vacuo and the residue purified by column chromatography on silica gel to obtain the pure title compound.

Oxidation of the same starting material (0.01 mole) in 100 ml acetone as solvent with a molar excess of 30% hydrogen peroxide in the presence of 1 ml of 0.5M sodium tungstate, heating the mixture at reflux for two hours and evaporation of solvent affords the above crude product which is also purified by silica gel chromatography.

EXAMPLE 36

6-(4-Methoxyphenyl)methylene-1,1-dioxopenicillanic acid

To a solution of 4 5 g (0.01 mole) benzyl 6-(4-methoxyphenyl)methylene-1,1-dioxopenicillanate in 40 ml methanol and 40 ml ethyl acetate is added 1.0 g 10% palladium-on-carbon catalyst and the mixture is shaken at 3.5 kg/cm² hydrogen pressure for one hour. The catalyst is removed by filtration washing with methanol and the filtrate and washings are evaporated to dryness.

EXAMPLE 37

Oxidation of the remaining products provided in Example 33 with a molar excess of m-chloroperbenzoic acid, potassium permanganate or hydrogen peroxide by one of the procedures of Examples 7, 34 or 35 affords the corresponding sulfone of the formula

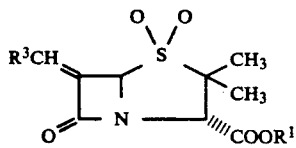

wherein $R^1$ and $R^3$ are as defined in Example 33.

EXAMPLE 38

6-(Pyrazin-2-yl)methylene-1,1-dioxopenicillanic acid

To a mixture of 1.37 g (3 mmole) 2,2,2-trichloroethyl 6-(pyrazin-2-yl)methylene-1,1-dioxopenicillanate in 30 ml tetrahydrofuran (THF) is added 5.6 g zinc powder and 5.6 ml 1M potassium dihydrogenphosphate. The mixture is stirred for 15 minutes at room temperature, filtered, and the filter cake washed with THF/water. The filtrate and washings are combined and the THF evaporated. The aqueous residue is extracted with ethyl acetate. The aqueous phase is adjusted to pH 2.5 and extracted again with fresh ethyl acetate. The combined ethyl acetate layers are washed with brine, dried (Na₂SO₄) and the solvent evaporated in vacuo. The residue is taken up in fresh ethyl acetate and treated with sodium 2-ethylhexanoate by the method of Example 5 to provide the corresponding sodium salt.

EXAMPLE 39

The compounds provided above in Examples 33–37 wherein $R^1$ is a carboxy protecting group, i.e. benzhydryl, 2-tetrahydropyranyl, and t-butyl, are each treated under mild acid or alkaline hydrolysis conditions to provide the corresponding carboxylic acid of the formula

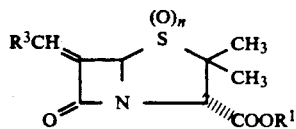

wherein $R^3$ and n are as defined for the starting compound.

Similarly, carboxylic acids of the above formula are obtained from compounds provided in Examples 33–37 wherein $R^1$ is phenacyl by treatment with a molar excess of sodium thiophenoxide in a polar organic solvent.

The carboxylic acids of the above formula are likewise obtained from the benzyl or 4-nitrobenzyl esters provided in Examples 33–37 by hydrogenolysis in the presence of a palladium-on-carbon catalyst, in the presence of methanol, ethanol or ethyl acetate as solvent and at a hydrogen pressure of from one to ten atmospheres. The resulting carboxylic acid is isolated by filtration to remove catalyst and evaporation of solvent.

EXAMPLE 40

Benzyl 6-(2-pyridyl)hydroxymethylpenicillanate

A. Benzyl 6-bromo-6(2pyridyl)hydroxymethypenicillanate

A solution of 9.0 g (0.02 mole) benzyl 6,6-dibromopenicillanate in 200 ml freshly distilled toluene is cooled to −78° C. and 9 ml of 2.2M t-butyllithium in pentane was added dropwise. The resulting mixture was stirred for 30 minutes, 2.14 g (0.02 mole) 2-pyridinecarboxaldehyde was added and stirring continued for another 40 minutes. The reaction was quenched by dropwise addition of acetic acid in toluene. After stirring for one hour the cooling bath was removed, the mixture warmed to −10° C., diluted with 200 ml toluene, washed with water (5 times) and dried (Na₂SO₄). The toluene solution was charged to a column of Florisil (1 Kg.) and eluted with 2:1 toluene/ethyl acetate. The product fractions were combined and evaporated in vacuo to a brown syrup, 4.2 g, which was used in the next step. B. The brown syrup from Part A (4.2 g) was dissolved in 50 ml benzene and 2.65 g tributyltin hydride was added. The mixture was heated at reflux for 2 hours, additional tributyltin hydride (1.65 g) was added and heating at reflux continued overnight. The solvent was evaporated in vacuo, the residue washed with hexane and charged to a column containing 500 g silica gel, and eluted with 2:1 toluene/ethyl acetate to obtain 425 mg of the title compound. ¹H-NMR(CDCl₃)ppm (delta): 1.35 (s, 3H), 1.7 (s, 3H), 4.0 (dd, 1H), 4.5 (s, 1H), 5.1 (s, 2H), 5.2 (d, 1H), 5.4 (d, 1H), 7.0–7.8 (m, 3H), 8.5 (m, 1H).

EXAMPLE 41

6-(2-Pyridyl)hydroxymethylpenicillanic acid 1,1-dioxide

A. Benzyl 6-(2-pyridyl)hydroxymethyl-1,1-dioxopenicillanate

To a solution of 0.40 g benzyl 6-(2-pyridyl)hydroxymethylpenicillanate in 5 ml methylene chloride was added 0.20 g m-chloroperbenzoic acid and the mixture stirred at room temperature for one hour. Thin-layer chromatography indicated the mixture to contain some sulfoxide. An additional 0.2 g m-chloroperbenzoic acid was added and the mixture stirred overnight. The mixture was diluted with methylene chloride, washed in turn with saturated sodium thiosulfate solution, water, saturated sodium bicarbonate solution and the organic layer was concentrated in vacuo. The residue was taken up in ethyl acetate, washed with sodium bicarbonate solution, water, brine, and dried (Na₂SO₄). Evaporation of solvent gave 330 mg of the desired benzyl ester as a brown oil which was purified by silica gel column chromatography, eluting with 11:9 ethyl acetate/hexane to afford 60 mg of yellow oil. ¹H-NMR(CDCl₃)ppm (delta): 1.25 (s, 3H), 1.52 (s, 3H), 4.1 (dd, 1H), 4.5 (s, 1H), 4.72 (d, 1H), 5.5 (d, 2H), 5.8 (d, 1H), 7.1–8.0 (m, 3H), 8.5 (m, 1H).

B. A suspension of 118 mg 10% Pd/C catalyst in 10 ml tetrahydrofuran (THF) and 4 ml water was prehydrogenated for 20 minutes at 3 atmospheres hydrogen pressure. To this was added 130 mg of the benzyl ester obtained in Part A, above, in 4 ml of the same THF/water mixture. This was hydrogenated at 50 psi (3.5 km/cm²) for 30 minutes. An additional 129 mg of 10% Pd/C was added and hydrogenation continued at 50 psi for two hours. The catalyst was removed by filtration, the sovlent evaporated in vacuo and the residue partitioned between water and ethyl acetate. The aqueous layer was freeze dried to give 85 mg of the desired acid. $^1$H-NMR(D$_2$O)ppm (delta): 1.3 (s, 3H), 1.5 (s, 3H), 4.4 (s, 1H), 5.0–5.35 (m, 2H), 5.9 (d, 1H); infrared spectrum (KBR) cm$^{-1}$: 1620, 1731 3407.

C. When the above procedure is carried out, but employing only a total of 175 mg of m-chloroperbenzoic acid (an equimolar amount) in Part A, the product isolated is a mixture of corresponding alpha- and beta-sulfoxides.

EXAMPLE 42

The following materials are blended to obtain a powder of uniform composition in the proportions by weight indicated below:

| (a) | Potassium (6-alpha, 8R)-6-(thiazol-2-yl)acetoxymethyl-1,1-dioxopenicillanate | 1.0 |
|---|---|---|
| (b) | Ampicillin trihydrate | 1.0 |
| (c) | Lactose | 0.5 |
| (d) | Polyethylene glycol, average molecular weight, 4000 | 3.0 |

Blend (1375 mg) is filled into suitably sized hard gelatin capsules to obtain capsules of 250 mg potency of each active ingredient. Higher or lower potency capsules are prepared by appropriate adjustment of capsule size and fill weight. The relative weights of active ingredients are adjusted to obtain capsules wherein the weight ratio of active ingredients is other than one, e.g., the ingredients are blended in a weight ratio of 0.75, 1.5, 0.5 and 3.0, respectively, with a 1700 mg fill weight/capsule to obtain capsules having 225 mg potency of (a) and 450 mg potency of (b).

In like manner, the other beta-lactamase inhibitors of the present invention are formulated with other conventional beta-lactam antibiotics for oral use.

Alternatively, ingredients (a) and (b) in the above formulation are replaced by 2 parts by weight of 6-[D-(2-amino-2-phenylacetamido)]penicillanoyloxymethyl 6-(2-pyridyl)methylene-1,1-dioxopenicillanate hydrochloride.

EXAMPLE 43

Injectable Preparation

Equal parts by weight of cefoperazone sodium and potassium 1,1-dioxo-6(E)-(2-pyrazinyl)methylenepenicillanate are combined with 20 parts by weight of water. Using methods standard in the pharmaceutical art, the solution is sterile filtered, filled into vials, the vials loosely rubber stoppered, and the vials freeze dried on trays. The fill volume is such that each freeze dried vial, now sealed under vacuum, will contain 500 mg of each active ingredient. Prior to injection, each vial is made up by injection of 10 ml of sterile water for injection, through the rubber plug, and shaken to dissolve. The solution to be injected 1–10 ml is removed through the rubber plug via hypodermic needle.

EXAMPLE 44

Allyl 6-(2-thiazolyl)acetoxymethyl-1,1-dioxopenicillanate

Acetylation of 0.5 g (1.29 mmole) allyl 6-(2-thiazolyl)hydroxymethyl-1,1-dioxopenicillanate (provided in Example 18) with 0.396 g (3.88 mmole) acetic anhydride and 0.307 g (3.88 mmole) pyridine in 5 ml tetrahydrofuran was carried out by the method of Example 20, Part A, stirring at room temperature four hours. The mixture was then diluted with methylene chloride, washed with water until neutral (pH 6.0–6.5), the organic phase dried (Na$_2$SO$_4$) and the solvent evaporated to afford 0.688 g of the desired acetate. $^1$H-NMR(CDCl$_3$)ppm(delta): 1.52 (s, 3H), 1.70 (s, 3H), 2.35 (s, 3H), 4.4–4.6 (m, 2H), 4.6–5.0 (m, 3H), 5.2–6.4 (m, 3H), 6.65 (d, 1H), 7.4 (d, 1H), 7.8 (d, 1H).

EXAMPLE 45

Allyl 6-(2-thiazolyl)methylene-1,1-dioxopenicillanate and its Hydrolysis to Potassium Salt A. The above acetoxy ester (0.688 g, 1.29 mmole) was mixed with 0.16 g (1.29 mmole) 1,5-diazabicyclo[4.3.0]-non-5-ene (DBN) and 5 ml methylene chloride and stirred for one hour at room temperature. The resulting mixture was diluted with methylene chloride, washed with water (2×50 ml), dried (Na$_2$SO$_4$) and the solvent evaporated to give an oil. This was chromatographed on a silica gel column, eluting with 1:1 ethyl acetate/hexane to yield 0.189 g (39%) of light yellow oil $^1$H-NMR(CDCl$_3$)-ppm(delta): 1.53 (s, 3H), 1.65 (s, 3H), 4.33 (s, 1H), 4.55 (d, 2H), 5.0–5.4 (m, 2H), 5.45 (s, 1H), 5.4–6.0 (m, 1H), 7.1 (m, 1H), 7.75 (m, 1H), 7.65 (d, 1H).

B. Hydrolysis of the allyl ester obtained above by the method of Example 25, Part C afforded potassium 6-(2-thiazolyl)methylene-1,1-dioxopenicillanate in 84.7% step yield as a yellow solid $^1$H-NMR 250 MHz (DMSO-D$_6$)ppm(delta): 1.40 (s, 3H), 1.45 (s, 3H), 3.80 (s, 1H), 5.83 (s, 1H), 7.66 (s, 1H), 8.04 (m, 2H).

EXAMPLE 46

Acylation of the 6-R$^{13}$-substituted)hydroxymethyl-1,1-dioxopenicillanate esters provided in Examples 15 and 18 with the appropriate acid anhydride or acid chloride by the method of Example 20, Part A, or that of Example 21, Part A, affords the corresponding compounds of the formula below in like manner.

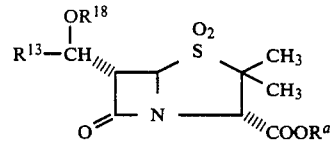

where R$^a$ and R$^{13}$ are as defined in Examples 15 and 18 and R$^{18}$ is acetyl, propionyl, n-butyryl, isobutyryl, n-valeroyl, isovaleroyl, trifluoroacetyl, methoxycarbonyl, ethoxycarbonyl, t-butoxycarbonyl, 2-pyrazinecarbonyl, benzoyl, aminocarbonyl, N-methylaminocarbonyl, N,N-dimethylaminocarbonyl, N-phenylaminocarbonyl, N-benzylaminocarbonyl, N-methyl-N-phenylaminocarbonyl, N-isobutylaminocarbonyl, N-n-butylaminocarbonyl or N,N-dipropylaminocarbonyl.

Removal of the carboxy protecting group, R$^a$, e.g. by the methods of Examples 23, 25, Part C, 26, 36 or 38 provides the corresponding sodium salt, potassium salt or free acid.

Alternatively, the esters of the formula above are treated with DBN and then the carboxy protecting group, R$^a$, is removed, e.g. by the procedures of Examples 45, Parts A and B, to afford compounds of the formula

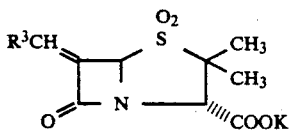

where $R^3$ is $R^{13}$ as defined above.

EXAMPLE 47

By repeating the procedure of Examples 15 and 18 with the appropriate aldehyde $R^{13}CHO$ and acylation of the resulting 6-($R^{13}$-substituted)hydroxymethyl-penicillanate ester by the method of Example 44 or 46, likewise provides the compounds of the formula below wherein $R^1$ is as defined in Example 33 and $R^{13}$ is $R^3$ as defined therein, except that $R^{13}$ is other than an alkylthio, phenylthio or phenylsulfonyl group;

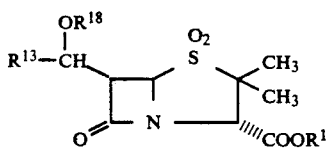

and $R^{18}$ is as defined in Examples 44 or 46. Hydrolysis or hydrogenolysis by the methods described above provided the corresponding carboxylic acid or salt where $R^1$ is H, Na or K.

EXAMPLE 48

Iodomethyl 6-(2-pyridyl)methylene-1,1-dioxopenicillanate

To 50 ml chloroform is added 6.44 g (0.02 mole) 6-(2-pyridyl)methylenepenicillanic acid 1,1-dioxide, 10 ml water and the pH is adjusted to 8.5 with tetrabutylammonium hydroxide. The organic layer is separated and the aqueous phase is extracted with fresh chloroform and the combined organic layers are concentrated in vacuo to yield tetrabutylammonium 6-(2-pyridyl)methylene-1,1-dioxopenicillanate. This is combined with 30 ml chloroiodomethane and the mixture is stirred for 16 hours. The mixture is concentrated to dryness in vacuo and the residue purified by column chromatography on silica gel to obtain chloromethyl 6-(2-pyridyl)methylene-1,1-dioxopenicillanate.

The chloromethyl ester is taken up in acetone, 50 ml, 6 g sodium iodide is added and the mixture is stirred overnight at room temperature. The precipitate sodium chloride is removed by filtration, the filtrate evaporated in vacuo and the residue is treated with 1:1 ethyl acetate/ethyl ether. The precipitated salt (NaI) is filtered off and the filtrate evaporated at reduced pressure to obtain the title compound.

EXAMPLE 49

Tetrabutylammcnium 6-[D-(2-[1-methyl-2-methoxycarbonylvinylamino]-2-phenylacetamido)]penicillanate To 300 ml chloroform was added 39.3 g 6-[D-(2-amino-2-phenylacetamido)]penicillanic acid trihydrate, 50 ml of water was added and the pH of the mixture adjusted to 8.5 by addition of 40% aqueous tetrabutylammonium hydroxide. The layers were separated, the aqueous layer was saturated with sodium sulfate and extracted with fresh chloroform. The extracts and initial lower layer were combined and the solvent was evaporated to about 250 ml total volume.

To this was added 150 ml methyl acetoacetate and 30 g of anhydrous magnesium sulfate. The mixture was heated at reflux for three hours, the mixture allowed to settle and the warm organic layer decanted. The clear chloroform solution was allowed to cool to obtain crystals of the title compound in 52% yield, m.p. 182°–184° C. (decomp.). $^1H$-NMR(CDCl$_3$)ppm(delta): 0.8–2.0 (m, 4H), 1.88 (s, 3H), 3.1–3.6 (m, 8H), 3.6 (s, 3H), 4.17 (s, 1H), 4.58 (s, 1H), 5.05 (d, 1H), 5.38–5.6 (m, 2H), 6.78 (d, 1H), 7.35 (s, 5H), 9.4 (d, 1H).

EXAMPLE 50

Tetrabutylammonium 6-[D-(2-[1-methyl-2-methoxycarbonylvinylamino]-2-4-hydroxyphenyl]acetamido)penicillanate To 300 ml of dichloromethane is added 41.9 g of 6-(2-amino-2-[4-hydroxyphenyl]acetamido)penicillanic acid trihydrate and 50 ml of water, and then the pH is adjusted to 8.5 using 40% aqueous tetrabutylammonium hydroxide. Three layers are obtained. The upper layer is removed, saturated with sodium sulfate and then it is extracted with dichloromethane. The extracts are combined with the middle layer and the lower layer, and the resulting mixture is evaporated in vacuo to give an oil which crystallized on trituration with acetone. This affords 44.6 g of tetrabutylammonium 6-(2-amino-2-[4-hydroxyphenyl]acetamido)penicillanate.

The above salt is added to 150 ml of methyl acetoacetate and the suspension is heated at ca. 65° C. until a clear solution is obtained (8 minutes). The mixture is allowed to cool, and then the solid is recovered by filtration. The solid is washed with methyl acetoacetate, followed by diethyl ether, to give 49.25 g of tetrabutylammonium 6-(2-[1-methyl-2-methoxycarbonylvinylamino]2-[4-hydroxyphenyl]acetamido)penicillanate crystals.

EXAMPLE 51

6-[D-(2-Amino-2-phenylacetamido)penicillanoyloxymethyl 6-(2-pyridyl)methylene-1,1-dioxopenicillanate hydrochloride A. 6-[D-(2-[1-methyl-2-methoxycarbonylvinylamino]-phenylacetamino)]penicillanoyloxymethyl 6-(2-pyridyl)methylene-1,1-dioxopenicillanate A solution of 744 mg (1.61 mmole) iodomethyl 6-(2-pyridyl)methylene-1,1-dioxopenicillanate and 1.11 g (1.61 mmole) tetrabutylammonium 6-[D-(2-[1-methyl-2-methoxycarbonylvinylamino]-2-phenylacetamido)]-penicillanate in 50 ml dimethylformamide is stirred overnight at room temperature. The mixture is diluted with ethyl acetate, washed with water, brine and dried (Na$_2$SO$_4$). The solvent is evaporated in vacuo. To the residue is added fresh ethyl acetate, the mixture washed again with water, brine, dried and the solvent evaporated. The residue is purified by column chromatography on silica gel.

B. To a solution of 530 mg (0.678 mmole) of the purified product of Part A in 25 ml acetone is added 6.8 ml 0.1N hydrochloric acid. After stirring for 10 minutes an additional 1.0 ml 0.1N hydrochloric acid is added and the acetone is evaporated in vacuo. The residue is taken up in water and freeze dried to provide the title compound.

Alternatively, the residue is purified by silica gel chromatography.

C. By employing tetrabutylammonium 6-[D-(2-[1-methyl-2-methoxycarbonylvinylamino]-2-[4-hydroxyphenyl]acetamido]penicillanate in the procedure of Part A, above, and removal of the amino protecting group by the procedure of Part B, provides 6-[D-(2-amino-2-[4-hydroxyphenyl]acetamido)]penicillanoyloxymethyl 6-(2-pyridyl)-methylene-1,1-dioxopenicillanate hydrochloride.

Similarly, use of the appropriate 6-$R^3$-methylene-1,1-dioxopenicillanic acid in the procedure of Example 48 provides the corresponding iodomethyl ester which is reacted with tetrabutylammonium ampicillin enamine or tetrabutylammonium amoxicillin enamine by the procedure of Example 51 to provide compounds of the formula below in the form of the free base or hydrochloride acid addition salt.

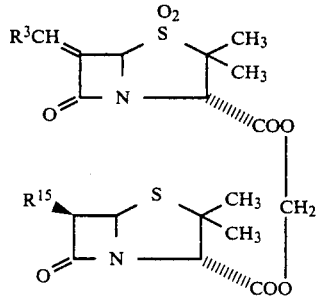

where $R^3$ is as defined in Example 33 and $R^{15}$ is D-2-amino-2-phenylacetamido or D-2-amino-2-(4-hydroxyphenyl)-acetamido.

EXAMPLE 52

By employing the appropriate iodomethyl ester of the formula

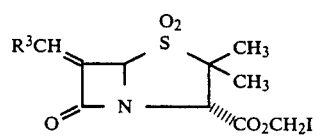

prepared by the method of Example 48, and the appropriate penicillin salt of the formula

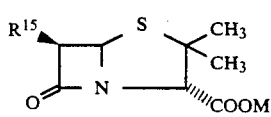

where M is Na, K or tetrabutylammonium, in the procedure of Example 51, Part A, provides coupled compounds of the formula below

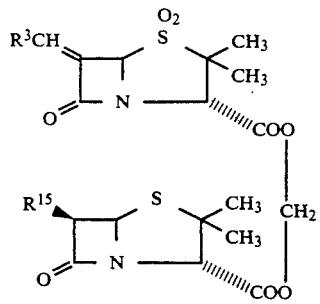

where $R^3$ is as defined in the Examples above and $R^{15}$ is
2-phenylacetamido,
2-phenoxyacetamido,
2-carboxy-2-phenylacetamido,
2-carboxy-2-(2-thienyl)acetamido,
2-carboxy-2-(3-thienyl)acetamido,
D-2-(4-ethyl-2,3-dioxopiperazinocarbonylamino)-2-phenylacetamido, or
2,2-dimethyl-4-phenyl-5-imidazolidinone-1-yl.

EXAMPLE 53

Similarly, the compounds of the formula below are provided by the procedures of Examples 48-52 from the appropriate starting materials.

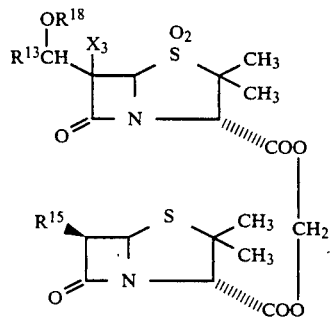

where $X_3$, $R^{15}$ and $R^{18}$ are as defined in Examples above and below, and $R^{13}$ is as defined in Example 47.

EXAMPLE 54

A. Potassium (6-alpha, 8S)-6-pyrimidin-2-yl)hydroxymethyl-1,1-dioxopenicillanate To a solution of 300 mg (0.79 mmole) of the first eluted isomer of allyl 6-alpha-(pyrimidin-2-yl)hydroxymethyl-1,1-dioxopenicillanate (obtained in Example 18) in 4 ml ethyl acetate was added 30 mg tetrakis (triphenylphosphine)palladium (O) and 30 mg triphenylphosphine. The mixture was stirred under nitrogen to solvate the reagents (5-10 minutes) and 1 57 ml (0.79 mmole) potassium 2-ethylhexanoate in ethyl acetate was added. After stirring at room temperature for 20 minutes, the mixture was filtered and the cake washed with ethyl acetate and dried to afford 53 mg of yellow solid. The filtrate was treated with ethyl ether to precipitate a second crop, 152 mg; total yield 69%. $^1$H-NMR, 250 MHz, (DMSO-$d_6$)ppm (delta): 1.33 (s, 3H), 1.44 (s, 3H), 3.77 (s, 1H), 3.95 (d or d, J=2, J=6, 1H), 4.89 (d, J=2, 1H), 5.1 (d, J=6, 1H), 6.33 (s, 1H), 7.48 (t, J=4, 1H), 8.84 (d, J=4, 2H).

B. Potassium (6-alpha, 8R)-6-(pyrimidin-2-yl)hydroxymethyl-1,1-dioxopenicillanate A solution of 300 mg (0.79 mmole) of the second eluted isomer of allyl 6-alpha-(pyrimidin-2-yl)hydroxymethyl-1,1-dioxopenicillanate (obtained in Example 18) was converted to its potassium salt by the above procedure to afford 236 mg (79%) $^1$H-NMR, 250 MHz, (DMSO-d$_6$)ppm (delta): 1.30 (s, 3H), 1.42 (s, 3H), 3.65 (s, 1H), 4.60 (dd, J=2, J=8, 1H), 4.75 (d, J=2, 1H), 5.15 (d, J=8, 1H), 7.47 (t, J=4, 1H), 8.85 (d, J=4, 2H).

EXAMPLE 55

A. Allyl (6-alpha, 8S)-6-(pyrimidin-2-yl)acetoxymethyl-1,1-dioxopenicillanate

To a solution of 785 mg (2.1 mmole) of the first eluted isomer of allyl 6-alpha-(pyrimidin-2-yl)hydroxymethyl-1,1-dioxopenicillanate (obtained in Example 18) in 4 ml methylene chloride was added 0.45 ml (5.6 mmole) pyridine and 0.53 ml (5.6 mmole) acetic anhydride and the mixture was stirred at room temperature for 2.5 hours. The mixture was diluted with 30 ml methylene chloride, extracted with water (7×60 ml), dried over anhydrous magnesium sulfate and filtered. Evaporation in vacuo gave 813 mg (92%) of the title compound. $^1$H-NMR(CDCl$_3$)ppm (delta): 1.4 (s, 3H), 1.6 (s, 3H), 2.2 (s, 3H), 4.45 (s, 3H), 4.45 (dd, 1H), 4.75 (m, 2H), 4.95 (d, 1H), 5.2–5.6 (m, 2H), 5.7–6.3 (m, 1H), 6.45 (d, 1H), 7.35 (t, 1H), 8.85 (d, 1H).

B. Allyl (6-alpha, 8R)-6-pyrimidin-2-yl)acetoxymethyl-1,1-dioxopenicillanate

Acetylation of the second, eluted isomer of allyl 6-alpha-(pyrimidin-2-yl)hydroxymethyl-1,1-dioxopenicillanate (obtained in Example 18) by the above method gave an 88% yield of the title compound. $^1$H-NMR(CDCl$_3$) ppm (delta): 1.4 (s, 3H), 1.6 (s, 3H), 4.45 (s, 1H), 4.50 (dd, J=1, J=8, 1H), 4.75 (m, 2H,) 4.8 (d, J=1, 1H), 5.25–5.6 (m, 2H), 5.7–6.3 (m, 1H), 6.4 (d, J=8, 1H), 7.35 (t, J=6, 1H), 8.8 (d, J=6, 1H).

EXAMPLE 56

A. Potassium (6-alpha, 8S)-6-(pyrimidin-2-yl)acetoxymethyl-1,1-dioxopenicillanate A solution of 789 mg (1.86 mmole) allyl (6-alpha, 8S)-6-(pyrimidin-2-yl)acetoxymethyl-1,1-dioxopenicillanate in 4 ml ethyl acetate was reacted by the procedure of Example 54 to give 342 mg (43%) of the desired potassium salt which was purified by preparative MPLC* eluting with 9:1 water/acetonitrile to give 105 mg of product (85% pure by HPLC analysis).
*MPLC is medium pressure liquid chromatography. HPLC is high pressure liquid chromatography.

B. Potassium (6-alpha, 8R)-6-(pyrimidin-2-yl)acetoxy-methyl-1,1-dioxopenicillanate A solution of 666 mg (1.57 mmole) allyl (6-alpha, 8R)-6-(pyrimidin-2-yl)acetoxymethyl-1,1-dioxopenicillanate was reacted by the same procedure to give 339 mg (51%) of crude product which was purified by preparative MPLC* with 9:1 water/acetonitrile to yield 162 mg of pure isomer: $^1$H-NMR, 250 MHz, (DMSO-d$_6$)ppm (delta): 1.34 (s, 3H), 1.44 (s, 3H), 2.17 (s, 3H), 3.65 (s, 1H), 4.15 (dd, J=2, J=8, 1H), 4.97 (d, J=2, 1H), 6.27 (d, J=8, 1H), 7.50 (t, J=5, 1H), 8.85 (d, J=5, 2H).
*MPLC is medium pressure liquid chromatography. HPLC is high pressure liquid chromatography.

EXAMPLE 57

Employing the appropriate starting 6-R$^{13}$-CHOH-substituted-1,1-dioxopenicillanate ester provided in Example 18, the following acetate esters are prepared by the method of Examples 20 or 55.

| R$^{13}$ | C$_6$, C$_8$ Stereo-chemistry | % Yield | $^1$H-NMR(CDCl$_3$)ppm(delta): |
|---|---|---|---|
| C$_6$H$_5$N-pyrazolyl | 6-alpha, 8S and 6-alpha, 8R mixture | 100 | 1.43,(s,3H),1.63(s,3H),2.25(s,3H),4.51(m,2H),4.79(m, 2H),5.43(m,2H),5.98(m,1H),6.65(d,1H),7.5(m,3H),7.98(s, 1H),8.20(m,2H). |
| pyrazinyl | 60:40 mixture of 6-alpha, 8S 6-alpha, 8R | 69 | 1.4(s,1.8H),1.43(s,1.2H),1.56(s,1.2H),1.62(s,1.8H),2.2(s, 1.2H),2.3(s,1.8H),4.35(m,1H),4.4(s,0.6H),4.43(s,0.4H), 4.78(d,0.6H),4.8(d,0.4H),5.3–5.5(m,2H),5.8–6.05(m, 1H),6.3(m,1H),7.45(d,1H),8.82(d,1H),9.25(m,1H). |
| pyrimidinyl | 60:40 mixture of 6-alpha, 8S 6-alpha, 8R | 66 | 1.4(s,1.8H),1.5(s,1.2H),1.6(s,1.8H),1.65(s,1.2H),2.2(s, 1.2H),2.26(s,1.8H),4.23(dd,0.4H),4.35(dd,0.6H),4.4(s, 0.6E,4.45(s,0.4H),4.68(m,2H),4.74(d,0.6H),5.0(d,0.4H), 5.35(m,2H),5.9(m,1H),6.45(m,1H),8.6(m,2H),8.75(m, 1H). |
| CH$_3$O-benzothiazolyl | | 92 | Dark green viscous liquid |

EXAMPLE 58

The 8-acetoxy-3-carbonyloxyallyl esters provided in Example 25A and 57 are converted to the potassium salt of the formula below by the method of Example 54,

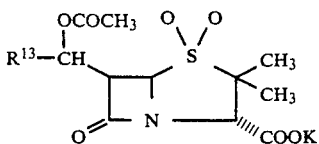

| $R^{13}$ | $C_6, C_8$ Stereo-chemistry | % Yield | $^1$H-NMR(D$_2$O)ppm(delta): |
|---|---|---|---|
| pyrimidine-like ring (N=CH-CH=C-CH= with N) | 65:35 6-alpha, 8S 6-alpha, 8R | 57, (crude) 21, (purified by chromatography*, mixed isomers) | Purified: 1.45(s,3H),1.58(s,3H),1.25(s,1.05H),1.32(s,1.95H), 4.25(s,0.65H),4.28(s,0.35H),4.37(dd,0.65H),4.45(dd,0.35H), 5.15(d,0.65H),5.2(d,0.35H),6.25(d,0.65H),6.35(d,0.35H),7.73 (m,1H),8.85(m,1H),9.15(m,1H). |
| N-methylimidazole ring | 6:1 6-alpha, 8S 6-alpha, 8R | 64 | 1.44(s,3H),1.5(s,3H),1.62(s,3H),2.2(s,0.4H),2.24(s,2.6H),3.8 (s,3H),4.27(s,1H),4.4(dd,1H),4.96(d,1H),6.45(d,0.15H),6.5 (d,0.85H),7.07(s,0.15H),7.1(d,0.85H),7.16(s,0.15H),7.2(d, 0.85H). IR(KBr): 3409,1786,1740,1620 cm$^{-1}$. |
| pyrazine ring | 30:70 6-alpha, 8S 6-alpha, 8R | 84, crude 43, after chromatography | 1.3(s,2.1H),1.34(s,0.9H),1.42(s,3H),2.13(s,0.9H),2.2(s,2.1H), 3.66(s,0.7H),3.7(s,0.3H),4.1(dd,0.3H),4.95(d,0.7H),5.07(d, 0.3H),6.24(d,0.3H),6.36(d,0.7H),8.7(s,2H),8.8(s,0.7H),8.83 (s,0.3H). IR(KBr): 3468,1781,1746,1623 cm$^{-1}$. |

*Used C$_{18}$, (C$_{18}$ is monooctadecylsilicate)column.

EXAMPLE 59

The 8-acetoxy esters provided above and below are converted to the corresponding 6-methylene compounds by the method of Example 20, Part B and the allyl group removed by the method of Example 54 to provide the potassium salt of the formula below where R$^1$ is potassium.

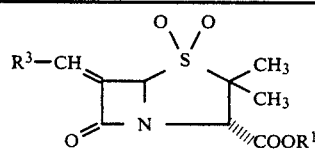

| | R$^1$ = allyl | | R$^1$ = potassium | |
|---|---|---|---|---|
| R$^3$ | % Yield | $^1$H-NMR(CDCl$_3$)ppm(delta): | % Yield | $^1$H-NMR(D$_2$O or d$_6$-acetone)ppm(delta): |
| C$_6$H$_5$N-N=C(CH$_3$)- (phenyl pyrazole) | 100, yellow powder | 1.50 (s, 1.5H), 1.54 (s, 1.5H), 1.65 (s, 3H), 4.58 (s, 1H), 4.80 (d, 2H), 5.30 (s, 1H), 5.50 (m, 2H), 6.00 (m, 1H), 7.10 (s, 1H), 7.5 (m, 3H), 8.02 (s, 0.5H), 8.25 (m, 2H), 8.87 (s, 0.5H). A 1:1 mixture of E and Z isomers. | 42, E isomer only | 1.53 (s, 3H), 1.63 (s, 3H), 4.3 (s, 1H), 5.7 (s, 1H), 7.2 (s, 1H), 7.4–8.0 (m, 5H), 8.7 (s, 1H). |
| pyrimidinyl | | | isolated as byproduct from corresponding compound in Example 58 | 1.55 (s, 3H), 1.65 (s, 3H), 4.35 (s, 1H), 5.12 (d, 1H), 7.52 (d, 1H), 7.68 (d, 1H), 8.85 (m, 1H), 9.2 (m, 1H). |
| thiadiazolyl-C(CH$_3$)= (Starting compound, Example 68B) | 46 | 1.48 (s, 3H), 1.62 (s, 3H), 4.52 (s, 1H), 4.60–4.80 (s, 2H), 5.31–5.44 (m, 2H), 5.74 (s, 1H), 5.87–6.01 (m, 1H), 7.59 (s, 1H), 8.76 (s, 1H). | 39 yellow solid | 1.38 (s, 3H), 1.40 (s, 3H), 4.19 (s, 1H), 5.92 (s, 1H), 7.76 (s, 1H), 9.13 (s, 1H). Infrared (KBr): 1775, 1620 cm$^{-1}$. |

-continued

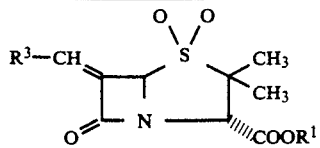

| R³ | R¹ = allyl | | R¹ = potassium | |
|---|---|---|---|---|
| | % Yield | ¹H-NMR(CDCl₃)ppm(delta): | % Yield | ¹H-NMR(D₂O or d₆-acetone)ppm(delta): |
| isoxazole (S-N ring) (Starting compound, Example 68B) | 59 | 2.46 (s, 3H), 2.60 (s, 3H), 4.46 (s, 1H), 5.20–5.42 (m, 2H), 5.66 (s, 1H), 5.80–6.02 (m, 1H), 7.38–7.42 (m, 2H), 8.71 (m, 1H). Infrared: 1795 cm⁻¹. | 50, 3.5:1 ratio of MP:LP isomers | 1.40 (s, 3H), 1.48 (s, 3H), 4.20 (s, 1H), 5.91 (s, 1H), 7.40–7.60 (m, 2H), 8.89 (m, 1H). Infrared (KBr): 1760, 1610 cm⁻¹. |
| 4-methyl-2-methylthiazole (CH₃-S-N with CH₃) | 95 | 1.52 (s, 3H), 1.64 (s, 3H), 2.46 (s, 3H), 4.5 (s, 1H), 4.66–4.82 (m, 2H), 5.34–5.46 (m, 2H), 5.65 (s, 1H), 6.0 (m, 1H), 7.16 (s, 1H), 7.34 (s, 1H). Infrared: 1790, 1760, 1680 cm⁻¹. | 84 | 1.38 (s, 3H), 1.46 (s, 3H), 2.33 (s, 3H), 4.16 (s, 1H), 5.89 (s, 1H), 7.3 (s, 1H), 7.46 (s, 1H). Infrared (KBr): 1773, 1683, 1619 cm⁻¹. |
| pyridazine (N-N ring) Starting with 8-hydroxy compound of Example 18 | 8 | 1.49 (s, 3H), 1.63 (s, 3H), 4.52 (s, 1H), 4.60–4.78 (m, 2H), 5.20–5.45 (m, 2H), 5.96–6.02 (m, 2H), 7.39 (s, 1H), 7.48–7.58 (m, 2H), 9.12–9.21 (m, 1H). | 20 | Infrared: 1780, 1625 cm⁻¹. |
| 3-methyl-5-methyl-1,2,4-oxadiazole (CH₃-O-N=C-N with CH₃) | 64, oil | 1.46 (s, 3H), 1.60 (s, 3H), 3.64 (s, 3H), 4.51 (s, 1H), 4.60–4.80 (m, 2H), 5.24–5.46 (m, 2H), 5.62 (s, 1H), 5.80–6.02 (m, 1H), 7.32 (s, 1H). IR(KBr) cm⁻¹: 1805. | 58 | 1.42 (s, 3H), 1.48 (s, 3H), 2.52 (s, 3H), 4.25 (s, 1H), 5.87 (s, 1H), 7.18 (s, 1H). IR(KBr) cm⁻¹: 1785. |
| 6-methoxybenzothiazole (CH₃O-benzothiazole) | 21 | 1.5 (s, 3H), 1.62 (s, 3H), 3.85 (s, 3H), 4.5 (s, 1H), 4.72 (m, 2H), 5.3–5.5 (m, 2H), 5.7 (s, 1H), 5.9–6.05 (m, 2H), 7.0–7.2 (m, 1H), 7.3 (m, 1H), 8.05 (d, 1H). | 68 two crops gold colored solid | 1.54 (s, 3H), 1.62 (s, 3H), 3.76 (s, 3H), 4.34 (s, 1H), 5.52 (s, 1H), 7.02 (d, 1H), 7.2 (s, 1H), 7.44 (s, 1H), 7.72 (d, 1H). |

EXAMPLE 60

Potassium 6-(Imidazol-2-yl)hydroxymethyl-1,1-dioxopenicillanate

A mixture of 141 mg (0.38 mmole) allyl 6-(imidazol-2-yl)hydroxymethyl-1,1-dioxopenicillanate [mixed isomers obtained in Example 18], 12 mg tetrakis (triphenylphosphine)palladium (O), 12 mg triphenylphosphine, 0.76 ml (0.38 mmole) potassium 2-ethylhexanoate and 2 ml ethyl acetate was stirred under nitrogen for one hour. The precipitated product was recovered by filtration to give 143 mg (100%) of yellow solid which was found to contain two isomers by high pressure liquid chromatography analysis. Infrared (KBr): 3382, 1780, 1728 and 1615 cm⁻¹.

EXAMPLE 61

A. Benzyl 6-(2-thiazolyl)hydroxymethyl-1,1-dioxopenicillanate

A solution of 17.79 g (44 mmole) benzyl 6-alpha-bromo-1,1-dioxopenicillanate in 250 ml dry tetrahydrofuran was reacted with an equimolar amount of methylmagnesium bromide at −78° C., then after stirring for one minute, an equimolar amount of thiazol-2-carboxaldehyde added and stirring continued for 10 minutes. An equimolar amount of acetic acid was then added, and after stirring five minutes, the mixture was poured into 500 ml water. Extraction with ethyl acetate, washing of the extracts with water, drying (MgSO₄), and evaporation of solvent in vacuo gave 16.93 g (89%) of crude product which showed two spots on TLC. The crude product was purified by silica gel column chromatography, eluting with chloroform/ethyl acetate, 96:4, to afford 4.72 g of a more polar isomer, 2.98 g of a less polar isomer and 0.5 g of mixed isomers; (total yield 43%).

More polar isomer: $^1$H-NMR(CDCl$_3$)ppm (delta): 1.25 (s, 3H), 1.55 (s, 3H), 4.3 (dd, 1H), 4.45 (s, 1H), 4.65 (bs, 1H), 4.9 (d, 1H), 5.2 (m, 2H), 5.55 (d, 1H), 7.35 (m, 6H), 7.75 (d, 1H).

Less polar isomer: $^1$H-NMR(CDCl$_3$)ppm (delta): 1.2 (s, 3H), 1.5 (s, 3H), 4.35 (m, 2H), 4.75 (d, 1H), 5.1 (m, 2H), 5.55 (d, 1H), 7.2 (m, 6H), 7.6 (d, 1H).

B. Diphenylmethyl 6-(2-thiazolyl)hydroxymethyl-1,1-dioxopenicillanate

Repeating the above procedure with diphenylmethyl 6-alpha-bromo-1,1-dioxopenicillanate on a 20 millimolar scale and purification by silica gel chromatography eluting with 9:1chloroform/ethyl acetate gave 2.464 g of a less polar (LP) isomer and 3.029 g of a more polar (MP) isomer.

More polar isomer: $^1$H-NMR(CDCl$_3$)ppm (delta): 1.06 (s, 3H), 1.52 (s, 3H), 4.1–4.3 (m, 1H), 4.42 (s, 1H), 4.76 (d, 1H), 5.45 (d, 1H), 6.82 (s, 1H), 7.05–7.3 (m, 11H), 7.56 (d, 1H).

Less polar isomer: $^1$H-NMR(CDCl$_3$)ppm (delta): 1.2 (s, 3H), 1.65 (s, 3H), 4.35 (dd, 1H), 4.55 (s, 1H), 4.83 (d, 1H), 5.65 (dd, 1H), 6.95 (s, 1H), 7.2–7.4 (m, 11H), 7.75 (d, 1H).

EXAMPLE 62

Employing the appropriate acid chloride of formula R$^{18}$Cl, or the corresponding acid anhydride, and the appropriate 6-R$^{13}$CHOH-substituted-1,1-dioxopenicillanate ester, provided above, the following compounds were prepared by the method of Example 20, Part A.

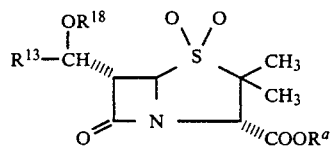

| R$^a$ | R$^{13}$ | R$^{18}$ | Stereochemistry at C$_8$ | $^1$H-NMR(CDCl$_3$)ppm(delta): |
|---|---|---|---|---|
| C$_6$H$_5$CH$_2$ (from more polar 8-hydroxy compound of Example 61A) | 2-thiazolyl | C$_2$H$_5$C(=O)– | (R) | 1.3 (t, 3H), 1.4 (s, 1H), 1.65 (s, 1H), 2.55 (q, 2H), 4.5 (s, 1H), 4.4–4.6 (m, 1H), 4.85 (d, 1H), 5.27 (s, 2H), 6.65 (d, 1H), 7.35 (m, 6H), 7.75 (d, 1H). |
| (C$_6$H$_5$)$_2$CH (from less polar isomer of Example 61B) | 2-thiazolyl | C$_2$H$_5$OC(=O)– | (S) | 1.25 (s, 3H), 1.3 (t, 3H), 1.75 (s, 3H), 4.24 (q, 2H), 4.36–4.60 (m, 1H) 4.55 (s, 1H), 5.02 (d, 1H), 6.43 (d, 1H), 6.95 (s, 1H), 7.1–7.5 (m, 11H), 7.75 (d, 1H). |
| (C$_6$H$_5$)$_2$CH (from more polar isomer of Example 61B) | 2-thiazolyl | C$_2$H$_5$OC(=O)– | (R) | Pink, solid foam |
| allyl | 2-thiazolyl | pyrazinyl-CO– | (S) + (R) | 1.4 (s, 2.1H), 1.5 (s, 0.9H), 1.6 (s, 2.1H), 1.65 (s, 0.9H), 4.4 (s, 0.7H), 4.5 (0.3H), 4.5–5.0 (m, 4H), 5.1–6.2 (m, 3H), 6.9 (d, 1H), 7.4 (m, 1H), 7.8 (d, 1H). |
| allyl | 2-thiazolyl | (CH$_3$)$_2$CHC(=O)– | (S) less polar 22% yield | 1.37 (m, 3H), 1.50 (m, 3H), 1.65 (s, 3H), 1.82 (s, 3H), 2.70 (m, 1H), 4.61 (s, 1H), 4.7 (m, 1H), 4.9 (m, 2H), 5.12 (d, 1H), 5.41 (m, 1H), 5.6 (m, 1H), 5.8–6.5 (m, 1H), 6.75 (d, 1H), 7.6 (d, 1H), 7.97 (d, 1H). |
|  |  |  | (R) more polar 41% yield | 1.18 (m, 3H), 1.28 (m, 3H), 1.33 (s, 3H), 1.52 (s, 1H), 2.6 (m, 1H), 4.3–4.7 (m, 5H), 5.0–5.4 (m, 2H), 5.45–6.2 (m, 1H), 6.47 (d, 1H), 7.23 (d, 1H), 7.63 (d, 1H). |
| C$_6$H$_5$CH$_2$ | 2-thiazolyl | C$_6$H$_5$C(=O)– | (S) less polar | 1.4 (s, 3H), 1.6 (s, 3H), 4.5 (s, 1H) 4.4–4.6 (m, 1H), 5.1 (d, 1H), 5.2 (s, 2H), 6.7 (d, 1H), 7.2–8.2 (m, 12H). |
|  |  |  | (R) more polar | 1.3 (s, 3H), 1.6 (s, 3H), 4.5 (s, 1H), 4.6 (dd, 1H), 4.86 (d, 1H), 5.2 (s, 2H), 6.85 (d, 1H), 7.3–7.7 (m, 9H), |

-continued

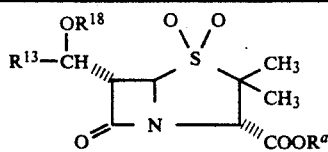

| $R^a$ | $R^{13}$ | $R^{18}$ | Stereo- chemistry at $C_8$ | $^1$H-NMR(CDCl$_3$)ppm(delta): |
|---|---|---|---|---|
| | | | | 7.8 (d, 1H), 8.15 (dd, 2H). |

EXAMPLE 63

A. (6-alpha, 8R)-6-(Thiazol-2-yl)propionyloxymethyl-1,1-dioxopenicillanic Acid

A mixture of 1.89 g of 10% palladium-on-carbon catalyst in 20 ml of a 9:7 (v/v) mixture of tetrahydrofuran (THF) and water was saturated with hydrogen and a solution of 689 mg (1.4 mmole) benzyl (6-alpha, 8R)-6-(thiazol-2-yl)propionyloxymethyl-1,1-dioxopenicillanate in 13 ml THF and 7 ml water was added. The resulting mixture was hydrogenated at 3 bars pressure for 20 minutes, the catalyst was then removed by filtration, the filtrate extracted with ethyl acetate (3×200 ml) and the extracts dried (MgSO$_4$). Evaporation of solvent in vacuo gave 330 mg yellow solid.

B. (6-alpha, 8R)-6-(Thiazol-2-yl)benzoyloxymethyl1,1-dioxopenicillanic Acid

The title compound was obtained by the above procedure from the corresponding benzyl ester in 57% yield. $^1$H-NMR(D$_2$O)ppm (delta): 1.38 (s, 3H), 1.55 (s, 3H), 4.25 (s, 1H), 4.44 (dd, 1H), 5.05 (d, 1H), 6.68 (d, 1H), 7.4 (t, 7H), 7.55 (t, 1H), 7.58 (d, 1H), 7.7 (d, 1H), 7.95 (d, 1H). Infrared (KBr): 3473, 1782, 1729, 1622 cm$^{-1}$.

EXAMPLE 64

A. (6-alpha, 8S)-6-(Thiazol-2-yl)ethoxycarbonyloxymethyl-1,1-dioxopenicillanic Acid To a solution of 557 mg (0.954 mmole) diphenylmethyl (6-alpha, 8S)-6-(thiazol-2-yl)ethoxycarbonyloxymethyl-1,1-dioxopenicillanate in 5 ml methylene chloride was added 0.62 ml (5.72 mmole) anisole. The mixture was cooled to −5° and a mixture of 382 mg (2.86 mmole) anhydrous aluminum chloride and 2 ml nitromethane was added slowly over 15 minutes. The reaction mixture was diluted with 50 ml ethyl acetate, water added and the pH adjusted to pH 7.5. The aqueous layer was separated, acidified to pH 3 and extracted with ethyl acetate. Evaporation of solvent gave a residual glass which was dissolved in ethyl ether, filtered and hexane added to the filtrate to effect precipitation. After filtering to recover solid and drying, 211 mg (53%) of product was obtained. $^1$H-NMR, 300 MHz, (CDCl$_3$)ppm (delta): 1.40 (t, 3H), 1.53 (s, 3H), 1.67 (s, 3H), 4.28–4.42 (m, 3H), 4.50 (s, 1H), 4.92 (s, 1H), 6.58 (d, 1H), 7.53 (d, 1H), 7.93 (d, 1H). Infrared (KBr): 3443, 1797, 1754 cm$^{-1}$.

B. Employing the (6-alpha, 8R)-isomer of the starting diphenylmethyl ester provided in Example 62 in the above procedure affords the corresponding (6-alpha, 8R)-isomer of 6-(thiazol-2-yl)ethoxycarbonyloxymethyl-1,1-dioxopenicillanic acid. $^1$H-NMR, 300 MHz, (CDCl$_3$)ppm (delta): 1.34 (t, 3H), 1.53 (s, 3H), 1.65 (s, 3H), 4.2–4.4 (m, 3H), 4.44 (s, 1H), 5.04 (s, 1H), 6.67 (d, 1H), 7.53 (d, 1H), 7.90 (d, 1H). Infrared (KBr) 3418, 1803, 1750 cm$^{-1}$.

EXAMPLE 65

Employing the appropriate allyl ester provide in Example 62 as starting material, the following potassium salts are obtained by the method of Example 60.

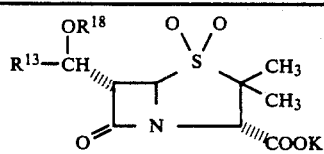

| $R^{13}$ | $R^{18}$ | Stereo- chemistry at $C_8$ | NMR data |
|---|---|---|---|
| 2-thiazolyl | (pyrimidinyl-C(=O)–) | (S) + (R) | $^1$H-NMR(D$_2$O)ppm(delta) <br> 1.46 (s, 3H), 1.65 (s, 3H), 4.35 (2s, 1H), 5.2 (d, 1H), 7.05 (d, 1H), 7.7–8.0 (m, 2H), 8.7–9.5 (m, 3H). |
| 2-thiazolyl | (CH$_3$)$_2$CHC(=O)– | (S) <br> 90% yield | $^1$H-NMR(DMSO-d$_6$)ppm(delta). <br> 1.13 (d, 3H), 1.16 (d, 3H), 1.33 (s, 3H), 1.45 (s, 3H), 2.65 (m, 1H), 3.73 (s, 1H), 4.23 (dd, 1H), 4.93 (d, 1H), 6.50 (d, 1H), 7.85 (m, 2H). <br> Infrared (KBr): 3777, 3472, 3447, 3402, 3270, 1783, 1746 1621 cm$^{-1}$/ |
| | | (R) <br> 27% yield | 1.17 (d, 3H), 1.20 (d, 3H), 1.44 (s, 3H), 2.69 (m, 1H), 3.68 (s, 1H), 4.12 (dd, 1H), 4.93 (d, 1H), 6.59 (d, 1H), |

-continued

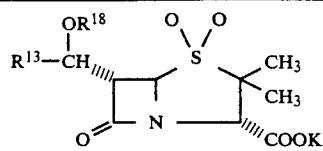

| R[13] | R[18] | Stereo-chemistry at C8 |
|---|---|---|

7.84 (m, 2H).
Infrared (KBr): 3543, 3498, 3437, 3415, 3348, 3270, 3119, 1917, 1783, 1745, 1718, 1619 cm$^{-1}$.

EXAMPLE 66

A. Allyl 6-bromo-6-(2-thiazolyl)hydroxymethyl-1,1-dioxopenicillanate

A solution of 8.84 g (20 mmole) allyl 6,6-dibromo-1,1-dioxopenicillanate in 100 ml dry tetrahydrofuran was cooled to −78° C., 7.02 ml (20 mmole) methylmagnesium bromide was added and the mixture stirred for 5 minutes. A solution of 2.26 g (20 mmole) thiazole-2-carboxaldehyde in 10 ml of the same solvent was added at −78° C. and the resulting mixture stirred for 20 minutes. Acetic acid (1.2 ml) was added, the mixture was poured into water and extracted with ethyl acetate and chloroform. The combined organic layers were dried (Na2SO4) and the solvent evaporated in vacuo to yield 8.5 g crude product as a glass. The crude glass was purified by column chromatography on silica gel, eluting with 89:11 chloroform/ethyl acetate to afford 6.2 g (72%) of pure product which was found to be a single isomer. $^1$H-NMR (CDCl3)ppm (delta): 1.4 (s, 3H), 1.6 (s, 3H), 4.0 (bs, 1H), 4.42 (s, 1H), 4.6 (d, 2H), 5.3 (s, 1H), 5.55 (s, 1H), 5.1–6.3 (m, 3H), 7.35 (d, 1H), 7.75 (d, 1H).

B. Benzyl 6-bromo-6-(2-thiazolyl)hydroxymethyl-1,1-dioxopenicillanate

Employing benzyl 6,6-dibromo-1,1-dioxopenicillanate in place of the allyl ester in the above procedure provided the title compound as an orange foam in quantitative yield. $^1$H-NMR(CDCl3)ppm (delta): 1.32 (s, 3H), 1.60 (s, 3H), 4.5 (s, 2H), 5.2–5.8 (m, 4H), 7.3 (d, 1H), 7.4 (s, 5H), 7.8 (d, 1H).

C. The following compounds were prepared in like manner by the procedure of Part A.

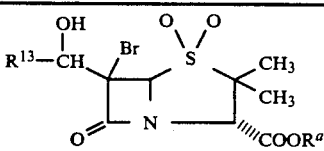

| R$^a$ | R[13] | % Yield | $^1$H-NMR(CDCl3)ppm (delta): |
|---|---|---|---|
| benzyl | 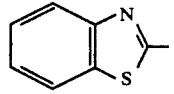 | 100 yellow foam | 1.25(s,3H),1.54(s,3H),4.5 (s,1H),5.02(s,2H),5.43(s, 1H),5.68(s,1H),7.32(m, 7H),8.00(m,2H). |
| benzyl | 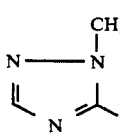 | 88 yellow solid | 1.4(2s,3H),1.6(s,3H),4.0 (s,1H),4.9(2,1H),5.18(m, 2H),5.5–5.8(m,2H),7.5(s, 5H),8.0 and 8.5(2s,1H). |

-continued

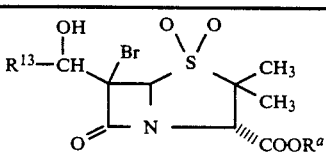

| R$^a$ | R[13] | % Yield | $^1$H-NMR(CDCl3)ppm (delta): |
|---|---|---|---|
| benzyl |  | 100 | 1.25(s,3H),1.52(s,3H),4.45 (s,0.75H),4.52(s,0.25H), 5.1–5.4(m,4H),7.3(s,5H), 8.6(m,2H),9.0(m,1H). |
| allyl |  | 38 | 1.38(s,3H),1.60(s,3H), 4.38–4.73(m,3H),5.0–6.0 (m,5H),7.10(s,1H),8.51(s, 1H). |

EXAMPLE 67

A. Acylation of the compounds provided in the previous Example by the method of Example 57 or 62 provided the following compounds in like manner.

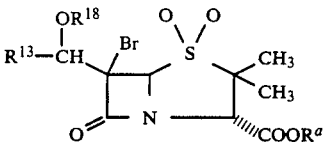

| R[13] | % Yield |  |
|---|---|---|

A. Where R$^a$ is allyl and R[18] is CH3CO:

|  |  | $^1$H-NMR(CDCl3)ppm(delta): |
|---|---|---|
| 2-thiazolyl | 49 colorless crystals | 1.4(s,3H),1.6(s,3H),2.25(s,3H), 4.45(s,1H),4.65(m,2H),5.4(s,1H), 5.2–6.3(m,3H),6.7(s,1H),7.4 (d,1H),7.8(d,1H). |
|  |  | $^{13}$C-NMR(CDCl3)ppm(delta): 18.4,19.8,20.4,60.7,63.1,64.4,66.5, 66.9,73.3,120.3,120.4,130.6,143.6, 163.7,165.5 166.2,168.6. |
|  | 59 (+21% of isomeric product) | 1.40(s,3H),1.60(s,3H),2.25(s, 3H),4.48–4.70(m,3H),5.2–6.2(m, 5H),6.92(s,1H),8.83(s,1H). |

B. Where R$^a$ is benzyl and R[18] is CH3CO:

|  |  | $^1$H-NMR(CDCl3)ppm(delta): |
|---|---|---|
| 2-thiazolyl | 100 glass 9:1 mixture of | 1.25(s,3H),1.55(s,3H),4.50(s, 0.9H),4.55(s,0.1H),5.2(m,2H), 5.40(s,0.9H),5.57(s,0.1H),6.42(s, 0.1H),6.60(s,0.9H),7.3(m,6H), |

-continued

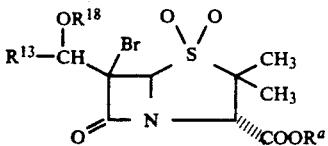

| R¹³ | % Yield | |
|---|---|---|
| | isomers | 7.75(d,1H). |
| 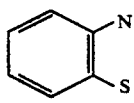 | 100 yellow-orange foam | 1.3(s,3H),1.52(s,3H),2.25(s,3H), 4.54(s,1H),5.02(s,2H),5.52(s, 1H),6.8(s,1H),7.3(m,7H),7.9(m, 2H). |
| 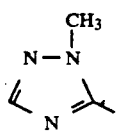 | 19 | 1.25(s,3H),1.5(s,3H),2.19(s,3H), 3.95(s,3H),4.4(s,1H),5.15(s,2H), 5.45(s,1H),6.3(s,1H),7.35(s,5H), 7.73(s,1H). |
| 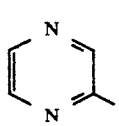 | 90 3:1 mixture of isomers | 1.25(s,2.25H),1.35(s,0.75H),1.4 (s,2.25H),1.42(s,0.75H),2.2(s, 2.25H),2.3(s,0.75H),4.45(s, 0.75H),4.55(s,0.25H),5.1–5.3(m, 2H),5.3(s,0.75H),5.6(s,0.25H), 6.25(s,0.25H),6.4(s,0.75H),7.3 (m,5H),8.67(m,2H),9.67(s,1H). |

C. Alternatively the compounds of the above formula are prepared upon carrying out the method of Example 66 with acylation of the reaction mixture prior to isolation of product by the following general method:

To a solution of 1.0 equivalent of 6,6-dibromopenicillanate ester in tetrahydrofuran at −78° C. was added 1.3 equivalents of methylmagnesium bromide dissolved in the same solvent and the mixture stirred for 5–10 minutes. The appropriate aldehyde (R¹³CHO), 1.3 equivalents in the same solvent was added at −78° C. to −68° C. and the reaction mixture stirred for 30 to 60 minutes. Then, 1.3 equivalents of acetyl chloride was added, stirring at −78° C. continued for 10 minutes and the product then isolated by pouring into ice/water, extracting with ethyl acetate, drying and evaporation of solvent in vacuo.

Where R¹⁸ is CH₃CO:

| Rᵃ | R¹³ | % Yield | ¹H-NMR(CDCl₃)ppm(delta): |
|---|---|---|---|
| benzyl | C₆H₅ | 100 | Pale yellow foam |
| allyl | 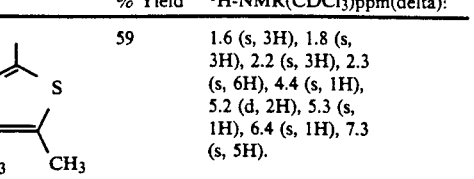 | 77 yellow oil | 1.35 (s, 3H), 1.56 (s, 3H), 2.22 (s, 3H), 4.42 (s, 1H), 4.60–4.74 (m, 2H), 5.24–5.42 (m, 3H), 5.79–5.96 (m, 1H), 6.52 (s, 1H), 7.32–7.34 (d, 1H), 8.70–8.74 (d, 1H). Infrared: 1810, 1760 cm⁻¹. |
| allyl | (structure) | 59 yellow oil | 1.42 (s, 3H), 1.62 (s, 3H), 2.28 (s, 3H), 2.48 (s, 3H), 4.5 (s, 1H), 4.6–4.8 (m, 2H), 5.28–5.47 (m, 2H), 5.82–6.0 (m, 1H), 6.3 (s, 1H), 6.97 (s, 1H). Infrared: 1810, 1760, 1730 cm⁻¹. |

-continued

| Rᵃ | R¹³ | % Yield | ¹H-NMR(CDCl₃)ppm(delta): |
|---|---|---|---|
| benzyl | (structure) | 59 | 1.6 (s, 3H), 1.8 (s, 3H), 2.2 (s, 3H), 2.3 (s, 6H), 4.4 (s, 1H), 5.2 (d, 2H), 5.3 (s, 1H), 6.4 (s, 1H), 7.3 (s, 5H). |
| benzyl | (structure) | 22 | 1.22 (s, 3H), 1.5 (s, 3H), 2.18 (s, 3H), 2.42 (s, 3H), 4.5 (s, 1H), 5.16–5.36 (m, 3H), 6.18 (s, 1H), 6.48 (s, 1H), 7.4 (s, 5H). |
| benzyl | (structure) | 44 yellow foam | 1.26 (s, 3H), 1.5 (s, 3H), 2.2 (s, 3H), 2.4 (s, 3H), 4.4 (s, 1H), 5.16 (d, 2H), 5.3 (s, 1H), 6.6 (s, 1H), 6.8 (s, 1H), 7.3 (s, 5H). |
| allyl | (structure) | 36 foam | 1.40 (s, 3H), 1.60 (s, 3H), 2.27 (s, 3H), 2.65 (s, 3H), 4.20–4.8 (m, 3H), 5.1–6.2 (m, 4H), 6.41 (s, 1H). Infrared: 1815, 1760 cm⁻¹. |

EXAMPLE 68

A. Benzyl 6-beta(thiazol-2-yl)acetoxymethyl-1,1-dioxopenicillanate

To a solution of 74.6 g (134 mmole) benzyl 6-bromo-6-(thiazol-2-yl)acetoxymethyl-1,1-dioxopenicillanate in 850 ml benzene was added 43.99 g (151.2 mmole) tri-n-butyltin hydride. The mixture was heated at reflux for 5.5 hours and allowed to stand overnight. The solvent was evaporated in vacuo, the residue taken up in hexane and extracted with acetonitrile (2×250 ml). The acetonitrile layer was evaporated, the residue slurried in ethyl ether, filtered and the cake washed with ether to give 33.28 g of colorless crystals. Another 2.8 g was obtained by evaporation of the filtrate to dryness. The residue was taken up in benzene and 10 g tri-n-butyltin hydride was added. The mixture was refluxed for one hour and worked up as for the first crop; combined yield 56.3%.

The first crop, above, was purified by column chromatography on silica gel, eluting with 9:1 chloroform/ethyl acetate. The product fractions were concentrated, slurried with 4:1 ethyl ether/ethyl acetate, filtered, washed with ether to afford 22.6 g white solid. ¹H-NMR(CDCl₃)ppm (delta): 1.25 (s, 3H), 1.53 (s, 3H), 2.1 (s, 3H), 4.58 (s, 1H), 4.80 (d, 1H), 5.2 (dd, 1H), 5.22 (q, 2H), 6.75 (d, 1H), 7.35 (s, 5H), 7.4 (d, 1H), 7.8 (d, 1H). ¹³C-NMR(CDCl₃)ppm (delta): 17.7, 19.9, 20.5, 54.5, 63.06, 63.6, 63.8, 64.5, 68.1, 121.8, 128.8, 128.9, 134.3, 142.6, 164.6, 166.5, 169.2, 170.5.

B. The following compounds were obtained in a similar manner by debromination of the remaining compounds provided in Example 67.

Structure 1

$R^{13}-CH(OCOCH_3)$ attached to β-lactam-sulfone with $CH_3, CH_3$ and $COOR^a$

| $R^a$ | $R^{13}$ | % Yield | $^1$H-NMR(CDCl$_3$) ppm(delta): |
|---|---|---|---|
| benzyl | benzothiazol-2-yl | 39 | 1.3 (s, 3H), 1.55 (s, 3H), 2.19 (s, 3H), 4.5 (s, 1H), 4.79 (d, 1H), 5.2 (m, 3H), 6.79 (d, 1H), 7.32 (m, 7H), 7.9 (m, 2H). |
| benzyl | 1-methyl-3-methyl-1,2,4-triazol | 72 | 1.29 (s, 3H), 1.55 (s, 3H), 2.10 (s, 3H), 4.03 (s, 3H), 4.5 (s, 1H), 4.78 (d, 1H), 4.87 (dd, 1H), 5.25 (q, 2H), 6.53 (d, 1H), 7.38 (s, 5H), 7.89 (s, 1H). |
| benzyl | pyrazin-2-yl | 46 yellow solid | 1.3 (s, 3H), 1.55 (s, 3H), 4.45 (s, 1H), 4.6–5.1 (m, 2H), 5.2 (m, 2H), 6.6 (dd, 1H), 7.35 (s, 5H), 8.6 (m, 2H), 8.83 (m, 1H). |
| allyl | 4-methyl-1,2,3-thiadiazol | 70 oil | 1.44 (s, 3H), 1.62 (s, 3H), 2.10 (s, 3H), 4.51 (s, 1H), 4.60–4.80 (m, 2H), 4.89–4.91 (d, 1H), 5.26–5.42 (m, 3H), 5.86–5.99 (m, 1H), 6.88–6.92 (d, 1H), 8.82 (s, 1H). Infrared: 1795, 1750. |
| allyl | 3-methylisothiazol | 51 (MP isomer) + 11 (LP isomer) | MP isomer: 5.84–6.00 (m, 1H), 6.28–6.42 (m, 2H), 6.62–6.77 (d, 1H), 7.38–7.48 (d, 1H), 8.64–8.70 (d, 1H). White crystals, Infrared (KBr): 1807, 1760 cm$^{-1}$. |
| allyl | 2-methyl-4-methylthiazol | 31 yellow oil | 1.46 (s, 3H), 1.64 (s, 3H), 2.14 (s, 3H), 2.48 (s, 3H), 4.5 (s, 1H), 4.6–4.9 (m, 3H), 5.2–5.26 (dd, 1H), 5.3–5.6 (m, 2H), 5.86–6.1 (m, 1H), 6.7 (d, 1H), 7.0 (s, 1H). Infrared: 1810, 1760 cm$^{-1}$. |

-continued

| $R^a$ | $R^{13}$ | % Yield | $^1$H-NMR(CDCl$_3$) ppm(delta): |
|---|---|---|---|
| benzyl | 3,4-dimethyl-5-methylene-2H-thiazine | 43 m.p. 194.5–195.5° C. | 1.3 (s, 3H), 1.58 (s, 3H), 2.12 (s, 3H), 2.36 (d, 6H), 4.5 (s, 1H), 4.75 (d, 1H), 5.2–5.4 (dd, 3H), 6.6 (d, 1H), 7.4 (s, 5H). |
| benzyl | 3-methyl-5-methyl-isoxazol | 16 colorless solid single isomer | 1.28 (s, 3H), 1.55 (s, 3H), 2.1 (s, 3H), 2.4 (s, 3H), 4.5 (s, 1H), 4.8 (dd, 1H), 5.25 (q, 1H), 6.15 (s, 1H), 6.5 (d, 1H), 7.4 (s, 5H). |
| benzyl | 2-methyl-4-methylthiazol | 43 | 1.3 (s, 3H), 1.58 (s, 3H), 2.14 (s, 3H), 2.48 (s, 3H), 4.52 (s, 1H), 4.8 (d, 1H), 5.16–5.36 (AB quartet and dd, 3H), 6.7 (d, 1H), 7.0 (s, 1H), 7.4 (s, 5H). |
| allyl | 3,5-dimethyl-1,2,4-oxadiazol | 44 3:1 mixture of isomers | 1.37–1.40 (d, 3H), 1.58–1.60 (d, 3H), 2.12–2.14 (d, 3H), 2.58 (s, 3H), 4.48 (s, 1H), 4.58–4.88 (m, 4H), 5.24–5.46 (m, 2H), 5.82–6.00 (m, 1H), 6.64–6.67 (d, 0.75H), 7.05–7.08 (d, 0.25H). Infrared: 1810, 1765 cm$^{-1}$. |

EXAMPLE 69

A. The benzyl esters provided above were converted to the corresponding carboxylic acids of the formula below where $R^b$ is H by hydrogenation over palladium-on-carbon catalyst by the method of Example 63.

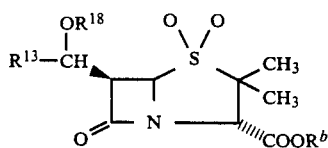

| $R^{13}$ | $R^{18}$ | % Yield | $^1$H-NMR(DMSO-d$_6$ or D$_2$O)ppm(delta): |
|---|---|---|---|
| 2-thiazolyl | CH$_3$C(O) | 74 white solid m.p. 145–155° C. (decomposed) | 1.45 (s, 3H), 1.53 (s, 3H), 2.10 (s, 3H), 4.48 (s, 1H), 5.0 (dd, 1H), 5.41 (d, 1H), 6.59 (d, 1H), 7.91 (m, 2H). $^{13}$C-NMR: 17.1036, 19.3736, 20.2771, 53.2954, 62.5971, 62.8347 63.3676, 64.5698, 122.6881, 142.4252, 164.3975, 167.8111, 168.7027, 170.8035. |

-continued

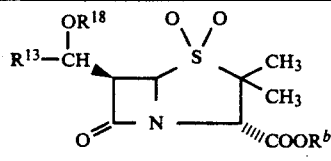

| $R^{13}$ | $R^{18}$ | % Yield | $^1$H-NMR(DMSO-d$_6$ or D$_2$O)ppm(delta): |
|---|---|---|---|
| benzothiazol-2-yl | CH$_3$C(O) | 45 | 1.53 (s, 3H), 1.65 (s, 3H), 2.17 (s, 3H), 4.54 (s, 1H), 4.87 (d, 1H), 5.13 (dd, 1H), 6.82 (d, 2H), 7.88 (d, 1H), 8.07 (d, 1H), 9.20 (bs, 1H). $^{13}$C-NMR: 17.6, 20.09, 20.5, 54.5 6?a;p?h?j 6?3,46?2?6.12?2?6.6, 135.3, 151.6 166.6, 169.2, 169.3, 170.6. |
| pyrazinyl | CH$_3$C(O) | 60 | (D$_2$O) 1.45 (s, 3H), 1.57 (s, 3H), 2.15 (s, 3H), 4.33 (s, 1H), 5.24 (d, 1H), 4.75-5.2 (~1H blocked by D$_2$O peak), 6.55 (d, 1H), 8.65-8.8 (m, 2H). Infrared (KBr): 3416, 1785, 1618 cm$^{-1}$. $^{13}$C-NMR: 17.6, 19.8, 20.4, 54.4, 64.1, 65.7, 68.1, 144.2, 145.2 145.5, 151.2, 172.7, 172.8 |
| 2,4,5-trimethylthiazol-? | CH$_3$C(O) | 85 | 1.48 (s, 3H), 1.55 (s, 3H), 2.15 (s, 3H), 2.28 (s, 3H), 2.32 (s, 3H), 4.3 (s, 1H), 4.85 (dd, 1H), 5.2 (d, 1H), 6.6 (d, 1H). Infrared (KBr): 1787, 1626, 1618 cm$^{-1}$. |
| 3,5-dimethylisoxazol-? | CH$_3$C(O) | 87 | 1.48 (s, 3H), 1.6 (s, 3H), 2.2 (s, 3H), 2.46 (s, 3H), 4.35 (s, 1H), 5.2 (d, 1H), 6.4 (s, 1H), 6.55 (d, 1H). Infrared (KBr): 1791, 1692, 1631 cm$^{-1}$. |
| 4-methylthiazol-2-yl | CH$_3$C(O) | 57 | 1.5 (s, 3H), 1.6 (s, 3H), 2.2 (s, 3H), 2.45 (s, 3H), 4.35 (s, 1H), 4.9 (dd, 1H), 5.25 (d, 1H), 6.7 (d, 1H), 7.3 (s, 1H). Infrared (KBr): 1787, 1657, 1626 cm$^{-1}$. |

B. 6-beta-(Thiazol-2-yl)acetoxymethyl-1,1-dioxopenicillanic acid obtained in Part A, above, was converted to the corresponding potassium salt by treatment of an aqueous slurry of the acid with an equimolar amount of potassium bicarbonate in water and purification by medium pressure liquid chromatography on a C$_{18}$ column*, eluting with 9:1 water/acetonitrile to obtain the corresponding potassium salt in 60% yield. $^1$H-NMR (DMSO-d$_6$)ppm (delta): 1.37 (s, 3H), 1.48 (s, 3H), 2.07 (s, 3H), 3.80 (s, 1H), 4.92 (dd, 1H), 5.12 (d, 1H), 6.55 (d, 1H), 7.89 (m, 2H). Infrared (KBr) 3454, 1788, 1630 cm$^{-1}$.
*C is octadecylsilicate

EXAMPLE 70

A. 6-(Benzothiazol-2-yl)methylene-1,1-dioxopenicillanic acid, mixture of E and Z isomers To a solution of 400 mg (0.91 mmole) 6-(benzothiazol-2yl)acetoxymethyl-1,1-dioxopenicillanic acid in 5 ml water was added a solution of 0.15 g (1.82 mmole) sodium bicarbonate in 2 ml water and the resulting mixture was stirred for two hours. The reaction mixture (pH 7.55) was freeze dried. The lyophilate was taken up in 8 ml water, adjusted to pH 3.5 with dilute hydrochloric acid, extracted with ethyl acetate, the organic layers dried (MgSO$_4$) and the solvent evaporated in vacuo. The resulting product was shown to be a 60:40 mixture of (E) and (Z) isomers by its NMR spectrum. $^1$H-NMR(CDCl$_3$) ppm (delta): 1.55 (s, 1.2H), 1.6 (s, 1.8H), 1.65 (s, 1.2H), 1.67 (s, 1.8H), 4.55 (s, 0.6H), 4.58 (s, 0.4H), 5.38 (s, 0.4H), 5.74 (s, 0.6H), 7.44 (s, 0.4H), 7.48 (s, 0.6H), 7.5 (m, 4H), 7.89 (d, 1H), 8.07 (d, 0.4H), 8.15 (d, 0.6H).

B. Similar treatment of the appropriate 6-R$^{13}$-CH(OAc)-substituted-1,1-dioxopenicillanic acid, provided above, afforded the compound of the formula below as a mixture of (E) and (Z) isomers.

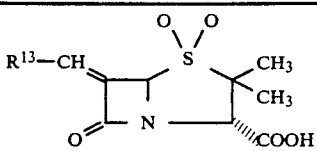

| R[13] | % Yield | $^1$H-NMR(D[2]O)ppm(delta): |
|---|---|---|
| N—N—CH[3] (structure) (Na salt) | 84 60:40 mixture of (E) and (Z) isomers | 1.54 (s, 3H), 1.62 (s, 3H), 4.04 (s, 3H), 4.35 (s, 1H), 5.7 (s, 0.6H), 5.95 (s, 0.4H), 7.26 (s, 0.6H), 7.55 (s, 0.4H), 8.09 (s, 2H). |

EXAMPLE 71

A. Potassium 6-bromo-6-(thiazol-2-yl)acetoxymethyl-1,1-dioxopenicillanate

Reaction of 96 mg (0.2 mmole) allyl 6-bromo-6-(thiazol-2-yl)acetoxymethyl-1,1-dioxopenicillanate (provided in Example 67) by the method of Example 60 for 10 minutes and worked up as described to provide 46 mg (48%) of yellow solid product. $^1$H-NMR(D$_2$O)ppm (delta): 1.45 (s, 3H), 1.6 (s, 3H), 4.4 (s, 1H), 5.55 (s, 1H), 6.85 (s, 1H), 7.72 (d, 1H), 7.86 (d, 1H).

B. Potassium 6-bromo-6-(thiazol-2-yl)hydroxymethyl-1,1-dioxopenicillanate

Similarly, reaction of 220 mg allyl 6-bromo-6-(thiazol-2-yl)hydroxymethyl-1,1-dioxopenicillanate (provided in Example 6) by the above method for 20 minutes gave a 52% yield of the title salt as a pale yellow solid. $^1$H-NMR(DMSO-d$_6$)ppm (delta): 1.35 (s, 3H), 1.47 (s, 3H), 3.75 (s, 0.4H), 3.83 (s, 0.6H), 5.3 (d, 0.4H), 5.32 (d, 0.6H), 5.45 (s, 0.6H), 5.5 (s, 0.4H), 7.6–8.0 (m, 2H). Infrared (KBR): 3442, 1794, 1633 cm$^{-1}$.

EXAMPLE 72

Potassium (6-beta, 8S)-6-(thiazol-2yl)-hydroxymethylpenicillanate

A. Allyl 6-bromo-6-(thiazol-2-yl)hydroxymethylpenicillanate

To a solution of 9.971 g (24.99 mmole) allyl 6,6-dibromopenicillanate in 150 ml dry tetrahydrofuran cooled to −78° C. under nitrogen, was added 8.77 ml of 2.85M (24.99 mmole) methylmagnesium bromide in THF* and the mixture stirred for 15 minutes. A solution of 2.824 g (24.99 mmole) thiazol-2-carboxaldehyde in 5 ml THF was added and the mixture was stirred again for 20 minutes at −78° C. The reaction was quenched by addition of 1.43 ml (24.99 mmole) glacial acetic acid, the mixture stirred for 10 minutes, then allowed to warm to room temperature. It was then poured into water, extracted with 2×250 ml ethyl acetate, the extracts washed with water (2×250 ml), dried (MgSO$_4$) and the solvent evaporated in vacuo to give 10.36 g orange oil. The oil was purified by column chromatography on silica gel eluting with 9:1 chloroform/ethyl acetate to yield 4.54 g yellow solid (mixture of isomers) and 0.443 g yellow foam, more polar isomer only, (total yield 46%). For the yellow foam: $^1$H-NMR(CDCl$_3$)ppm (delta): 1.56 (s, 3H), 1.76 (s, 3H), 4.60 (s, 1H), 4.7 (m, 2H), 4.9–6.4 (m, 6H), 7.45 (m, 1H), 7.8 (m, 1H).

*In subsequent runs other solvents such as benzene, toluene and methylene chloride were found to be useful.

B. Allyl 6-beta-(thiazol-2-yl)hydroxymethylpenicillanate

The more polar isomer from Part A, 200 mg (0.462 mmole) was dissolved in 1 ml benzene and 0.183 ml (0.693 mmole, 1.5 equivalents) tri-n-butyltin hydride in benzene was added. The mixture was heated at reflux for three hours and allowed to stand overnight at room temperature. The solvent was evaporated in vacuo, the residue taken up in acetonitrile, washed with hexane and evaporated to a small volume which was placed on a silica gel column and eluted with chloroform to yield 73 mg (45%) of the desired product. $^1$H-NMR(CDCl$_3$)ppm (delta): 1.65 (s, 3H), 1.87 (s, 3H), 3.8–4.4 (m, 1H), 4.05–4.3 (dd, 1H), 4.65 (s, 1H), 4.78 (m, 2H), 5.3–5.6 (m, 2H), 5.6–6.3 (m, 3H), 7.45 (m, 1H), 7.85 (m, 1H).

C. The product obtained in Part B, 73 mg (0.206 mmole), was converted to potassium salt by the method of Example 60 to provide 58 mg (80%) of the title compound as a yellow solid. $^1$H-NMR, 300 MHz, (D$_2$O)ppm (delta): 1.36 (s, 3H), 1.55 (s, 3H), 4.13 (dd, 1H), 4.18 (s, 1H), 5.32 (d, 1H), 5.41 (d, 1H), 7.56 (d, 1H), 7.60 (d, 1H).

EXAMPLE 73

A. By employing the appropriate aldehyde, R$^{13}$CHO in place of thiazol-2-carboxaldehyde in the procedure of Example 72, Part A, afforded the corresponding compounds of the formula below in like manner.

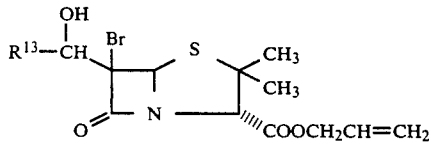

| R[13] | % Yield | $^1$H-NMR(CDCl[3]) ppm (delta): |
|---|---|---|
| (pyrazine) | 20, Isomer A (white crystals) 13, Isomer B (yellow oil) | Isomer A: 1.46 (s, 3H), 1.64 (s, 3H), 4.42 (d, 1H), 4.50 (s, 1H), 4.64 (m, 2H), 5.26–5.50 (m, 3H), 5.84 (s, 1H), 5.8–6.0 (m, 1H), 8.58 (d, 2H), 8.9 (s, 1H), $^{13}$C-NMR(CDCl$_3$): 26.4, 32.5, 64.4, 66.1, 69.8, 70.9, 73.7, 74.9, 119.6, 131.0, 143.0, 144.3, 144.6, 152.1, 166.8, 167.8 ppm. Isomer B: 1.45 (s, 3H), 1.63 (s, 3H), 4.56 (s, 1H), 4.65 (m, 2H), 5.1–5.5 (m, 4H), 5.6–6.0 (m, 1H), 5.91 (s, 1H), 8.57 (m, 2H), 8.78 (m, 1H). $^{13}$C-NMR(CDCl$_3$): 26.27, 32.57, 64.30, 66.19, 69.94, 70.77, 72.38, 74.73, 119.70, 130.98, 143.30, 144.57, 144.70, 152.04, 166.99, 167.99 ppm. |
| 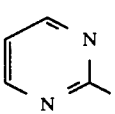 (pyrazine) | 25, (Isomer A, 8S) | 1.52 (s, 3H), 1.70 (s, 3H), 4.64 (s, 1H), 4.72 (m, 2H), 4.86 (d, 1H), 5.34–5.48 (m, 3H), 5.91 (s, 1H), 5.92–6.05 (m, 1H), 7.39 (t, 1H), 8.87 (d, 2H). |

-continued

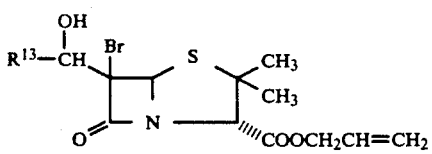

| $R^{13}$ | % Yield | $^1$H-NMR(CDCl$_3$) ppm (delta): |
|---|---|---|
| pyrimidin-2-yl | 40, (Isomer B, 8R) | 1.52 (s, 3H), 1.71 (s, 3H), 4.61 (s, 1H), 4.72 (m, 2H), 4.98 (d, 1H), 5.30–5.52 (m, 3H), 5.90–6.04 (m, 1H), 6.10 (s, 1H), 7.40 (t, 1H), 8.85 (d, 2H). |
| 2-C$_6$H$_5$-1,2,3-triazol-4-yl | 83 foam | 1.49 (s, 3H), 1.69 (s, 3H), 3.56 (d, 0.7H), 3.89 (d, 0.3H), 4.7 (m, 3H), 5.5 (m, 3H), 5.9 (m, 2H), 7.53 (m, 3H), 8.14 (m, 3H). |
| benzothiazol-2-yl | 97 (crude) mixture of isomers | |
| pyridin-2-yl | | |
| pyridin-4-yl | | |
| 5-phenyl-2-(dimethoxymethyl)-imidazol-... | 100 (crude) (mixture with 5-phenyl isomer) | Brown oil; Used in next step without purification |
| 1-methylbenzimidazol-2-yl | | Used in next step without isolation. |
| 1-ethylbenzimidazol-2-yl | | Orange-red oil, used in next step without purification. |
| 1-propylbenzimidazol-2-yl | | Gold oil, used in next step without purification. |

-continued

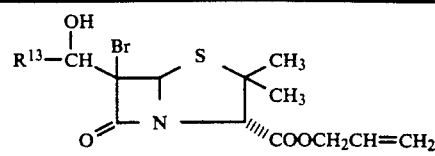

| $R^{13}$ | % Yield | $^1$H-NMR(CDCl$_3$) ppm (delta): |
|---|---|---|
| benzoxazol-2-yl | | Orange oil, used in next step without purification. |
| 6-methoxybenzothiazol-2-yl | 100% | Orange oil used in next step without purification. |
| 1-methylimidazol-2-yl | | Gold oil, used in next step without purification. |
| 5-phenyl-1-methylimidazol-2-yl | | Gold oil, used in next step without purification. |
| 5,6-dimethyl-1-methylbenzimidazol-2-yl | | Gold oil, used in next step without purification. |
| (3,5-dimethyl and 3,6-dimethyl mixture) | | Used in next step without isolation. |
| 6-methoxy-1-methylbenzimidazol-2-yl | | Orange glass, used in next step without purification. |
| 5-methoxy-1-methylbenzimidazol-2-yl | | Orange glass, used in next step without purification. |

B. Debromination of the above compounds by the method of Example 72, Part B, bave the following compounds.

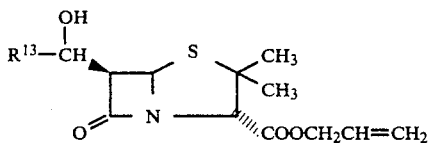

| $R^{13}$ | % Yield | $^1$H-NMR(CDCl$_3$) ppm (delta): |
|---|---|---|
| ![pyrazinyl] (From isomer A, 8S) | 57 oil | 1.5 (s, 3H), 1.7 (s, 3H), 4.05 (dd, 1H), 4.35 (s, 1H), 4.5 (d, 1H), 4.65 (m, 2H), 5.25–5.45 (m, 3H), 5.55 (d, 1H), 5.9–6.0 (m, 1H), 8.6 (m, 2H), 8.85 (s, 1H). |
| ![pyrazinyl] (From isomer B, 8S) | 59 | 1.5 (s, 3H), 1.8 (s, 3H), 4.15 (dd, 1H), 4.25 (bs, 1H), 4.55 (s, 1H), 4.7 (m, 2H), 5.2–6.2 (m, 5H), 8.67 (bs, 2H), 9.00 (bs, 1H). |
| ![pyrimidinyl] (From isomer A, 8S) | 35 oil | 1.51 (s, 3H), 1.74 (s, 3H), 4.01 (dd, 1H), 4.44 (d, 1H), 4.60 (s, 1H), 4.70 (d, 2H), 5.40 (m, 3H), 5.60 (d, 1H), 5.96 (m, 1H), 7.34 (t, 1H), 8.80 (d, 2H). |
| ![pyrimidinyl] (From isomer B, 8R) | 65 | 1.52 (s, 3H), 1.78 (s, 3H), 4.23 (m, 2H), 4.64 (s, 1H), 4.71 (d, 2H), 5.30–5.46 (m, 3H), 5.53 (d, 1H), 5.90–6.04 (m, 1H), 7.34 (t, 1H), 8.85 (d, 2H). |
| ![phenyl-triazolyl] | 100 | 1.47 (s, 3H), 1.67 (s, 3H), 4.16 (m, 2H), 4.64 (m, 3H), 5.47 (m, 4H), 5.94 (m, 1H), 7.43 (m, 3H), 8.02 (m, 3H). |
| ![benzothiazolyl] (8R) | 81 (no purification) | 1.42 (s, 3H), 1.7 (s, 3H), 4.4 (d of d, J=4 and 8, 1H), 4.5 (s, 1H), 4.65 (m, 2H), 5.2–6.3 (m, 3H), 5.6 (d, J=4, 1H), 5.6 (d, J=8, 1H), 7.2–7.6 (m, 2H), 7.8–8.1 (m, 2H). |
| ![benzothiazolyl] (8S) | 36 (after purification) | 1.45 (s, 3H), 1.55 (s, 3H), 4.15 (d of d, 1H), 4.5 (s, 1H), 4.65 (m, 2H), 5.2–6.4 (m, 5H), 7.2–7.6 (m, 2H), 7.8–8.2 (m, 2H). |
| ![2-pyridyl] | | |
| ![4-pyridyl] | | |

-continued

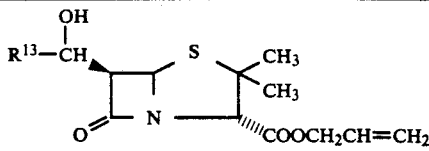

| R[13] | % Yield | $^1$H-NMR(CDCl$_3$) ppm (delta): |
|---|---|---|
| C$_6$H$_5$-[imidazole with NH]<br>(From 1-Di-methoxy-methyl-4-phenyl precursor in Part A) | 20<br>(crude)<br>11 LP (6β, 8S)<br>2 MP (6α, 8R) | LP isomer: 1.38 (s, 3H), 1.53 (s, 3H), 4.15 (dd, 1H), 4.41 (s, 1H), 4.57 (d, 2H), 5.10–5.46 (m, 4H), 5.70–5.92 (m, 1H), 7.00–7.43 (m, 4H), 7.43–7.74 (m, 2H). |
| [benzimidazole N-CH$_3$] | 16<br>(purified)<br>gold foam | 1.3 (s, 3H), 1.54 (s, 3H), 3.68 (s, 3H), 4.42 (s, 1H), 4.56 (m, 2H), 5.1–5.4 (m, 3H), 5.48 (d, 1H), 5.76–5.94 (m, 1H), 7–7.3 (m, 3H), 7.54 (d, 1H). |
| [benzimidazole N-C$_2$H$_5$] | 68 (mixture of isomers)<br>5 (6β, 8R)<br>8 (6β, 8S)<br>by rechromatography | 8R isomer:<br>1.40–1.55 (m, 6H), 1.75 (s, 3H), 4.1–4.4 (m, 2H), 4.52 (m, 2H), 4.6 (dd, 1H), 4.7 (d, 2H), 5.2–5.5 (m, 3H), 5.8–6.1 (m, 1H), 7.2–7.5 (m, 3H), 7.7–7.9 (m, 1H).<br>8S isomer:<br>1.4–1.55 (m, 6H), 1.64 (s, 3H), 4.14 (q, 1H), 4.42 (q, 1H), 4.5 (s, 1H), 4.64 (m, 2H), 5.2–5.5 (m, 2H), 5.9 (d, 1H), 5.8–6.0 (m, 1H), 7.1–7.4 (m, 3H), 7.65 (m, 1H). |
| [benzimidazole N-CH$_2$CH$_2$CH$_3$] | 7.5<br>(6β, 8R)<br><br><br>14<br>(6β, 8S) | 0.98 (t, 3H), 1.5 (s, 3H), 1.7 (s, 3H), 1.87 (m, 2H), 4.0–4.4 (m, 2H), 4.4–4.6 (m, 2H), 4.68 (d, 2H), 5.2–5.5 (m, 3H), 5.7 (m, 1H), 5.84–6.00 (m, 1H), 7.2–7.3 (m, 3H), 7.66–7.8 (m, 1H).<br>1.0 (t, 3H), 1.40 (s, 3H), 1.64 (s, 3H), 1.9 (m, 2H), 4.05 (m, 1H), 4.3 (m, 1H), 4.5 (s, 1H), 4.6–4.7 (m, 3H), 5.2–5.4 (m, 4H), 5.6 (d, 1H), 5.84–6.00 (m, 1H), 7.1–7.3 (m, 3H), 7.6 (m, 1H). |
| [benzoxazole] | yellow oil,<br>30<br>(6β, 8S) | 1.44 (s, 3H), 1.64 (s, 3H), 4.3 (dd, 1H), 4.65 (s, 1H), 4.66 (d, 2H), 5.2–5.6 (m, 3H), 5.62 (d, 1H), 5.8–6.1 (m, 1H), 7.32–7.42 (m, 2H), 7.52–7.64 (m, 1H), 7.7–8.2 (m, 1H). |
| [benzothiazole] | — | mixture of isomers |
| [imidazole N-CH$_3$] | gold oil<br>13<br>4:1 mixture of<br>(6β, 8S) and<br>(6β, 8R) | 1.38 (s, 2.4H), 1.48 (s, 0.6H), 1.6 (s, 2.4H), 1.67 (s, 0.6H), 3.7 (s, 0.6H), 3.74 (s, 2.4H), 4.12 (dd, 0.2H), 4.34 (dd, 0.8H), 4.4 (s, 0.2H), 4.44 (s, 0.8H), 4.63 (m, 2H), 5.1–5.36 (m, 3.2H), 5.42 (d, 0.8H), 5.8–6.0 (m, 1H), 6.8–7.3 (m, 2H). |
| C$_6$H$_5$-[imidazole N-CH$_3$] | 27<br>(6β, 8S)<br><br><br><br><br>13<br>(6β, 8R) | 1.3 (s, 3H), 1.56 (s, 3H), 3.0 (s, 3H), 4.45 (s, 3H), 4.6 (m, 2H), 4.66 (dd, 1H), 5.0 (d, 1H), 5.2–5.4 (m, 2H), 5.4 (d, 1H), 5.8–6.0 (m, 1H), 6.76 (s, 1H), 7.1–7.5 (m, 3H), 7.5–7.7 (m, 2H).<br>1.5 (s, 3H), 1.68 (s, 3H), 3.28 (s, 3H), 4.36 (dd, 1H), 4.44 (s, 1H), 4.66 (m, 2H), 5.14 (d, 1H), 5.24–5.5 (m, |

-continued

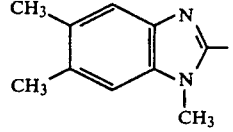

| R[13] | % Yield | $^1$H-NMR(CDCl$_3$) ppm (delta): |
|---|---|---|
| | | 2H), 5.7 (d, 1H), 5.8–6.0 (m, 1H), 6.9 (s, 1H), 7.2–7.5 (m, 3H), 7.6–7.8 (m, 2H). |
| 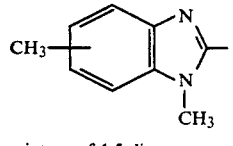 | 18 (6β, 8S) | 1.3 (s, 3H), 1.58 (s, 3H), 2.25 (s, 3H), 2.3 (s, 3H), 3.65 (s, 3H), 4.45 (s, 1H), 4.54 (dd, 1H), 4.6 (m, 2H), 5.2–5.4 (m, 3H), 5.48 (d, 1H), 5.8–6.0 (m, 1H), 6.77 (s, 1H), 7.26 (d, 1H). |
| | 16 (6β, 8R) | 1.44 (s, 3H), 1.62 (s, 3H), 2.18 (s, 3H), 2.26 (s, 3H), 3.62 (s, 3H), 4.34 (s, 1H), 4.4 (dd, 1H), 4.6 (d, 2H), 5.2–5.4 (m, 3H), 5.44 (d, 1H), 5.8–6.0 (m, 1H), 6.88 (s, 1H), 7.24 (m, 1H). |
| 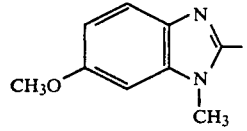<br>mixture of 1,5-di-methyl and 1,6-di-methyl compounds | 9.6<br>Two isomers (6β, 8S)<br>plus 14<br>Two isomers (6β, 8R) | (8S)-isomers:<br>1.42 (s, 3H), 1.68 (s, 3H), 2.46 (s, 1.5H), 2.5 (s, 1.5H), 3.82 (s, 3H), 4.52 (s, 3H), 4.6 (2dd, 1H), 4.7 (m, 2H), 5.2–5.7 (m, 4H), 5.8–6.05 (m, 1H), 7.0–7.3 (m, 2H), 7.4–7.7 (m, 1H).<br>(8R)-isomers:<br>1.44 (s, 3H), 1.64 (s, 3H), 2.32 (s, 1.5H), 2.4 (s, 1.5H), 3.6 (s, 1.5H), 3.64 (s, 1.5H), 4.36 (s, 1H), 4.4 (dd, 1H), 4.6 (m, 2H), 5.2–5.5 (m, 4H), 5.8–6.0 (m, 1H), 6.8–7.2 (m, 2H), 7.2–7.6 (m, 1H). |
| 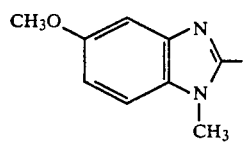 | 13 (6β, 8S) | 1.32 (s, 3H), 1.58 (s, 3H), 3.66 (s, 3H), 3.78 (s, 3H), 4.46 (s, 1H), 4.52 (dd, 1H), 4.6 (d, 1H), 5.2–5.4 (m, 3H), 5.5 (d, 1H), 5.8–6.0 (m, 1H), 6.48 (d, 1H), 6.86 (dd, 1H), 7.43 (d, 1H). |
| | 10 (6β, 8R) | 1.46 (s, 3H), 1.66 (s, 3H), 3.66 (s, 3H), 3.8 (s, 3H), 4.4 (m, 2H), 4.64 (d, 2H), 5.2–5.4 (m, 3H), 5.62 (d, 1H), 5.82–6.0 (m, 1H), 6.58 (d, 1H), 6.8 (dd, 1H), 7.5 (d, 1H). |
| 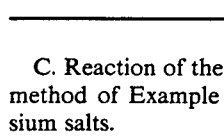 | 24 (6β, 8S) | 1.28 (s, 3H), 1.54 (s, 3H), 3.68 (s, 3H), 3.72 (s, 3H), 4.4 (s, 1H), 4.52 (dd, 1H), 4.56 (m, 2H), 5.1–5.4 (m, 3H), 5.48 (d, 1H), 5.76–5.9 (m, 1H), 6.8 (dd, 1H), 6.96–7.1 (m, 1H), 7.28 (s, 1H). |
| | 15 (6β, 8R) | 1.46 (s, 3H), 1.66 (s, 3H), 3.7 (s, 3H), 3.8 (s, 3H), 4.4 (s, 1H), 4.4 (dd, 1H), 4.64 (d, 2H), 5.2–5.4 (m, 2H), 5.4 (d, 1H), 5.5 (d, 1H), 5.8–6.0 (m, 1H), 6.8–7.0 (m, 1H), 7.1–7.25 (m, 1H), 7.28 (s, 1H). |

C. Reaction of the allyl esters provided above by the method of Example 60 provided the following potassium salts.

| R[13] | % Yield | C$_8$ Stereo chemistry | $^1$H-NMR(DMSO-d$_6$)ppm(delta): |
|---|---|---|---|

-continued
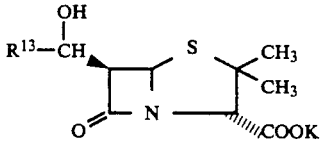
| R13 | | Stereo- | |
|---|---|---|---|
| 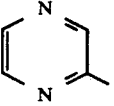<br>(Isomer A) | 75 | 8R | 1.46 (s, 3H), 1.56 (s, 3H), 3.76 (s, 1H), 4.13 (dd, 1H), 5.05 (d, 1H), 5.4 (d, 1H), 8.58 (d, 2H), 8.72 (s, 1H). Infrared (KBr): 3478, 1761, 1607 cm$^{-1}$. |
| 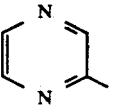<br>(Isomer B) | 82 | 8S | 1.42 (s, 3H), 1.65 (s, 3H), 4.25 (s, 3H), 4.27 (dd, 1H), 5.3 (d, 1H), 5.35 (d, 1H), 8.6–8.7 (m, 2H), 8.8 (m, 1H). |
| 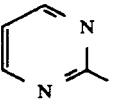<br>(Isomer A) | 94 | 8S | (D$_2$O): 1.32 (s, 3H), 1.54 (s, 3H), 4.18 (s, 1H), 4.14–4.19 (m, 1H), 5.19 (d, 1H), 5.25 (d, 1H), 7.45 (t, 1H), 8.75 (d, 2H). |
| 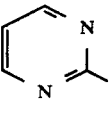<br>(Isomer B) | 95 | 8R | (D$_2$O): 1.44 (s, 3H), 1.58 (s, 3H), 4.12 (s, 1H), 4.18 (m, 1H), 5.22 (d, 1H), 5.49 (d, 1H), 7.46 (t, 1H), 8.75 (d, 2H). |
| 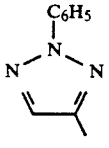 | 97 | 8R | 1.47 (s, 3H), 1.58 (s, 3H), 3.79 (s, 1H), 4.13 (dd, 1H), 5.2 (d, 1H), 5.4 (d, 1H), 5.95 (bs, 1H), 7.45 (t, 1H), 7.60 (t, 2H), 8.03 (d, 2H), 8.16 (s, 1H). |
| 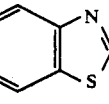 | 85 | 8S | 1.48 (s, 3H), 1.67 (s, 3H), 4.27 (d of d, J=4 and 10, 1H), 4.3 (s, 1H), 5.45 (d, J=4, 1H), 5.57 (d, J=10, 1H), 7.45–7.65 (m, 2H), 8.04 (t, J=8, 2H). IR(KBr): 3424, 1765, 1746, 1592 cm$^{-1}$. |
| 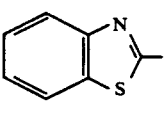 | 91 | 8R | 1.42 (s, 3H), 1.56 (s, 3H), 4.16 (s, 1H), 4.25 (d of d, J=4 and 8, 1H), 5.46 (d, J=4, 1H), 5.5 (d, J=8, 1H), 7.4–7.6 (m, 2H), 7.8–8.05 (m, 2H). |
| 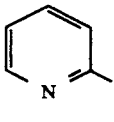 | | | |
| 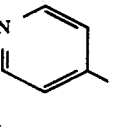 | | | |
| 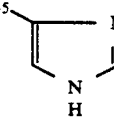 | 49 | 8S | (D$_2$O): 1.46 (s, 3H), 1.66 (s, 3H), 4.27 (s, 1H), 4.30 (dd, 1H), 5.26 (d, 1H), 5.37 (d, 1H), 7.30–7.40 (m, 1H), 7.40–7.54 (m, 3H), 7.66–7.80 (m, 2H), IR(KBr): 1590, 1735 cm$^{-1}$. |

-continued

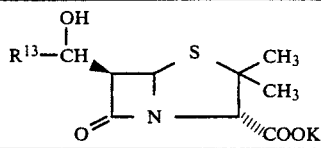

| R[13] | % Yield | chemistry | $^1$H-NMR(D$_2$O)ppm(delta): |
|---|---|---|---|
| benzimidazole, N-CH$_3$, 2-methyl | 87 (crude) 34 (purified) solid | (6β, 8S) | 1.26 (s, 3H), 1.48 (s, 3H), 3.76 (s, 3H), 4.16 (s, 1H), 4.36 (dd, 1H), 5.3–5.45 (m, 2H), 7.2–7.3 (m, 2H), 7.3–7.6 (m, 2H). |
| benzimidazole, N-C$_2$H$_5$, 2-methyl | 59 | (6β, 8S) | 1.4–1.45 (m, 6H), 1.6 (s, 3H), 4.3 (s, 1H), 4.3–4.75 (m, 3H), 5.4–5.6 (m, 2H), 7.3–7.5 (m, 2H), 7.6 (d, 1H), 7.7 (d, 1H). |
| benzimidazole, N-C$_2$H$_5$, 2-methyl | 30 | (6β, 8R) | 1.3–1.5 (m, 3H), 1.58 (s, 3H), 1.65 (s, 3H), 4.25 (s, 3H), 4.3–4.5 (m, 2H), 4.65 (dd, 1H), 5.56 (d, 1H), 5.65 (d, 1H), 7.4 (m, 2H), 7.6–7.8 (m, 2H). |
| benzimidazole, N-CH$_2$CH$_2$CH$_3$, 2-methyl | 40 | (6β, 8R) | 0.9 (t, 3H), 1.6 (s, 3H), 1.72 (s, 3H), 1.8–2.0 (m, 2H), 4.26 (s, 1H), 4.2–4.4 (m, 2H), 4.65 (dd, 1H), 5.56 (d, 1H), 5.7 (d, 1H), 7.3–7.5 (m, 2H), 7.67 (d, 1H), 7.79 (d, 1H). IR(KBr) cm$^{-1}$: 3423, 1748, 1599. |
| benzimidazole, N-CH$_2$CH$_2$CH$_3$, 2-methyl | 90 | (6β, 8S) | 0.95 (t, 3H), 1.42 (s, 3H), 1.62 (s, 3H), 1.9 (m, 2H), 3.39 (s, 1H), 4.3 (m, 2H), 4.5 (dd, 1H), 5.4–5.6 (m, 2H), 7.3–7.5 (m, 2H), 7.6 (m, 1H), 7.7 (m, 1H). IR(KBr) cm$^{-1}$: 3473, 1756, 1604. |
| benzoxazole, 2-methyl | 75 | — | 1.44 (s, 3H), 1.6 (s, 3H), 4.26 (s, 3H), 4.32 (dd, 1H), 5.46 (d, 1H), 5.5 (d, 1H), 7.4–7.8 (m, 4H). IR(KBr) cm$^{-1}$: 3422, 1763, 1609. |
| benzothiazole, 6-OCH$_3$ | 22 yellow solid 98% pure by HPLC | (6β, 8S) | 1.44 (s, 3H), 1.64 (s, 3H), 3.84 (s, 3H), 4.22 (dd, 1H), 4.28 (s, 1H), 5.4 (d, 1H), 5.5 (d, 1H), 7.1 (m, 1H), 7.42 (d, 1H), 7.82 (d, 1H). IR(KBr) cm$^{-1}$: 3442, 1762, 1743, 1589. |
| imidazole, N-CH$_3$, 2-methyl | — | 4:1 mixture of (6β, 8S) and (6β, 8R) | 1.4 (s, 2.4H), 1.54 (s, 0.6H), 1.62 (s, 2.4H), 1.64 (s, 0.6H), 3.72 (s, 0.6H), 3.75 (s, 2.4H), 4.2 (s, 0.2H), 4.25 (s, 0.8H), 4.32 (dd, 0.8H), 4.46 (dd, 0.2H), 5.26 (d, 0.8H), 5.3 (d, 0.2H), 5.38 (d, 0.8H), 5.6 (d, 0.2H), 6.79 (s, 0.8H), 7.00 (s, 0.2H), 7.15 (s, 1H). IR(KBr) cm$^{-1}$: 3452, 1757, 1663. |
| imidazole, 4-C$_6$H$_5$, N-CH$_3$, 2-methyl | 93 | (6β, 8S) | 1.42 (s, 3H), 1.62 (s, 3H), 3.72 (s, 3H), 4.28 (s, 1H), 4.42 (dd, 1H). |

-continued

| $R^{13}$— group | Yield | Stereo | NMR / IR |
|---|---|---|---|
| 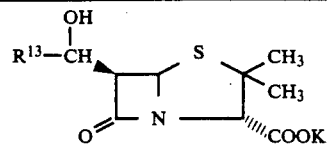 | 88 | (6β, 8R) | 1.55 (s, 3H), 1.7 (s, 3H), 3.7 (s, 3H), 4.24 (s, 1H), 4.48 (dd, 1H) 5.4 (d, 1H), 5.63 (d, 1H), 7.2–7.5 (m, 3H), 7.7 (d, 2H). IR(KBr) cm$^{-1}$: 3395, 1756, 1603. |
| 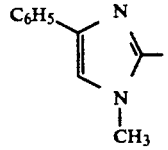 | 100 white solid | (6β, 8S) | 1.3 (s, 3H), 1.5 (s, 3H), 2.12 (s, 3H), 2.16 (s, 3H), 3.7 (s, 3H), 4.2 (s, 1H), 4.36 (dd, 1H), 5.36 (d, 1H), 5.4 (d, 1H), 7.08 (s, 1H), 7.3 (s, 1H). |
| 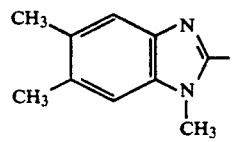 | 93 yellow solid | (6β, 8R) | 1.46 (s, 3H), 1.6 (s, 3H), 2.22 (s, 3H), 2.26 (s, 3H), 3.68 (s, 3H), 4.12 (s, 1H), 4.46 (dd, 1H), 5.44 (d, 1H), 5.56 (d, 1H), 7.2 (s, 1H), 7.36 (s, 1H). |
| 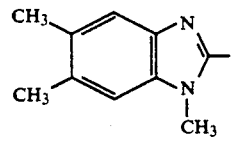 | 15 white solid, purified, 1:1 mixture of 1,5-dimethyl and 1,6-dimethyl compounds | (6β, 8S) | 1.32 (s, 3H), 1.54 (s, 3H), 2.36 (s, 1.5H), 2.38 (s, 1.5H), 3.76 (s, 3H), 4.2 (s, 1H), 4.36 (dd, 1H), 5.4 (d, 1H), 5.42 (d, 1H), 7.06–7.6 (m, 3H). IR(KBr) cm$^{-1}$: 3445, 1747, 1604. |
| 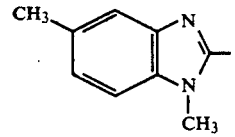 | 80 yellow solid, 1:1 mixture of 1,5-dimethyl and 1,6-dimethyl compounds | (6β, 8R) | 1.54 (s, 3H), 1.66 (s, 3H), 2.4 (s, 1.5H), 2.44 (s, 1.5H), 3.77 (s, 3H), 4.22 (s, 1H), 4.54 (dd, 1H), 5.52 (d, 1H), 5.64 (d, 1H), 7.1–7.7 (m, 3H). IR(KBr) cm$^{-1}$: 3412, 1757, 1602. |
| 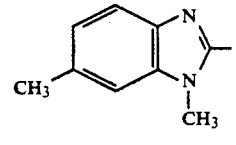 | 100 yellow solid | (6β, 8S) | 1.35 (s, 3H), 1.57 (s, 3H), 3.84 (s, 3H), 3.88 (s, 3H), 4.23 (s, 1H), 4.37 (dd, 1H), 5.4 (d, 1H), 5.44 (d, 1H), 6.48 (dd, 1H), 7.12 (d, 1H), 7.57 (d, 1H). |
| 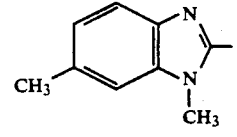 | 100 yellow solid | (6β, 8R) | 1.48 (s, 3H), 1.6 (s, 3H), 3.78 (s, 3H), 3.86 (s, 3H), 4.16 (s, 1H), 4.5 (dd, 1H), 5.48 (d, 1H), 5.58 (d, 1H), 6.96 (dd, 1H), 7.1 (d, 1H), 7.56 (d, 1H). |
| 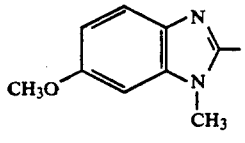 | 80 yellow solid | (6β, 8S) | 1.35 (s, 3H), 1.56 (s, 3H), 4.24 (s, 1H), 4.38 (dd, 1H), 5.20 (d, 1H), 5.22 (d, 1H), 7.04 (m, 1H), 7.22 (m, 1H), 7.48 (d, 1H). IR(KBr) cm$^{-1}$: 3411, 1747, 1610. |

| | | | |
|---|---|---|---|
| 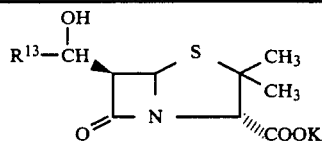 | | | |
| 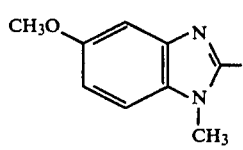 | 87 yellow solid | (6β, 8R) | 1.5 (s, 3H), 1.63 (s, 3H), 3.78 (s, 3H), 3.84 (s, 3H), 4.18 (s, 1H), 4.5 (dd, 1H), 5.5 (d, 1H), 5.6 (d, 1H), 7.0 (dd, 1H), 7.2 (d, 1H), 7.42 (d, 1H). |

EXAMPLE 74

Potassium (6 beta, 8S)-6-(1-methylbenzimidazol-2-yl)hydroxymethylpenicillanate

A. Allyl 6-bromo-6-(1-methylbenzimidazol-2-yl)hydroxymethylpenicillanate

A solution of 18.88 g 0.0473 mole) allyl 6,6-dibromopenicillanate in 400 ml methylene chloride was cooled to −78° C. and 16.90 ml (0.0473 mole) 2.8M methylmagnesium bromide in ethyl ether was added. The mixture was stirred at −78° C. for 30 minutes, a solution of 7.58 g (0.0473 mole) 1-methylbenzimidazole-2-carboxaldehyde in 30 ml methylene chloride was added and stirring continued for an additional 30 minutes. Acetic acid (2.71 ml, 0.0473 mole) was added, the mixture poured into saturated ammonium chloride solution, the layers separated and the organic layer dried (MgSO$_4$). Evaporation of solvent afforded an orange oil in quantitative yield which was used without purification except that the last traces of chlorinated solvent were removed by evaporation of its solution in benzene.

B. Allyl 6-(1-methylbenzimidazol-2-yl)hydroxymethylpenicillanate

The product obtained in Part A was dissolved in 150 ml tetrahydrofuran, 25.45 ml (0.0946 mole) tri-n-butyltin hydride was added, the mixture refluxed for six hours and stirred overnight at room temperature. The solvent was evaporated in vacuo, the residue taken up in acetonitrile/hexanes and the acetonitrile washed with hexanes. The acetonitrile layer was evaporated to dryness in vacuo to afford 16.86 g brown oil which was purified by flash column chromatography on 600 g of silica gel, eluting with 30% ethyl acetate in chloroform (v/v) to obtain 2 fractions:

1. 3.64 g (20.8%) more polar isomer having 6 beta, 8S stereochemistry as determined by $^1$H-NMR at 300 MHz. $^1$H-NMR(CDCl$_3$)ppm(delta): 1.32 (s, 3H), 1.58 (s, 3H), 3.71 (s, 3H), 4.43 (s, 1H), 4.52 (dd, 1H), 4.58 (d, 2H), 5.16–5.42 (m, 3H), 5.49 (d, 1H), 5.76–5.94 (m, 1H), 7.06–7.26 (m, 3H), 7.52–7.60 (m, 1H).

2. 2.6 g (14.9%) less polar isomer.

C. To 3.64 g (0.0098 mole) of the above 6 beta, 8S isomer in 20 ml ethyl acetate was added 360 mg tetrakis(triphenylphosphine)palladium (O), 360 mg triphenylphosphine and 19.6 ml potassium 2-ethylhexanoate solution and the mixture stirred at room temperature for one hour (nitrogen atmosphere). An excess of ethyl ether was added to precipitate the solid product which was collected by filtration and dried in vacuo to obtain 1.38 g of product. Addition of more ether to the mother liquors precipitated a second crop, 1.51 g. The two crops were combined and chromatographed, eluting with 15% acetonitrile in water (v/v) to obtain 1.37 g (35%) freeze-dried product as a pale yellow solid. 300 MHz $^1$H-NMR(D$_2$O)ppm(delta): 1.36 (s, 3H), 1.58 (s, 3H), 3.84 (s, 3H), 4.24 (s, 1H), 4.40 (dd, 1H), 5.38–5.48 (m, 2H), 7.22–7.3 (m, 2H), 7.44–7.54 (m, 1H), 7.6–8.7 (m, 1H). IR(KBr): 1610, 1750, 3440 cm$^{-1}$.

Analysis calculated for C$_{17}$H$_{18}$N$_3$O$_4$S.K.1.6H$_2$O: C, 47.67; H, 4.99; N, 9.81%.

Found: C, 47.74; H, 5.12; N, 9.73%.

EXAMPLE 75

Preparation of Pivaloyloxymethyl Esters

A. To a solution of 470 mg (1.28 mmole) potassium 6-(isothiazol-3-yl)methylene-1,1-dioxopenicillanate in 2 ml dimethylformamide was added 0.18 ml (1.28 mmole) chloromethylpivalate at room temperature. The mixture was stirred overnight, poured into water and extracted with ethyl ether (3×20 ml). The extracts were dried (Na$_2$SO$_4$) and solvent evaporated to obtain 500 mg (88%) of dark orange oil. Chromatography on a silica gel column, eluting with 9:1 chloroform/ethyl acetate gave pivaloyloxymethyl 6-(isothiazol-3-yl)methylene-1,1-dioxopenicillanate, 315 mg (55%) as a clear oil. $^1$H-NMR(CDCl$_3$)ppm(delta): 1.22 (m, 0.9H), 1.5 (s, 3H), 1.6 (s, 3H), 4.44 (s, 1H), 5.64 (s, 1H), 5.84 (AB quartet, 2H), 7.36 (s, 1H), 7.38 (d, 1H), 8.72 (d, 1H).

B. By the above method pivaloyloxymethyl 6-[1-methylbenzimidazol-2-yl)hydroxymethyl]penicillanate was prepared from the potassium salt in 61% yield as a tan solid. 300 MHz $^1$H-NMR(CDCl$_3$)ppm(delta): 1.22 (s, 9H), 1.44 (s, 3H), 1 66 (s, 3H), 2 92 [d, 1H(OH)], 3.86 (s, 3H), 4.52 (s, 1H), 4.59 (dd, 1H), 5.46 (d, 1H), 5.61 (d, 1H), 5.82 (AB quartet, 2H), 7.12–7.38 (m, 3H), 7.60–7.76 (m, 1H).

EXAMPLE 76

(5-Methyl-2-oxo-1,3-dioxolen-4-yl)methyl (6 beta, 8S)-6-(1-methylbenzimidazol-2-yl)hydroxymethylpenicillanate A mixture of 200 mg (0.5 mmole) potassium (6 beta, 8S)-6-(1-methylbenzimidazol-2-yl)hydroxymethylpenicillanate, 96 mg (0.5 mmole) 4-bromomethyl-5-methyl-2-oxo1,3-dioxolene and 4 ml dimethylformamide was stirred at room temperature for 18 hours. The resulting mixture was poured into water, extracted three times with ethyl ether, the extracts dried (MgSO$_4$) and solvent evaporated to obtain a gold colored oil which gradually solidified in vacuo, 110 mg (46%). 300 MHz $^1$H-NMR(CDCl$_3$)ppm(delta): 1.34 (s, 3H), 1.62 (s, 3H), 2.16 (s, 3H), 3.82 [s, 3H), 4.46 (s, 1H), 4.52 (dd, 1H), 4.88 (AB quartet, 2H), 5.41 (d, 1H), 5.56 (d, 1H), 7.08–7.38 (m, 3H), 7.58–7.78 (m, 1H).

EXAMPLE 77

1-(Ethoxycarbonyloxy)ethyl 6-(1-methylbenzimidazol-2-yl)hydroxymethylpenicillanate

Method A

To a solution of 150 mg (0.374 mmole) potassium 6-(1-methylbenzimidazol-2-yl)hydroxymethylpenicillanate in 2 ml dimethylformamide was added 0.051 ml (0.374 mmole) 1-chloroethylethylcarbonate and 56 mg (0.374 mmole) sodium iodide. The mixture was stirred overnight, poured into water, extracted with ethyl ether, the extracts dried (MgSO$_4$) and solvent evaporated in vacuo to obtain 60 mg of product as a pale yellow oil, a mixture of two isomers. 300 MHz $^1$H-NMR(CDCl$_3$)ppm(delta): 1.04–1.34 (m, 3H), 1.41 (s, 1.5H), 1.42 (s, 1.5H), 1.52 (d, 1.5H), 1.54 (d, 1.5H), 1.61 (s, 1.5H), 1.63 (s, 1.5H), 3.82 (s, 3H), 4.08 (q, 1H), 4.18 (q, 1H), 4.41 (s, 0.5H), 4.46 (s, 0.5H), 4.52 (dd, 1H), 5.39 (d, 1H), 5.52 (d, 0.5H), 5.54 (d, 0.5H), 6.66–6.82 (m, 1H), 7.06–7.40 (m, 3H), 7.50–7.80 (m, 1H).

EXAMPLE 78

1-(Ethoxycarbonyloxy)ethyl 6-(1-methylbenzimidazol-2-yl)hydroxymethylpenicillanate

Method B

A. 1-(ethoxycarbonyloxy)ethyl 6-bromo-6-(1-methylbenzimidazol-2-yl)hydroxymethylpenicillanate To a solution of 1-(ethoxycarbonyloxy)ethyl 6,6-dibromopenicillanate (8.24 g, 0.0186 mole) in 150 ml methylene chloride at −78° C. was added 6.64 ml (0.0186 mole) 2.8M methylmagnesium bromide in ethyl ether and the mixture stirred for 30 minutes. A solution of 3.28 g (0.02 mole) 1-methyl-2-benzimidazolecarboxaldehyde in 20 ml methylene chloride was added and stirring at −78° C. continued for one hour. To this was added 1.06 ml acetic acid, the mixture poured into water and saturated aqueous ammonium chloride solution added to effect separation of layers. The organic phase was washed with brine, dried (MgSO$_4$) and solvent evaporated to obtain a gold-colored oil. This was taken up in benzene and evaporated in vacuo to remove the last traces of chlorinated solvent. The resulting oil was used in the next step.

B. The product from Part A was dissolved in 125 ml distilled tetrahydrofuran and 10 ml (0.0372 mole) tri-n-butyltin hydride added. The mixture was heated at reflux for six hours and allowed to stir overnight at room temperature. The solvent was evaporated in vacuo, the residue dissolved in acetonitrile and washed three times with hexanes. The acetonitrile layer was evaporated in vacuo, the residual oil triturated with hexanes and petroleum ether to remove residual tin compounds. The crude product was purified by flash chromatography on a column of 150 g silica gel, eluting with 30% ethyl acetate in chloroform (v/v) to obtain 340 mg LP isomer and 419 mg of MP isomer. The LP fraction was triturated with ethyl ether to obtain 303 mg yellow solid which was identified as the (6 beta, 8R)-isomer by NMR. The MP isomer formed a white solid upon standing in vacuo (250 mg) identified as the (6 beta, 8S)-isomer. Both compounds have the (S)-stereochemistry in the 1-(ethoxycarbonyloxy)ethyl ester group. LP-isomer-300 MHz $^1$H-NMR(CDCl$_3$)ppm(delta): 1.28 (t, 3H), 1.46–1.62 (m, 6H), 1.66 (s, 3H), 3.74 (s, 3H), 4.18 (q, 2H), 4.3–4.42 (m, 2H), 5.36 (d, 1H), 5.56 (d, 1H), 6.74 (q, 1H), 7.10–7.30 (m, 3H), 7.58–7.72 (m, 1H). (6 beta, 8R, S-ester). MP-isomer-300 MHz $^1$H-NMR(CDCl$_3$)ppm(delta): 1.30 (t, 3H), 1.46 (s, 3H), 1.54 (d, 3H), 1.64 (s, 3H), 3.88 (s, 3H), 4.18 (q, 2H), 4.42 (s, 1H), 4.52 (dd, 1H), 5.46 (d, 1H), 5.58 (d, 1H), 6.74 (q, 1H), 7.16–7.42 (m, 3H), 7.64–7.72 (m, 1H). (6 beta, 8S, S-ester).

PREPARATION A

6-Chloropyridin-2-ylmethyltriphenylphosphonium Chloride (i) 6-Chloro-2-methylpyridine-1-oxide To a solution of 5.1 g (40 mmole) 6-chloro-2-picoline in 50 ml methylene chloride was added 8.625 g (40 mmole) of 80% m-chloroperbenzoic acid and the mixture was stirred at room temperature for 15 hours. The reaction was quenched with 0.5 ml saturated sodium thiosulfate and adjusted to pH 7.5 with sodium bicarbonate solution. The organic layer was washed with water, dried (Na$_2$SO$_4$) and solvent evaporated to give 4.84 g of N-oxide. $^1$H-NMR(CDCl$_3$)ppm (delta): 2.6 (s, 3H), 7.0–8.0 (m, 3H).

(ii) 6-Chloro-2-acetoxymethylpyridine

A solution of 4.8 g (0.035 mole) of the above N-oxide in 15 ml acetic anhydride was heated at 100° C. for one hour and distilled in vacuo to give 2.39 g of the desired product, b.p. 125°–128°/0.7mm, as a colorless oil. $^1$H-NMR(CDCl$_3$)ppm (delta): 2.1 (s, 3H), 5.1 (s, 2H), 7.0–7.8 (m, 3H).

(iii) 6-Chloro-2-pyridylmethanol

Hydrolysis of the product obtained in Part (ii) in 10 ml 2N hydrochloric acid at 70° C. for one hour, followed by neutralization (K$_2$CO$_3$), extraction with chloroform and evaporation of solvent from the dried extract gave 1.87 g of crude alcohol which was purified by column chromatography on silica gel to yield 0.982 g pure material. $^1$H-NMR(CDCl$_3$)ppm (delta): 4.8 (s, 2H), 5.3 (bs, 1H), 7.0–7.8(m, 3H).

(iv) 6-Chloro-2-chloromethylpyridine

6-Chloro-2-pyridylmethanol, 0.982 g (6.84 mmole) in 10 ml methylene chloride was treated with 0.814 g thionyl chloride at room temperature for one hour. The mixture was neutralized with saturated sodium bicarbonate solution, extracted with methylene chloride, the extracts dried and solvent evaporated to give 815 mg of product as colorless crystals. $^1$H-NMR(CDCl$_3$)ppm (delta): 4.7 (s, 2H), 7.1–8.0 (m, 3H).

(v) The Wittig reagent was prepared by dissolving 815 mg (5 mmole) of the product obtained in Part (iv) and 1.318 g (5 mmole) triphenylphosphine in toluene (10 ml) and heating the mixture at reflux for six hours. The precipitated product was collected by filtration to give 1.368 g (65%) of the title compound $^1$H-NMR(DMSO)-ppm (delta): 5.5 (s, 1H), 5.8 (s, 1H), 7.2–8.2 (m, 18H).

(vi) 4-Methoxypyridin-2-ylmethyltriphenylphosphonium chloride

Starting with 2-methyl-4-methoxypyridine-1-oxide (2.1 g) in the procedure of Part (ii) afforded 2.5 g of 2-acetoxymethyl-4-methoxypyridine which was contaminated with about 25% of 5-acetoxy-2-methyl-4-methoxypyridine. This mixture was dissolved in methanol (10 ml) containing 1.118 g (20.7 mmole) sodium methoxide and stirred at reflux for one hour. The methanol was evaporated in vacuo, the residue diluted with water, neutralized with dilute hydrochloric acid and extracted with chloroform. The organic layer was washed with brine, dried (MgSO$_4$) and concentrated in vacuo to give 853 mg (41%) 2-hydroxymethyl-4-methoxypyridine. $^1$H-NMR(CDCl$_3$)ppm (delta): 3.9 (s, 3H), 4.72 (s, 2H), 5.35 (bs, 1H), 6.7 (dd, 1H), 6.95 (d, 1H), 8.3 (d, 1H).

The hydroxymethyl compound obtained above was converted to 2-chloromethyl-4-methoxypyridine by the method of Part (iv), above, to provide 0.895 g (5.68 mmole). This was reacted with an equimolar amount of triphenylphosphine in toluene (10 ml) at reflux for 20 hours. The precipitated product was filtered to give 860 mg of the title compound as a yellow solid.

PREPARATION B

2-Quinolinylmethyltriphenylphosphonium Chloride

A solution of 2-chloromethylquinoline, 6.26 g (0.035 mole), and 9.20 g (0.035 mole) triphenylphosphine in 80 ml toluene was heated at reflux for three hours. The precipitated solid was collected on a filter and dried in vacuo to give 3.5 g (23%) of product as a brown solid.

PREPARATION C

3-Allyloxy-2-pyridylmethyltriphenylphosphonium Chloride (i) 3-Allyloxy-2-hydroxymethylpyridine To a sodium methoxide, methanol mixture made from 1.43 g (62 mmole) sodium metal and 100 ml methanol was added 5.9 g (31 mmole) 3-hydroxy-2-hydroxymethylpyridine and the methanol removed in vacuo. The resulting residue was dissolved in 80 ml dimethylsulfoxide (DMSO) and 3.0 ml (34.7 mmole) allyl bromide in 20 ml DMSO was added over 20 minutes at room temperature. The mixture was stirred for two hours, the DMSO distilled in vacuo and the reside partitioned between chloroform/water. The aqueous phase was adjusted to pH 7.5 and extracted three times with chloroform. The combined organic layers were washed with water, brine, dried (Na$_2$SO$_4$) and concentrated to give 3.48 g (68%) of the desired ether.

(ii) 3-Allyloxy-2-chloromethylpyridine

The product from Part A (3.43 g, 20.8 mmole) in 20 ml methylene chloride was treated with 1.5 equivlents (2.5 ml) thionyl chloride and the mixture stirred under nitrogen for two hours. The volatiles were removed in vacuo and the residue partitioned between methylene chloride and water. The aqueous layer was adjusted to pH 7.5 and extracted with fresh methylene chloride. The combined extracts were washed with water, brine, dried (Na$_2$SO$_4$) and solvent evaporated in vacuo to yield 3.28 g (86%) of the desired product which was used in the next step.

(iii) The product from Part (ii) (3.28 g, 17.9 mmole) was dissolved in 30 ml toluene and 4.69 g (17.9 mmole) triphenylphosphine was added. The mixture was stirred at reflux for three hours, then at room temperature for 12 hours. The product was isolated by filtration, washing with toluene to afford 3.89 g (49%) of the desired Wittig reagent.

PREPARATION D

Allyl 6-alpha-bromo-1,1-dioxopenicillanate (i) 6-alpha-Bromopenicillanic acid 1,1-dioxide A suspension of 20.26 g (0.0517 mole) 6,6-dibromopenicillanic acid 1,1-dioxide in 80 ml water was treated in portions with 13 g (0.155 mole) of solid sodium bicarbonate. The vigorous gas evolution was controlled by addition of ethyl acetate. Solid sodium bisulfite 6.76 g (0.062 mole) was then added in portions, the resulting mixture stirred for 35 minutes and adjusted to pH 1.0 with concentrated hydrochloric acid. The acidified mixture was diluted with ethyl acetate, the organic phase washed with brine, dried (Na$_2$SO$_4$) and solvent evaporated in vacuo. The residue was triturated with chloroform and filtered to give 6.72 g pale yellow solid. Another 3.2 g of product was obtained by concentrating the filtrate and treating the residue with chloroform.

(ii) To 6.352 g of the first crop material from above is 20 ml dimethylformamide was added 1.76 ml (20.3 mmole) allyl bromide, 2.83 ml (20.3 mmole) triethylamine and 0.2 g sodium bicarbonate and the mixture stirred under nitrogen at room temperature for 15 hours. Water was added, the mixture extracted with ethyl ether, the extracts washed with water, dried (Na$_2$SO$_4$) and solvent evaporated in vacuo to yield 4.60 g (64%) of the desired ester as in oil. $^1$H-NMR(CDCl$_3$)ppm (delta): 1.4 (s, 3H), 1.6 (s, 3H), 4.4 (s, 1H), 4.6 (d, 1H), 4.7 (d, 2H), 5.15 (d, 1H), 5.1–5.95 (m, 3H).

(iii) Allyl 6,6-dibromopenicillanate

Esterification of 6,6-dibromopenicillanic acid by the above procedure on a 0.417 molar scale gave 140 g (84%) of allyl ester as an oil. $^1$H-NMR(CDCl$_3$)ppm (delta): 1.5 (s, 3H), 1.65 (s, 3H), 4.6 (s, 1H), 4.75 (m, 2H), 5.3–5.6 (m, 2H), 5.85 (s, 1H), 5.8–6.3 (m, 1H).

PREPARATION E

2-Formyl-1-methylimidazole (i) 2-Hydroxymethyl-1-methylimidazole

A mixture of 50 g 1-methylimidazole and 100 ml 37% formaldehyde (sp. gr. 1.08) was placed in a stainless steel bomb (300 ml) and heated at 150° C. (bath temperature) for 17 hours. The bomb was then cooled in ice and the mixture removed, concentrated in vacuo and the residue stored at 4° C. overnight. The resulting mixture of crystals and oil was filtered, washing with ethyl acetate. The colorless crystals were dried in vacuo to afford 14.60 g of product. A second crop amounting to 6.48 g was obtained by reworking the mother liquor. Total yield 21.08 g (31%).

(ii) To a solution of 4.96 g (43.9 mmole) 2-hydroxymethyl-1-methylimidazole in 50 ml dioxane was added 4.90 g (44.1 mmole) selenium dioxide and the mixture stirred at 85°–90° C. for five hours, at room temperature for 36 hours, at 85° C. for eight hours and finally at room temperature for 15 hours. The reaction mixture was filtered, the solvent evaporated in vacuo to yield 4.81 g of crude aldehyde which was distilled to give 2.11 g of product as colorless crystals, b.p. 65° C. at 2.8 mm Hg.

PREPARATION F

6-Methyl-2-pyridylmethyltriohenylphosphonium Chloride (i) 6-Methyl-2-hydroxymethylpyridine 6-Methylpyridine-2-carboxaldehyde (0.44 mmole) in 50 ml methanol was reduced with 20.6 mmole sodium borohydride at 0°–5° C. After reduction was complete, the mixture was neutralized (pH 7.5) with 2N sulfuric acid, filtered, the filtrate concentrated and partitioned between chloroform and water. Evaporation of solvent from the organic layer gave 3.32 g of red-black oil which was used in the next step.

(ii) 2-Chloromethyl-6-methylpyridine

The above product 3.32 g (0.27 mmole) in 20 ml methylene chloride was treated with 1.94 ml (27 mmole) thionyl chloride at room temperature for one hour. The mixture was neutralized (NaHCO$_3$) and extracted with chloroform. Evaporation of solvent gave 3.22 g of product as an oil which was used in the next step. (iii) A solution of 3.22 g of the oil from Part (ii), 5.96 g triphenylphosphine in 30 ml toluene was heated at reflux for four hours. Filtration of the precipitate gave 3.93 g of the Wittig reagent as a brown solid.

PREPARATION G

2-Pyrazinylmethyltriphenylphosphonium Chloride (i) 2-Hydroxymethylpyrazine

To a solution of 11.29 g (79.2 mmole) 2-pyrazinecarbonyl chloride (prepared by treating the corresponding 2-carboxylic acid with a molar excess of thionyl chloride at the reflux temperature) in 100 ml tetrahydrofuran at −78° C. was added in portions over 20 minutes, 2.0 g 52.6 mmole of lithium aluminum hydride (95% pure). The mixture was stirred 10 minutes and allowed to warm to room temperature. The reaction was quenched with 2M sodium hydroxide, filtered, washing with methanol. Concentration of the filtrate in vacuo gave 4.12 g of dark solid which was used in the next step.

(ii) The above dark solid (4.12 g, 37.8 mmole) was dissolved in methylene chloride and 2.8 ml of thionyl chloride added at 0° C. The mixture was warmed to room temperature, stirred for 30 minutes, water added, the mixture neutralized and extracted with methylene chloride to afford 2.29 9 of yellow oil which was used in the next step.

(iii) To the above oil, 2.29 g, in 40 ml toluene was added 4.70 g triphenylphosphine and the mixture refluxed for three hours. Work up in the usual manner gave 1.995 g Wittig reagent as a brown solid.

PREPARATION H

4-Formylpyrimidine

A solution of 4-methylpyrimidine (10 g, 0.106 mole) in 100 ml dioxane was treated with 11.8 g selenium dioxide at room temperature and the mixture was heated at 100° C. for 15 hours. After adding 2.5 g selenium dioxide, heating was continued one hour, the mixture cooled, filtered, and the cake washed with ethyl acetate. The filtrate and washings were evaporated to dryness in vacuo. The residual dark oil was taken up in methylene chloride, filtered and the solvent evaporated. The residue was crystallized from a small amount of methylene chloride to provide the title aldehyde. $^1$H-NMR(CDCl$_3$)ppm (delta): 7.87 (dd, 1H), 9.06 (d, 1H), 9.43 (d, 1H), 10.0 (s, 1H).

PREPARATION I

Diphenylmethyl 6-alpha-bromo-1,1-dioxopenicillanate

To a solution of 21.557 g (0.1 mole) diphenyldiazomethane in 400 ml dry tetrahydrofuran was added in portions over 30 minutes 31.2 g (0.1 mole) 6-alpha-bromo-1,1-dioxopenicillanic acid. The reaction was slightly exothermic. The mixture was stirred one hour, the solvent evaporated and the residue dissolved in ethyl acetate (50 ml). Ethyl ether (400 ml) was added and the resulting mixture was stored at 4° C. No crystal formed after 18 hours. The mixture was then concentrated in vacuo to yield 51.2 g yellow solid which was chromatographed on silica gel, eluting with chloroform to yield 14.86 g colorless product as a glass. $^1$H-NMR(CDCl$_3$)ppm (delta): 1.26 (s, 3H), 1.57 (s, 3H), 4.55 (s, 1H), 4.70 (d, 1H), 5.13 (d, 1H), 6.9 (s, 1H), 7.27 (s, 10H).

PREPARATION J

Benzothiazole-2-carboxaldehyde

A solution of freshly distilled (b.p. 82° C., 2 torr) benzothiazole (10 g, 0.074 mole) in 250 ml tetrahydrofuran was colloed under nitrogen to −78° C. and stirred at this temperature for 15 minutes. To this was added dropwise over 15 minutes 29.6 ml (0.074 mole) 2,5M n-butyl-lithium, stirring continued for 25 minutes, and 8.6 ml (0.111 mole) dimethylformamide was added and the reaction mixture stirred for an hour. The mixture was allowed to warm to room temperature, 200 g ice was added and the solvent evaporated *in vacuo*. The aqueous residue was extracted with 5×100 ml ethyl acetate, the extractes dried (MgSO$_4$), concentrated to a small volume and chromatographed on a silica gel column, eluting with 96:4 chloroform/ethyl acetate to yield 8.4 g of the desired aldehyde, m.p. 74.5–75° C. $^1$-H—NMR(CDCl$_3$)ppm (delta): 7.54 (m, 2H), 7.97 (m, 1H), 8.21 (m, 1H), 10.1 (s,1H.

The following aldehydes were prepared in like manner by the above procedure:

| Starting Compound | Aldehyde | % Yield | $^1$H-NMR(CDCl$_3$)ppm(delta): |
|---|---|---|---|
| 4,5-dimethylthiazole | 2-formyl-4,5-dimethylthiazole | 98 amber oil b.p. 120–122° C. at 25 torr | |
| 1-methylpyrazole | 5-formyl-1-methylpyrazole | 50 | 4.2 (s, 3H), 8.05 (s, 1H), 10.00 (s, 1H). |

| Starting Compound | Aldehyde | % Yield | $^1$H-NMR(CDCl$_3$)ppm(delta): |
|---|---|---|---|
| N∕=∖N NCH(OC$_2$H$_5$)$_2$ ** | N∕=∖N(CHO) NCH(OC$_2$H$_5$)$_2$ | 82 | 1.2 (t, 6H), 3.6 (q, 2H), 3.64 (q, 2H), 6.95 (s, 1H), 7.21 (d, 1H), 7.55 (d, 1H), 8.23 (d, 1H). |

*Prepared by reaction of 1H-1,2,4-triazine with methyl iodide in ethanolic sodium ethoxide in 37% yield as a solid.
**Prepared from imidazole and ethyl orthoformate by the method of Curtis et al., J. Org. Chem. 45, 4038 (1980).

PREPARATION K

Pyrazine-2-carboxaldehyde

Pyrazine-2-carboxylic acid was esterified with methanolic sulfuric acid at reflux for five hours. The methanol was evaporated in vacuo, diluted with methylene chloride and neutralized with sodium bicarbonate pH 7.5). The dried organic layer was concentrated to afford methyl pyrazine-2-carboxylate as an off-white solid in 84% yield which was recrystallized from isopropanol, ethyl ether to give yellow needles. $^1$H-NMR(CDCl$_3$)ppm (delta): 4.1 (s, 3H), 8.93 (m, 2H), 9.47 (m, 1H).

The methyl ester, 20 g (0.145 mole) was dissolved in 600 ml dry tetrahydrofuran, cooled to −78° C. and a solution of 5.8 g of 98% lithium aluminum hydride in THF was added dropwise over 15 minutes. The mixture was stirred for 30 minutes at −78° C., 20 ml acetic acid added and the mixture concentrated under reduced pressure. The residue was partitioned between 2N hydrochloric acid (30 ml) and chloroform, the combined organic layers washed with water, dried and evaporated to afford 8.53 g of crude product which was purified by passing it through a silica gel column, eluting with 4:1 methylene chloride/ethyl acetate to yield 5.02 g of light yellow needles. $^1$H-NMR(CDCl$_3$)ppm (delta): 3 8.38 (m, 2H), 8.7 (bs, 1H), 9.7 (s, 1H).

PREPARATION L

2-Phenyl-1,2,3-triazole-4-carboxaldehyde (i) Reaction of 0.34 mole acetone dicarboxylic acid in 100 ml water with 0.58 mole sodium nitrite at 0°-10° C. and subsequent addition of dilute nitric acid to precipitate the product gave a 46% yield of the dioxime, 1,3-dioximino-2-oxopropane as tan crystals.

(ii) The dioxime, (0.158 mole) in ethanol (170 ml) was reacted with equimolar amounts of phenylhydrazine hydrochloride and sodium acetate at 70° C. for 30 minutes. Water (170 ml) was added, the mixture heated to 85° C. reduced in volume to 250 ml and cooled to yield 24.7 g of the phenylhydrazone. $^1$H-NMR(CD$_3$COCD$_3$)ppm (delta): 7.3 (m, 5H), 7.9 (s, 1H), 8.6 (s, 1H), 10.5 (bs, 1H), 11.4 (bs, 1H), 12.3 (s, 1H).

(iii) The above dioximephenylhydrazone, 24.7 g (0.119 mole) was stirred at room temperature with 500 ml of acetic anhydride for 30 minutes and the mixture poured into water, stirred 20 minutes and filtered. The resulting crude solid was recrystallized from benzene/ethyl acetate to afford 15.47 g (52%) of the monoacetate, HON=CH-C(=NNHC$_6$H$_5$)CH=NOCOCH$_3$, as a yellow powder. $^1$H-NMR(CDCl$_3$, acetone): 1.85 (s, 3H), 7.09 (m, 5H), 7.95 (s, 1H), 8.3 (s, 1H), 10.9 (bs, 1H), 12.25 (s, 1H). (iv) A solution of 15.40 g (0.062 mole) of the monoacetate, obtained above, and 22.16 g (0.068 mole) cesium carbonate in 400 ml tetrahydrofuran was stirred at room temperature for one hour, filtered and the filtrate concentrated to afford a yellow residue. The residue was dissolved in 700 ml hot 1:2 isopropyl ether/cyclohexane and concentrated to 200 ml to afford 9.41 g (80%) of 2-phenyl-1,2,3-triazole-4-carboxaldehyde oxime as a yellow powder which was used in the next step.

(v) A mixture of the oxime. 9.41 g (0.0497 mole). 4.4B g s-trioxane and 300 ml 2N hydrochloric acid was heated at reflux for 3.5 hours. The aqueous phase was extracted with ethyl ether, the combined ether layers washed with water, dried (MgSO$_4$) and the ether evaporated in vacuo to yield 6 g of crystalline aldehyde. $^1$H-NMR (CDCl$_3$)ppm (delta): 7.6 (m, 3H), 8.25 (m, 3H), 10.25 (s, 1H); m.p. 66°-67° C.

PREPARATION M

5-Methylisoxazol-3-carboxaldehyde (i) Ethyl 5-methylisoxazol-3-carboxylate

A mixture of 0.16 mole ethyl 2,4-dioxovalerate and 0.08 mole hydroxylamine sulfate, 50 ml ethanol and 70 ml toluene was stirred at 40° C. for four hours. The mixture was cooled to 15'-20° C., 1.8 g of concentrated ammonium hydroxide added and stirring continued at room temperature for 60 hours. The mixture was poured into water/toluene, the aqueous layer extracted with toluene, the organic layers combined, washed with brine and dried (Na$_2$SO$_4$). Evaporation of solvent in vacuo gave a yellow liquid which was distilled to afford 14.68 g of product, b.p. 120°-124° C. at 30 torr which crystallized upon standing.

(ii) The ethyl ester obtained above, 2.0 g (14.4 mole), in 75 ml toluene was reduced with an equimolar amount of 1M diisobutylaluminum hydride in hexane under nitrogen at −75 to −70° C. After stirring for 30 minutes, the reaction was quenched with ammonium chloride solution, warmed to room temperature and the solvent evaporated in vacuo. The residue was triturated with hot methanol, evaporated to afford 0.85 g of product as a colorless oil $^1$H-NMR(CDCl$_3$)ppm (delta): 2.4 (s, 3H), 6.3 (d, 1H), 9.0 (s, 1H).

(iii) Benzoxazole-2-carboxaldehyde

The title compound was prepared from methyl benzoxazole-2-carboxylate by the method of part (ii), above, on a 0.041 molar scale; yield 35% as a yellow oil. $^1$H-NMR(CDCl$_3$)ppm(delta): 7.3-8.1 (m, 4H), 10.0 (s, 1H).

The above starting compound was obtained from o-aminophenol in two steps. First by reaction with a molar equivalent of oxalyl chloride in m-dichlorobenzene solvent at reflux (∼185° C.) to obtain 2,3-dioxobenzoxazolidine in nearly quantitative yield. This was then reacted with a slight excess of thionyl chloride in refluxing benzene and the resulting 3-chloro-2-hydroxybenzoxazine treated with an equimolar amount of sodium bicarbonate in methanol at reflux overnight to afford the desired methyl benzoxazole-2-carboxylate; m.p. 101°-102° C. $^1$H-NMR(CDCl$_3$)ppm(delta): 4.05 (s, 3H), 7.3-8.0 (m, 4H).

PREPARATION N (i) Oxidation of 6-methoxy-2-methylbenzothiazole (10.0 g, 55.9 mmole) with selenium dioxide (6.2 g, 55.9 mmole) in 300 ml dioxane for six hours by the method of Preparation H gave 6.0 g of 6-methoxy-2-formylbenzothiazole after chromatography of the crude product on silica gel, eluting with chloroform. $^1$H-NMR(CDCl$_3$)-ppm(delta): 3.9 (s, 3H), 7.1–7.5 (m, 2H), 8.0–8.3(m, 1H), 10.1 (s, 1H).

PREPARATION O (i) 2-Formyl-3-methylbenzimidazole

To a solution of 3-methylbenzimidazole* (12.6 g, 0.086 mole) in 100 ml tetrahydrofuran at −78° C. was added 34.3 ml of 2.5M n-butyllithium over a 30-minute period and the mixture stirred for twenty minutes. Ethyl formate (6.95 ml 0.086 mole) was added over five minutes and the stirring was continued for one hour. The reaction was quenched with acetic acid (4.92 ml, 0.086 mole), the mixture warmed to 10° C. and poured into 300 ml water and extracted three times with 200 ml portions of ethyl acetate. The extracts were dried (Na$_2$SO$_4$), solvent evaporated and the resulting yellow residue triturated with ethyl ether to obtain 4.4 g pale yellow solid, and a second crop (1.65 g) was obtained by concentration of the ether to one-third volume. Total yield: 6.05 g, (44%). $^1$H-NMR(CDCl$_3$)-ppm(delta): 4.1 (s, 3H), 7.1–7.45 (m, 3H), 7.6–8.0 (m, 1H), 10.1 (s, 1H).

*This was obtained by reaction of benzimidazole in dimethylformamide with equimolar amounts of sodium hydride and methyl iodide for two hours at room temperature. The mixture was poured into water, acidified with concentrated hydrochloric acid and extracted with ethyl acetate; yield 95% yellow oil. The 3-ethyl and 3-n-propyl analogs were obtained in like manner.

(ii) 2-Formyl-3-ethylbenzimidazole

This was obtained by the above method from 3-ethylbenzimidazole in 67% yield after column chromatography on silica gel. $^1$H-NMR(CDCl$_3$)ppm(delta): 1.4 (t, 3H), 4.55 (q, 2H), 7.2–7.5 (m, 3H), 7.91 (m, 1H), 10.1 (s, 1H).

(iii) Similarly 2-formyl-3-n-propylbenzimidazole was obtained in 25% yield from 3-n-propylbenzimidazole. $^1$H-NMR(CDCl$_3$)ppm(delta): 0.8 (t, 3H), 1.78 (m, 2H), 4.4 (t, 2H), 7.1–7.5 (m, 3H), 7.6–8.0 (m, 1H), 10.1 (s, 1H).

(iv) Also 8.14 g (0.051 mole) 3-methyl-5-phenylimidazole afforded 2-formyl-3-methyl-5-phenylimidazole by the above method in 43% yield as a colorless solid.

(v) 2-Formyl-3,5,6-trimethylbenzimidazole was prepared by the above method in 44% yield. $^1$H-NMR(CDCl$_3$)ppm(delta): 2.4 (s, 6H), 4.0 (s, 3H), 7.15 (s, 1H), 7.6 (s, 1H), 10.0 (s, 1H), The starting 3,5,6-trimethylbenzimidazole was obtained by methylation of 5,6-dimethylbenzimidazole with methyl iodide and sodium hydride in dimethylformamide. $^1$H-NMR(CDCl$_3$)ppm(delta): 2.45 (s, 6H), 3.8 (s, 3H), 7.2 (s, 1H), 7.6 (s, 1H), 7.8 (s, 1H).

PREPARATION P

Mixture of 1,5-Dimethyl-2-formylbenzimidzaole and 1,6-Dimethyl-2-formylbenzimazole (i) 1,2-bis(5-methylbenzimidazol-2-yl)ethylene glycol A mixture of 15.0 g (0.10 mole) tartaric acid, 29.32 g (0.24 mole) 3,4-diaminotoluene, 25 ml water, 15 ml ethanol, 25 ml hydrochloric acid (conc.) and 10 ml 85% phosphoric acid was heated at 120° C. for 40 hours, poured into water and the mixture acidified with concentrated hydrochloric acid. After extraction with chloroform and making the aqueous phase alkaline with sodium hydroxide, a precipitate formed and was collected by filtration. The solid was washed with a small amount of acetone and held in vacuo for 18 hours. The residual moisture was removed by azeotropic distillation of its mixture with benzene.

(ii) The above product, 2.0 g (6.17 mmole), was dissolved in 50 ml dimethylformamide and 0.592 g (12.3 mmole) of 50% sodium hydride was added in portions over 30 minutes. The mixture was stirred an additional 30 minutes, then 0.760 ml (12.3 mmole) methyl iodide was added and stirring continued for 18 hours at room temperature. The mixture was poured into water, acidified (pH 2) with hydrochloric acid and extracted three times with chloroform. After making the aqueous phase alkaline (NaOH), it was again extracted with chloroform to obtain 640 mg of off-white solid which is a mixture of isomers of 1,2-bis(1,5(6)-dimethylbenzimidazol-2-yl)ethylene glycol.

(iii) To a suspension of 4.80 g (12.5 mole) of the product of Part (ii) in 160 ml 1N sulfuric acid was added 2.68 g (12.5 mmole) sodium metaperiodate and the mixture stirred at room temperature for 18 hours. After neutralizing to pH 7.5–8.0 with sodium bicarbonate, the mixture was extracted with ethyl acetate, the extracts dried (MgSO$_4$) and solvent evaporated to yield 3.77 g of a mixture of 1,5-dimethyl-2-formylbenzimidazole and the corresponding 1,6-dimethyl compound. The mixture of isomers was used without further purification.

(iv) Starting with 4-methoxy-1,2-phenylenediamine in the procedure of Part (i), above, methylation and periodate oxidation by the methods of Parts (ii) and (iii), above, afforded a mixture of isomers of 1-methyl-5-methoxy-2-formylbenzimidazole and 1-methyl-6-methoxy-2-formylbenzimidazole which were separated by column chromatography on silica gel, eluting with 19:1 chloroform/ethyl acetate.

1-methyl-6-methoxy-2-formylbenzimidazole:
$^1$H-NMR(CDCl$_3$)ppm(delta): 3.8 (s, 3H), 4.05 (s, 3H), 6.6–7.2 (m, 1H), 7.6–7.9 (m, 1H), 10.0 (s, 1H).

1-methyl-5-methoxy-2-formylbenzimidazole:
$^1$H-NMR(CDCl$_3$)ppm(delta): 3.9 (s, 3H), 4.1 (s, 3H), 7.05–7.5 (m, 3H), 10.1 (s, 1H).

PREPARATION Q

1-Dimethoxymethyl-2-formyl-4-phenylimidazole and its 5-phenyl isomer (i) 1-Dimethoxymethyl-4-phenylimidazole and its 5-phenyl isomer To a mixture of 10.00 g (0.069 mole) 4-phenylimidazole, 30.35 ml (0.28 mole) methylorthoformate was added a few drops of concentrated sulfuric acid, and the mixture was heated at 135° C. for 22 hours. After cooling to room temperature, the mixture was poured into saturated aqueous sodium bicarbonate solution and extracted with ethyl acetate. The combined extracts were washed three times with sodium bicarbonate solution, dried over anhydrous sodium sulfate and evaporated in vacuo to afford 12.98 g of green-gray oil, (86% yield), a mixture of 4-phenyl and 5-phenyl isomers. $^1$H-NMR(CDCl$_3$)ppm(delta): 3.31 (s, 6H), 5.85 (s, 1H), 6.95–7.50 (m, 4H), 7.50–7.88 (m, 3H).

(ii) 2-Formyl-1-dimethoxymethyl-4-phenylimidazole (A) and 2-Formyl-1-dimethoxymethyl-5-phenylimidazole (B)

The mixture of isomers obtained in Part (i) (12.98 g, 0.059 mole) was dissolved in 150 ml freshly distilled tetrahydrofuran, cooled to −78° C. and 23.78 ml (0.059 mole) 2.5M n-butyllithium was added over ten minutes. The mixture was stirred for 45 minutes, 4.77 ml (0.059 mole) ethyl formate added and stirring continued for one hour at −78° C. Acetic acid, 3.38 ml (0.059 mole) was added, the mixture poured into water, extracted with ethyl acetate and the combined extracts dried over anhydrous sodium sulfate. Evaporation of solvent yielded 14.19 g (97.6%) of the mixed products as a light tan solid. The ratio of isomer A:B was determined as 2:1. $^1$H-NMR(CDCl$_3$)ppm(delta): 3.38 (s, 0.33×3H), 3.47 (s, 0.66×3H), 5.93 (s, 0.33×1H), 6.83 (s, 0.66×1H), 7.06–7.93 (m, 6H), 9.83 (s, 0.33×1H), 9.86 (s, 0.66×1H).

I claim:

1. A compound of the formula

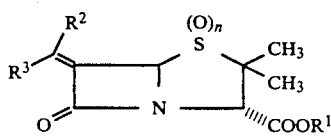

wherein n is zero, 1 or 2; $R^1$ is $R^a$ or $R^b$ where $R^a$ is the residue of a carboxy protecting group selected from tetrahydropyranyl, allyl, benzyl, 4-nitrobenzyl, benzhydryl, 2,2,2-trichloroethyl, t-butyl and phenacyl; and $R^b$ is hydrogen or the residue of an ester group readily hydrolyzable in vivo selected from 3-phthalidyl, 4-crotonolactonyl, gamma-butyrolacton-4-yl,

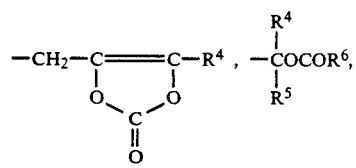

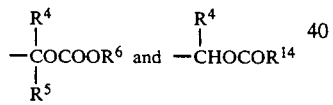

where $R^4$ and $R^5$ are each hydrogen or $CH_3$, $R^6$ is $(C_1-C_5)$-alkyl, and $R^{14}$ is

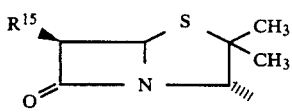

where $R^{15}$ is 2-phenylacetamido, 2-phenoxyacetamido, D-2-amino-2-phenylacetamido, D-2-amino-2-(4-hydroxyphenyl)acetamido, 2-carboxy-2-phenylacetamido, 2-carboxy-2-(2-thienyl)acetamido, 2-carboxy-2-(3-thienyl)-acetamido, D-2-(4-ethyl-2,3-dioxopiperazinocarbonylamino)-2-phenylacetamido or 2,2-dimethyl-4-phenyl-5-imidazolidinone-1-yl;

one of $R^2$ and $R^3$ is hydrogen and the other is Cl, CH$_2$OH, vinyl, $(C_1-C_4)$alkylthio, $(C_1-C_4)$alkylsulfonyl, furyl, thienyl, N-methylpyrrolyl, N-acetylpyrrolyl,

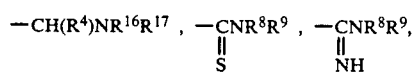

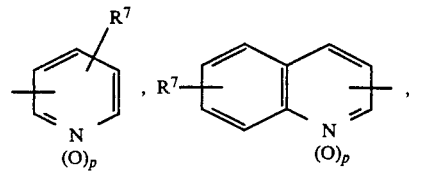

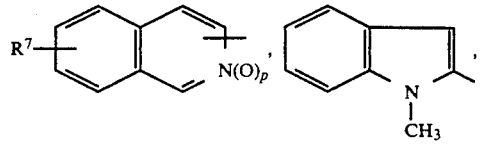

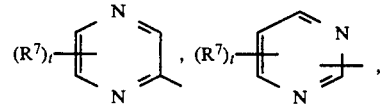

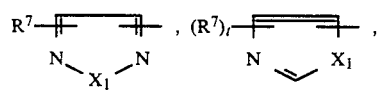

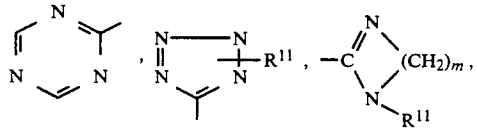

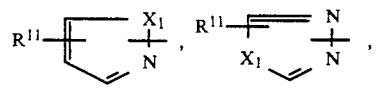

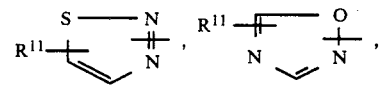

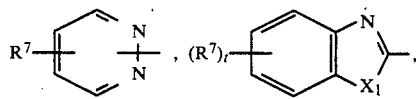

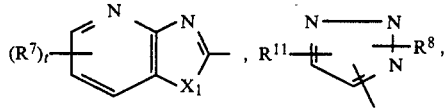

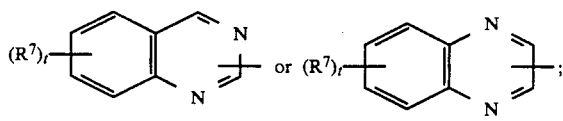

and m is 2 or 3, p is zero or 1, t is zero, 1 or 2, $X_1$ is S, O or $NR^{11}$, $R^7$ is hydrogen, $(C_1-C_4)$alkyl, $(C_1-C_4)$alkoxy, allyloxy, hydroxyl, carboxyl, $(C_2-C_5)$-alkoxycarbonyl, $(C_1-C_5)$alkylcarbonyl, phenyl, benzyl, naphthyl, pyridyl $NR^8R^9$, $CONR^8R^9$, $NHCOR^{10}$, $NO_2$, Cl, Br, $CF_3$ or $SR^8$; and $R^9$ are each hydrogen, $(C_1-C_4)$-alkyl, phenyl or benzyl; $R^{10}$ is $(C_1-C_4)$alkyl, $CF_3$ or phenyl; and $R^{11}$ is hydrogen, $(C_1-C_3)$ alkyl, $C_6H_5CH_2$ or $CH_3CO$; $R^{16}$ and $R^{17}$ are each H, $(C_1-C_4)$alkyl, $(C_2-C_4)$-hydroxyalkyl, or taken together with the nitrogen atom to which they are attached $R^{16}$ and $R^{17}$ form a pyrrolidino, piperidino, morpholino, thiomorpholino or 4-methylpiperazino group; or a pharmaceutically acceptable acid addition salt of said compound where $R^2$ or $R^3$ contains a basic nitrogen atom, or a pharmaceutically acceptable cationic salt of said compound wherein $R^1$ is hydrogen or $R^2$ or $R^3$ contains a carboxyl group.

2. A compound according to claim 1 wherein $R^1$ is $R^a$.

3. A compound according claim 1 wherein $R^1$ is $R^b$.

4. A compound according to claim 3 wherein $R^b$ is H, a pharmaceutically acceptable cationic salt thereof, $$-CH_2-C=C-R^4 \quad R^4 \quad$$
$$\phantom{-CH_2-}O\diagdown_C\diagup O\,,\ -\underset{R^5}{\overset{|}{C}}OCOR^6,$$
$$\phantom{-CH_2-O\diagdown_C\diagup O\,,\ -}\overset{\|}{O}$$

$$-\underset{R^5}{\overset{R^4}{\overset{|}{C}}}OCOOR^6 \text{ or } -CH_2O\overset{O}{\overset{\|}{C}}R^{14}.$$

5. A compound according to claim 4 wherein $R^b$ is H, a pharmaceutically acceptable cationic salt thereof, $$-CH_2-C=C-R^4 \quad R^4 \quad R^4$$
$$\phantom{-CH_2-}O\diagdown_C\diagup O\,,\ -\underset{R^5}{\overset{|}{C}}OCOR^6 \text{ or } -\underset{R^5}{\overset{|}{C}}OCOOR^6.$$
$$\phantom{-CH_2-O\diagdown_C\diagup O\,,\ -}\overset{\|}{O}$$

6. A compound according to claim 4 wherein $R^b$ is H, a sodium or potassium salt thereof, pivaloyloxymethyl or $CH_2OCOR^{14}$ where $R^{14}$ is

[structure]

and $R^{15}$ is D-2-amino-2-phenylacetamido or D-2-amino-2-(4-hydroxyphenyl)acetamido.

7. A compound according to claim 6 wherein n is zero or 2, one of $R^2$ and $R^3$ is H and the other is $CH_2OH$, methylsulfonyl, 2-furyl, 2-thienyl, N-methylpyrrolyl,

[structures]

8. A compound according to claim 7 wherein n is 2.

9. A compound according to claim 8 wherein one of $R^2$ and $R^3$ is H and the other is 2-pyridyl, N-oxo-2-pyridyl, 2-quinolyl, 3-allyloxy-2-pyridyl, 3-methoxy-2-pyridyl, 4-methoxy-2-pyridyl, 3-hydroxy-2-pyridyl, 6-methyl-2-pyridyl, 1-methyl-2-imidazolyl, 2-thiazolyl, 4,5-dimethyl-2-thiazolyl, 4-methyl-2-thiazolyl, 3-isothiazolyl, 4-pyrimidinyl, 2-pyrimidinyl, 4,6-dimethyl-2-pyrimidinyl, 2-pyrazinyl, 2-methyl-1,2,4-triazol-3-yl or benzothiazol-2-yl.

10. A compound according to claim 9 wherein one of $R^2$ and $R^3$ is H and the other is 2-pyridyl, 3-allyl-oxy-2-pyridyl, 2-pyrazinyl, 2-pyrimidinyl, 3-hydroxy-2-pyridyl, 4-methoxy-2-pyridyl, 2-thiazolyl or 3-isothiazolyl.

11. A compound according to claim 10 wherein one of $R^2$ and $R^3$ is H and the other is 2-pyridyl or a sodium or potassium salt thereof.

12. A compound according to claim 10 wherein one of $R^2$ and $R^3$ is H and the other is 3-hydroxy-2-pyridyl or a sodium or potassium salt thereof.

13. A compound according to claim 10 wherein one of $R^2$ and $R^3$ is H and the other is 2-pyrazinyl or a sodium or potassium salt thereof.

14. A compound according to claim 10 wherein one of $R^2$ and $R^3$ is H and the other is 2-thiazolyl or a sodium or potassium salt thereof.

15. A compound according to claim 10 wherein one of $R^2$ and $R^3$ is H and the other is 3-isothiazolyl or a sodium or potassium salt thereof.

16. The compound according to claim 11:
1,1-dioxo-6(E)-(2-pyridyl)methylenepenicillanic acid.

17. The compound according to claim 14:
1,1-dioxo-6(E)-(2-thiazolyl)methylenepenicillanic acid.

18. The compound according to claim 15:
1,1-dioxo-6(E)-(3-isothiazolyl)methylenepenicillanic acid.

19. A compound according to claim 2 wherein $R^a$ is allyl.

20. A pharmaceutical composition for treating bacterial infections which comprises in a weight ratio of 1:3 to 3:1 a compound of claim 5 and a beta-lactam antibiotic.

21. A pharmaceutical composition of claim 20 wherein the beta-lactam antibiotic is
amoxicillin,
ampicillin,
apalcillin,
azlocillin,
azthreonam,
bacampicillin,
carbenicillin,
carbenicillin indanyl,
carbenicillin phenyl,
cefaclor,
cefadroxil,
cefaloram,
cefamandole,
cefamandole nafate,
cefaparole,
cefatrizine,
cefazolin,
cefbuperazone
cefmenoxime,
cefonicid,
cefodizime,
cefoperazone,
ceforanide, cefotaxime,
cefoxitin,
cefotiam,
cefpiramide,
cefpirome,
cefsulodin,
ceftazidime
ceftizoxime,
ceftriaxone,
cefuroxime,
cephacetrile,
cephalexin,
cephaloglycin,
cephaloridine,
cephalothin,
cephapirin,
cephradine,
cyclacillin,
epicillin
furazlocillin,
hetacillin,
lenampicillin
levopropylcillin,
mecillinam,
mezlocillin,
penicillin G,
penicillin V,
phenethicillin,
piperacillin,
pirbenicillin,
pivampicillin,
sarmoxicillin,
sarpicillin,
suncillin,
talampicillin,
ticarcillin, 7-[2-(2-amino-4-thiazolyl)-2-methoxyiminoacetamido]-3-(N-methylpyrrolidinium)-methyl-3-cephem-4-carboxylate, or 7-[D-(2-[4-carboxy-5-imidazolcarboxamido])-2-phenylacetamido]-3-[4-(2-sulfonatoethyl)pyridinium]-3-cephem-4-carboxylic acid; or a pharmaceutically acceptable salt thereof.

22. A pharmaceutical composition according to claim 21 wherein the beta-lactam antibiotic is ampicillin, hetacillin, pivampicillin, bacampicillin, talampicillin, amoxicillin or lenampicillin.

23. A pharmaceutical composition for treating bacterial infections which comprises a pharmaceutically acceptable carrier and a compound according to claim 4 wherein $R^b$ is

24. A method of treating a bacterial infection in a mammalian subject, which comprises administering to a mammal in need of such treatment an antibacterially effective amount of a pharmaceutical composition according to claim 20.

25. A method of treating a bacterial infection in a mammalian subject, which comprises administering to a mammal in need of such treatment an antibacterially effective amount of a pharmaceutical composition according to claim 23.

* * * * *